(12) United States Patent
Discher et al.

(10) Patent No.: US 9,920,295 B2
(45) Date of Patent: Mar. 20, 2018

(54) BIOREACTOR FOR ISOLATION OF RARE CELLS AND METHODS OF USE

(71) Applicant: The Trustees of the University of Pennsylvania, Philadelphia, PA (US)

(72) Inventors: Dennis E. Discher, Philadelphia, PA (US); Jae-Won Shin, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/772,750

(22) Filed: Feb. 21, 2013

(65) Prior Publication Data

US 2013/0216506 A1 Aug. 22, 2013

Related U.S. Application Data

(60) Provisional application No. 61/601,364, filed on Feb. 21, 2012.

(51) Int. Cl.
*C12M 1/00* (2006.01)
*A61K 35/19* (2015.01)
(Continued)

(52) U.S. Cl.
CPC ............ *C12M 47/04* (2013.01); *A61K 35/19* (2013.01); *A61K 35/28* (2013.01); *C12N 5/0644* (2013.01); *C12N 5/0647* (2013.01); *C12Q 1/6881* (2013.01); *G01N 1/10* (2013.01); *G01N 33/56972* (2013.01); *C12N 2501/998* (2013.01)

(58) Field of Classification Search
CPC .... C12M 47/04; C12Q 1/6881; C12N 5/0644; C12N 5/0647; G01N 1/10; G01N 33/56972; A61K 35/28; A61K 35/19

USPC ....... 424/93.7; 435/2, 304.1, 309.1, 325, 34, 435/6.12, 7.92; 506/9
See application file for complete search history.

(56) References Cited

U.S. PATENT DOCUMENTS 5,026,650 A * 6/1991 Schwarz et al. ........... 435/297.1
5,194,596 A * 3/1993 Tischer et al. ................ 530/399
(Continued)

FOREIGN PATENT DOCUMENTS

WO WO 2007/087402 * 8/2007
WO WO2009/005769 8/2009

OTHER PUBLICATIONS

Cooper (2000). The Cell: A Molecular Approach, 2nd Ed., ISBN: 0-87893-106-6, 7 page excerpt from Chapter 11.*
(Continued)

*Primary Examiner* — Scott Long
*Assistant Examiner* — Sean C. Barron
(74) *Attorney, Agent, or Firm* — Saul Ewing Arnstein & Lehr LLP; Kathryn Doyle; Domingos J. Silva

(57) ABSTRACT

The present invention relates to a bioreactor apparatus, and methods of use, for the isolation of rare blood cells, including hematopoietic stem cells and megakaryocytes. The apparatus includes a soft substrate and an anti-contractility agent, thereby providing a soft microenvironment to cultured cells. The apparatus of the invention is permissive for the survival of non-dividing cells while dividing cells are eliminated. This unique property allows for the simple isolation of rare blood cells without the use of costly equipment and antibodies.

11 Claims, 55 Drawing Sheets
(55 of 55 Drawing Sheet(s) Filed in Color)

(51) Int. Cl.
*C12N 5/0789* (2010.01)
*C12N 5/078* (2010.01)
*C12Q 1/68* (2006.01)
*A61K 35/28* (2015.01)
*G01N 1/10* (2006.01)
*G01N 33/569* (2006.01)

(56) References Cited

U.S. PATENT DOCUMENTS

| | | | | |
|---|---|---|---|---|
| 5,350,836 | A | * | 9/1994 | Kopchick et al. ............ 530/399 |
| 5,827,742 | A | | 10/1998 | Scadden |
| 2005/0255327 | A1 | | 11/2005 | Chaney et al. |
| 2007/0020754 | A1 | * | 1/2007 | Yuge et al. .................. 435/325 |
| 2007/0190646 | A1 | | 8/2007 | Discher et al. |
| 2009/0041825 | A1 | | 2/2009 | Kotov et al. |
| 2010/0015709 | A1 | | 1/2010 | Rehfeldt et al. |
| 2010/0227399 | A1 | * | 9/2010 | Funaki .................... A01N 1/02 435/366 |
| 2010/0248361 | A1 | | 9/2010 | Lasky et al. |
| 2010/0273259 | A1 | | 10/2010 | Alexander et al. |
| 2011/0020930 | A1 | | 1/2011 | Wise et al. |

OTHER PUBLICATIONS

Lukas et al (2009). Identification of Novel Classes of Protein Kinase Inhibitors Using Combinatorial Peptide Chemistry Based on Functional Genomics Knowledge. J Med. Chem, v42(5), p. 910-919.*
Straight et al. (2003). Dissecting Temporal and Spatial Control of Cytokinesis with a Myosin II Inhibitor. Science, v299(5613), p. 1743-1747.*
Cheung et al. (2002). A small-molecule inhibitor of skeletal muscle myosin II. Nature Cell Biology, v4(1), p. 83-88.*
Ostap (2002). 2,3-Butanedione monoxime (BDM) as a myosin inhibitor. J Muscle Res Cell Motil, v23(4), p. 305-308.*
Saito et al. (1994). Mycalolide B, a Novel Actin Depolymerizing Agent. JBC, v269, p. 29710-29714.*
Boitano et al. (2010). Aryl Hydrocarbon Receptor Antagonists Promote the Expansion ofHuman Hematopoietic Stem Cells. Science, v329, p. 1345-1348.*
Kim et al. (2006). Novel Compound 2-Methyl-2H-pyrazole-3-carboxylic Acid (2-methyl-4-o-tolylazo-phenyl)-amide (CH-223191) Prevents 2,3,7,8-TCDD-Induced Toxicity by Antagonizing the Aryl Hydrocarbon Receptor. Molecular Pharmacology, v69(6) p. 1871-1878.*
Murray et al. (2010). Antagonism of Aryl Hydrocarbon Receptor Signaling by 6,2',4'-Trimethoxyflavone. JPET, v332(1), p. 135-144.*
Walker et al. (2010). Non-muscle myosin II regulates survival threshold of pluripotent stem cells. Nature Communications, v1(71), PMC manuscript, 18 pages.*
Reed et al. (2009). In Situ Mechanical Interferometry of Matrigel Films. Langmuir, v25, p. 36-39.*
Ng et al. (2008). A Perfusable 3D Cell—Matrix Tissue Culture Chamber for In Situ Evaluation of Nanoparticle Vehicle Penetration and Transport. Biotechnol Bioeng. v99(6), p. 1490-1501.*
Hughes et al. (2010). Matrigel: A complex protein mixture required for optimal growth of cell culture. Proteomics, v10, p. 1886-1890.*
Bao et al.(2005). Vertebrate Nonmuscle Myosin II Isoforms Rescue Small Interfering RNA-induced Defects in COS-7 Cell Cytokinesis. JBC, v280(20), p. 19594-19599.*
Engler et al. (2006). Matrix Elasticity Directs Stem Cell Lineage Specification. Cell, v126, p. 677-689 plus 11 page appended supplement.*
Villaron et al. (2004). Mesenchymal stem cells are present in peripheral blood and can engraft after allogeneic hematopoietic stem cell transplantation. Haematologica, v89, p. 1421-1427.*
Benjamin et al. (1998). A plasticity. window for blood vessel remodelling is defined by pericyte coverage of the preformed endothelial network and.is regulated by PDGF-B and VEGF. Development 125:1591-1598.*

Vukicevic et al. (1996). Induction of nephrogenic mesenchyme by osteogemc protein 1 (bone morphogenetic protein 7). PNAS USA 93:9021-9026.*
Massague et al. (1987). The TGF-beta Family of Growth and Differentiation Factors. Cell 49:437-8.*
Pilbeam et al. (1993). Comparison of the Effects of Various Lengths of Synthetic Human Parathyroid Hormone-Related Peptide (hPTHrP)of Malignancy on Bone Resorption and Formation in Organ, Culture. Bone 14:717-720.*
Skolnick et al. (2000). From genes to protein structure an.d function: novel applications of computational approaches in the genomic era. Trends in Biotech. 18:34-39.*
Bork (2000). Powers and Pitfalls in Sequence Analysis: The •70% Hurdle. Genome Research 10:398-400.*
Doerks et al. (1998). Protein annotation: detective work for function prediction. Trends in Genetics 14:248-250.*
Smith et al. (1997). The challenges of genome sequence annotation or "The devil is in the details". Nature Biotechnology 15:1222-1223.*
Brenner (1999). Errors in Genome Annotation. Trends in Genetics 15:132-133.*
Bork et al. (1996). Go hunting in sequence databases but watch out for traps. Trends in Genetics 12:425-427.*
Vukicevic et al. (1992). Identification of multiple active growth factors in basement membrane Matrigel suggests caution in interpretation of cellular activity related to extracellular matrix components. Exp Cell Res, v202(1), p. 1-8.*
Grattoni et al. Rheology and Permeability of Crosslinked Polyacrylamide Gel. Journal of Colloid and Interface Science (2001), v240, p. 601-607.*
Huang et al. Common Features of Megakaryocytes and Hematopoietic Stem Cells: What's the Connection? Journal of Cellular Biochemistry (2009), v107, p. 857-864.*
Introduction to Flow Cytometry (2002), 52 pages plus front matter.*
Adamo et al., "Biomechanical forces promote embryonic haematopoiesis." 2009, Nature, 459(7250): 1131-1135.
Calvi et al., "Osteoblastic cells regulate the haematopoietic stem cell niche." 2003, Nature 425:841-846.
Canman et al., "Inhibition of Rac by the GAP activity of centralspindlin is essential for cytokinesis." 2003, Science, 322: 1543-1546.
Carrion et al., "Recreating the perivascular niche ex vivo using a microfluidic approach." 2010, Biotechnol Bioeng.107(6):1020-8.
Chen et al., "The May-Hegglin anomaly gene MYH9 is a negative regulator of platelet biogenesis modulated by the Rho-ROCK pathway." 2007, Blood, 110:171-179.
Conti et al., "Defects in cell adhesion and the visceral endoderm following ablation of nonmuscle myosin heavy chain II-A in mice." 2004, J Biol Chem, 279:41263-41266.
Eckly et al., 2010, "Proplatelet formation deficit and megakaryocyte death contribute to thrombocytopenia in Myh9 knockout mice." J Thromb Haemost. 8(10):2243-51.
Engler et al., "Matrix elasticity directs stem cell lineage specification." 2006, Cell, 126:677-689.
Eto et al., "Megakaryocytes derived from embryonic stem cells implicate CaIDAG-GEFI in integrin signaling." 2002, Proc Natl Acad Sci USA, 99:12819-12824.
Holst et al., "Substrate elasticity provides mechanical signals for the expansion of hemopoietic stem and progenitor cells." 2010, Nat Biotechnol, 28(10): 1123-1128.
Huang and Cantor, "Common features of megakaryocytes and hematopoietic stem cells: what's the connection?" 2009, J Cell Biochem, 107(5): 857-864.
Klein et al., "Cell-cycle control by physiological matrix elasticity and in vivo tissue stiffening." 2009, Curr Biol, 19(18): 1511-1518.
Maupin et al., "Differential localization of myosin-II, isozymes in human cultured cells and blood cells." 1994, J Cell Sci, 107:3077-3090.
Nilsson et al., "Immunofluorescence characterization of key extracellular matrix proteins in murine bone marrow in situ." 1998, J Histochem Cytochem, 46:371-377.

(56) References Cited

OTHER PUBLICATIONS

Pallotta et al., "Bone marrow osteoblastic niche: a new model to study physiological regulation of megakaryopoiesis." 2009, PLoS ONE, 4:e8359.

Shin et al., "Myosin-II inhibition and soft 2D matrix maximize multinucleation and cellular projections typical of platelet-producing megakaryocytes." 2011, Proc Natl Acad Sci USA., 108(28): 11458-11463.

Smith et al., "Micropipette aspiration of guinea pig megakaryocytes: absence of fragmentation and dependence on maturation stage." 1989, Blood, 73:1570-1575.

Straight et al., "Dissecting temporal and spatial control of cytokinesis with a myosin II Inhibitor." 2003, Science, 299:1743-1747.

Winer et al., "Bone marrow-derived human mesenchymal stem cells become quiescent on soft substrates but remain responsive to chemical or mechanical stimuli." 2009, Tissue Eng Part A, 15:147-154.

Zang et al., "On the role of myosin-II in cytokinesis: division of Dictyostelium cells under adhesive and nonadhesive conditions." 1997, Mol Biol Cell, 8:2617-2629.

\* cited by examiner

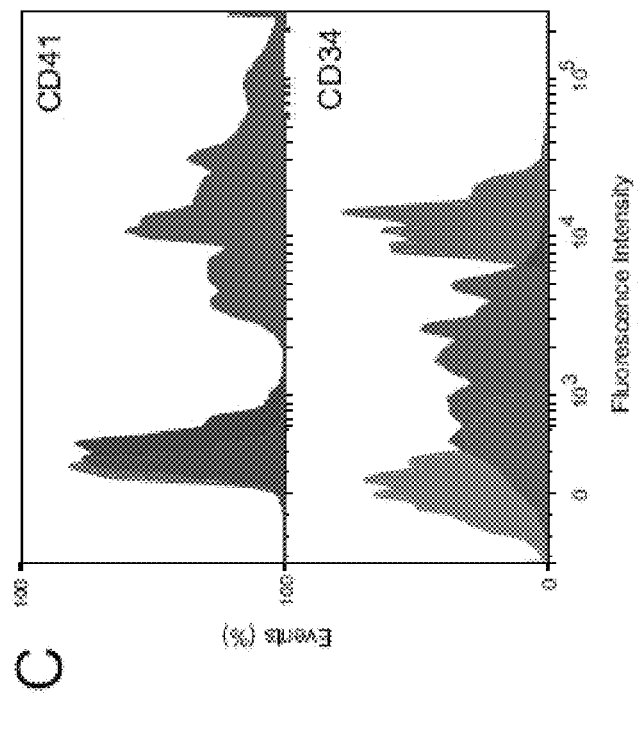
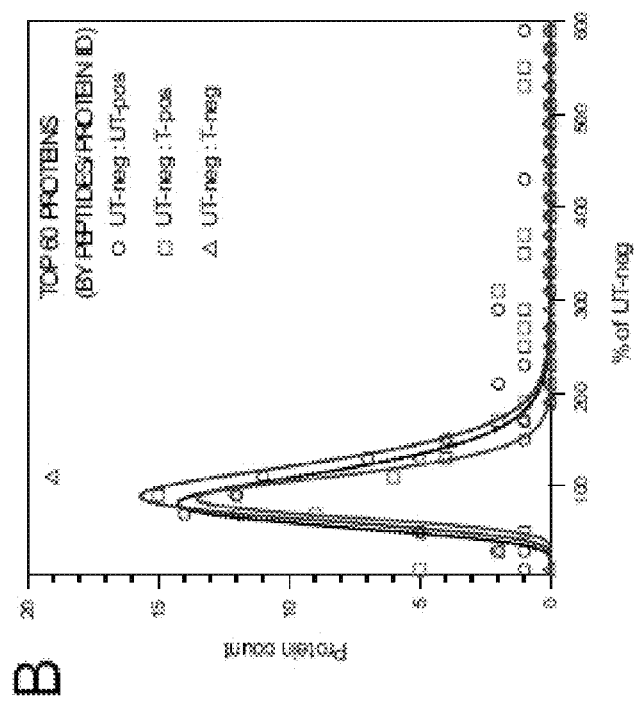
Figure 13 (continued)

Figure 21

A. Upregulated genes in both Bleb-treated CD34+ cells and fresh HSC/MPP

| Gene Symbol | MPP | HSC | CD34+ Bleb |
|---|---|---|---|
| EMCN | 1.79 | 2.76 | 1.20 |
| GPR125 | 2.36 | 2.73 | 1.28 |
| PROM1 | 2.16 | 2.58 | 1.13 |
| CRHBP | 2.20 | 2.37 | 1.24 |
| HLF | 1.78 | 2.26 | 1.42 |
| HTR1F | 1.91 | 2.24 | 1.04 |
| CD34 | 2.03 | 2.08 | 1.07 |
| LMCH1 | 1.57 | 2.07 | 0.55 |
| BAALC | 1.33 | 2.07 | 0.77 |
| GSTM5 | 1.71 | 2.07 | 0.44 |
| PFN2 | 1.93 | 2.05 | 0.13 |
| RBPMS | 1.64 | 2.02 | 1.14 |
| SPINK2 | 1.49 | 1.99 | 0.96 |
| KLHL3 | 1.71 | 1.88 | 0.87 |
| MPZL2 | 1.00 | 1.81 | 0.98 |
| NPPED2 | 1.13 | 1.80 | 0.83 |
| CALCRL | 1.17 | 1.77 | 0.72 |
| AKR1C3 | 1.31 | 1.70 | 0.72 |
| MYO5C | 1.39 | 1.61 | 0.81 |
| CD200 | 0.93 | 1.59 | 0.81 |
| ERG | 1.36 | 1.57 | 0.63 |
| C5orf23 | 1.30 | 1.55 | 0.85 |
| FLJ2RB2 | 1.33 | 1.52 | 0.86 |
| SELL | 1.26 | 1.48 | 0.66 |
| TFPI | 1.06 | 1.48 | 0.41 |
| NPR3 | 1.14 | 1.48 | 0.90 |
| BST2 | 0.92 | 1.47 | 0.58 |
| MYCN | 1.42 | 1.44 | 0.86 |
| HOXA9 | 1.17 | 1.40 | 0.82 |
| ELK3 | 0.96 | 1.39 | 0.57 |
| TAB3P1 | 1.25 | 1.37 | 0.35 |
| PMS2L2 | 1.30 | 1.37 | 0.41 |
| TNFSF4 | 1.29 | 1.36 | 0.86 |
| ITGA9 | 0.95 | 1.34 | 0.67 |
| MERTK | 0.77 | 1.29 | 0.52 |
| NRP1 | 1.03 | 1.29 | 0.51 |
| KIAA0125 | 0.95 | 1.28 | 0.66 |

| Gene Symbol | MPP | HSC | CD34+ Bleb |
|---|---|---|---|
| HOXA4 | 0.48 | 1.26 | 0.39 |
| MYCT1 | 0.78 | 1.25 | 0.38 |
| FLT3 | 1.18 | 1.23 | 0.69 |
| PMS2L2 | 1.18 | 1.22 | 0.43 |
| PLS3 | 0.48 | 1.16 | 0.49 |
| BCL11A | 1.01 | 1.14 | 0.47 |
| NUP731 | 1.27 | 1.07 | 0.54 |
| DAPK1 | 0.88 | 1.06 | 0.81 |
| ETS2 | 1.00 | 1.05 | 0.69 |
| SSBP2 | 0.79 | 1.03 | 0.48 |
| DSG2 | 0.73 | 1.02 | 0.38 |
| GATA3 | 0.67 | 1.02 | 0.38 |
| MPO2 | 0.95 | 1.00 | 0.73 |
| BCL9 | 0.45 | 0.99 | 0.50 |
| KIAA0087 | 1.18 | 0.98 | 0.81 |
| FLJ1710 | 0.45 | 0.96 | 0.45 |
| GUCY2A3 | 0.53 | 0.92 | 1.06 |
| PTPRC | 0.41 | 0.90 | 0.44 |
| ERMAP | 0.49 | 0.89 | 0.55 |
| PLEKHA5 | 0.58 | 0.84 | 0.47 |
| FHL1 | 0.47 | 0.81 | 0.43 |
| IQGAP2 | 0.69 | 0.76 | 0.53 |
| UCHL1 | 0.59 | 0.75 | 0.33 |
| ANKRD28 | 0.55 | 0.65 | 0.88 |
| CD164 | 0.53 | 0.74 | 0.55 |
| ZNRF1 | 0.77 | 0.74 | 0.42 |
| F2RL1 | 0.36 | 0.73 | 0.48 |
| TM4SF1 | 0.61 | 0.69 | 0.73 |
| CEP70 | 0.62 | 0.66 | 0.73 |
| MLLT3 | 0.41 | 0.66 | 0.38 |
| ING4 | 0.53 | 0.60 | 0.36 |
| CLGN | 0.03 | 0.58 | 0.41 |
| HOXA5 | 0.99 | 0.55 | 0.36 |
| GNAI1 | 0.35 | 0.53 | 0.38 |
| SCHIP1 | 0.44 | 0.52 | 0.57 |
| SCARB2 | 0.36 | 0.46 | 0.51 |
| DEPDC6 | 0.69 | 0.41 | 0.68 |

B. Genes downregulated in both Bleb-treated CD34+ cells and fresh HSC/MPP

C. Genes showing correlations between Bleb-treated CD34+ cells and fresh HSC but not MPP

| Gene Symbol | MPP | HSC | CD34+ Bleb |
|---|---|---|---|
| TMEM45A | -0.84 | -0.54 | -0.32 |
| ANPEP | -0.39 | -0.56 | -0.61 |
| RAB38 | -1.18 | -0.58 | -0.36 |
| NGLL1 | -0.63 | -0.63 | -0.37 |
| GABPB2 | -1.03 | -0.74 | -0.35 |
| PAICS | -0.64 | -0.79 | -0.37 |
| LMO4 | -0.43 | -0.79 | -0.35 |
| STAU2 | -1.21 | -0.81 | -0.36 |
| SPRY2 | -1.10 | -0.94 | -0.49 |
| SCN9A | -1.21 | -1.05 | -0.61 |
| CD38 | -1.31 | -1.35 | -0.56 |
| LEF1 | -1.16 | -1.44 | -0.57 |
| CCL5 | -1.44 | -1.53 | -0.53 |
| LRP12 | -1.97 | -1.56 | -0.45 |
| BCL2L11 | -1.25 | -1.64 | -0.47 |
| FOS | -2.03 | -1.68 | -0.85 |
| PARP8 | -1.64 | -1.83 | -0.93 |
| GPR183 | -1.78 | -2.08 | -1.18 |
| SAMHD1 | -2.54 | -2.17 | -0.81 |
| EGR2 | -2.22 | -2.38 | -1.24 |
| ITGA2B | -2.09 | -2.40 | -0.36 |
| GGH | -2.68 | -2.70 | -0.41 |
| ALOX5AP | -3.41 | -3.48 | -1.62 |
| HPGD | -3.29 | -3.64 | -1.17 |
| FYB | -3.89 | -3.68 | -2.67 |
| CD226 | -3.82 | -3.96 | -1.13 |
| ITGB3 | -4.42 | -4.03 | -0.54 |
| MMOA | -4.76 | -4.60 | -0.36 |
| CPA3 | -3.59 | -5.80 | -4.16 |

| Gene Symbol | MPP | HSC | CD34+ Bleb |
|---|---|---|---|
| CFH | 0.14 | 0.94 | 1.17 |
| MREG | 0.23 | 0.81 | 0.38 |
| LRBA | 0.30 | 0.78 | 0.41 |
| NEK3 | 0.25 | 0.70 | 0.35 |
| VAV3 | 0.21 | 0.60 | 0.47 |
| ALDH1A2 | 0.02 | 0.46 | 0.50 |
| ANGPT1 | 0.19 | 0.45 | 0.47 |
| SYPL1 | 0.14 | 0.44 | 0.36 |
| ATP1B1 | 0.24 | 0.36 | 0.77 |
| MYH10 | 0.11 | 0.35 | 0.61 |
| MME | 0.31 | 1.06 | 0.50 |

Figure 21 (continued)

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Chemically synthesized

<400> SEQUENCE: 1
gccggggatg gcgccgacga agagg                                   25

<210> SEQ ID NO 2
<211> LENGTH: 25
<212> TYPE: DNA
<213> ORGANISM: Artificial Sequence
<220> FEATURE:
<223> OTHER INFORMATION: Chemically synthesized

<400> SEQUENCE: 2
cctcttcgtc ggcgccatcc ccggc                                   25

BIOREACTOR FOR ISOLATION OF RARE CELLS AND METHODS OF USE

STATEMENT REGARDING FEDERALLY SPONSORED RESEARCH OR DEVELOPMENT

This invention was made with government support under NIH PO1DK032094 awarded by the National Institutes of Health (NIH). The government has certain rights in the invention.

CROSS-REFERENCE TO RELATED APPLICATIONS

The present application claims priory to U.S. Provisional Patent Application No. 61/601,364, filed Feb. 21, 2012, the entire disclosure of which is incorporated by reference herein as if set forth herein in its entirety.

BACKGROUND OF THE INVENTION

Hematopoiesis is the formation of blood cells that occurs in the bone marrow, spleen, liver, and lymph nodes. All blood cells (erythrocytes, platelets, white blood cells, etc.) ultimately originate from hematopoietic stem cells (HSCs). Through differentiation into different progenitor cells, HSCs have the unique ability to give rise to all of the different mature blood cells. This property has led to intense efforts to isolate, produce, and culture HSCs, as these cells would have great use in the treatment of a wide variety of diseases and disorders.

HSCs give rise to all blood cell types in an adult and maintain this ability after asymmetric division. To maintain such self-renewal throughout the life of an organism, HSCs are often quiescent and found in specialized microenvironments or niches of the bone marrow. A number of HSC niche models and soluble signals that regulate HSC maintenance have been described (Kiel et al., 2008, Nat Rev Immunol, 8(4): 290-301), but there remains a need to understand physical aspects of the niche, including forces imposed or generated by HSCs. Externally imposed shear stresses are known to regulate embryonic hematopoiesis (Adamo et al., 2009, Nature, 459(7250): 1131-1135), and extensional elastic properties of a tropoelastin matrix reportedly influence HSC expansion (Holst et al., 2010, Nat Biotechnol, 28(10): 1123-1128). However, it remains unclear what molecules integrate physical attributes of matrices and microenvironments to mechanically regulate HSC fates.

Platelets, or thrombocytes, are small cellular fragments which are important for the formation of blood clots. These platelets are formed through the fragmentation of megakaryocytes (MKs). MKs are large blood cells found within the bone marrow and are characterized by having a unique lobed structure and by having several copies of cellular DNA. These unique properties of MKs occur because these cells replicate their DNA without cytokinesis (division) in a process called endomitosis. Once a MK matures, it is fragmented into many platelets which go into the blood circulation. Reduced platelet count, known as thrombocytopenia, can occur in a number of disease processes. Subjects with reduced platelets can have trouble clotting, have abnormal bruising, and experience general fatigue and weakness.

Despite research efforts, there is currently no known strategy to cheaply and easily isolate and culture rare blood cells, including HSCs and MKs. Thus, there is a need in the art for a bioreactor that can isolate rare blood cells, and for methods that isolate, use and assay rare blood cells. The present invention addresses these unmet needs in the art.

SUMMARY OF THE INVENTION

In one embodiment, the present invention provides an apparatus for the isolation of non-dividing cells from a cell population. The apparatus comprises a substrate layer on at least one surface of the apparatus, where the substrate layer includes at least one composition comprising at least one anti-contractility agent for reducing cell contractility when a cell population is in contact with the substrate layer. In one embodiment, the composition further comprises at least one compound selected from the group consisting of an aryl-hydrocarbon receptor antagonist and a growth factor. In one embodiment, the non-dividing cells are rare blood cells selected from the group consisting of hematopoietic stem cells, polyploid megakaryocytes, polyploid non-megakaryocytes, granulocyte-macrophage progenitors, and erythroid progenitors. In one embodiment, the substrate layer is a soft substrate having a low stiffness of about 0.3 kPa to 2 kPa. In another embodiment, the anti-contractility agent inhibits the function of myosin-II.

In one embodiment, the at least one composition is embedded within the substrate layer. In one embodiment, the surface of the substrate layer is coated with at least one protein selected from the group consisting of collagen, fibronectin, laminin, and vitronectin.

The present invention also provides a bioreactor for the isolation of non-dividing cells from a cell population. The bioreactor comprises a housing comprising a hollow tube, where the hollow tube includes two openings and an inner surface to form a passage therethrough, a substrate layer conjugated to at least a portion of the inner surface of the tube; and gas permeable caps removably attached to the tube openings. The substrate layer comprises at least one composition selected from the group consisting of an anti-contractility agent, an aryl-hydrocarbon receptor antagonist, and a growth factor.

In one embodiment, the non-dividing cells are rare blood cells selected from the group consisting of hematopoietic stem cells, polyploid megakaryocytes, polyploid non-megakaryocytes, granulocyte-macrophage progenitors, and erythroid progenitors. In one embodiment, the substrate layer is a soft substrate having a low stiffness of about 0.3 kPa to 2 kPa. In one embodiment, the anti-contractility agent inhibits the function of myosin-II. In one embodiment, the composition is embedded within the substrate layer. In one embodiment, the surface of the substrate layer is coated with at least one protein selected from the group consisting of collagen, fibronectin, laminin, and vitronectin.

In one embodiment, the bioreactor is converted into a syringe conformation, wherein syringe confirmation comprises a sterile tip attached to one end of the tube and a plunger unit inserted into the cavity through the opposite end of the tube.

The invention further provides a method of isolating at least one non-dividing cell from a cell population. The method comprises comprising the steps of obtaining a population of cells from a subject; culturing the cells within an apparatus having a substrate layer such that the cells are in contact with the substrate layer, where the substrate layer includes at least one composition selected from the group consisting of an anti-contractility agent, an aryl-hydrocarbon receptor antagonist and a growth factor; capturing non-viable cells from the apparatus; and removing the non-viable cells from the population of cells, thereby isolating at least one non-dividing cell from a cell population.

In one embodiment, the non-dividing cells are rare blood cells selected from the group consisting of hematopoietic stem cells, polyploid megakaryocytes, polyploid non-megakaryocytes, granulocyte-macrophage progenitors, and erythroid progenitors. In one embodiment, the substrate layer is a soft substrate having a low stiffness of about 0.3 kPa to 2 kPa. In one embodiment, the anti-contractility agent inhibits the function of myosin-II. In one embodiment, the at least one composition is embedded within the substrate layer. In one embodiment, the surface of the substrate layer is coated with at least one protein selected from the group consisting of collagen, fibronectin, laminin, and vitronectin.

In one embodiment, the at least one isolated non-dividing cell is used to program the outcome of blood cell transplantation in a subject.

In another embodiment, the at least one isolated non-dividing cell is used to perform at least one function selected from the group consisting of early recovery of platelet count, clearance of granulocyte-macrophage progenitors, maintenance of long term hematopoietic stem cell activity and red blood cell generation.

In another embodiment, the at least one isolated non-dividing cell is assayed for the presence of at least one type of rare blood cell by detecting the presence of at least one specific biomarker associated with the at least one type of rare blood cell, where detecting the presence of at least one specific biomarker comprises the use of at least one detection method selected from the group consisting of qPCR, microarray, western blot and mass spectrometry. In one embodiment, the at least one type of rare blood cell is megakaryocytes and the at least one specific biomarker is at least one selected from the group consisting of myosin regulatory light chain 12A, gelsolin, vinculin, filamin A, talin 1, actin, tropomyosin alpha-4 chain, vimentin, MYH9, MYL6, tubulin alpha 1A, plastin 2, tubulin beta 2C, actin-related protein 2/3 complex 4, transgelin 2, moesin, plectin, profiling 1, stathmin, cofilin 1, and alpha-actinin-4. In another embodiment, the at least one type of rare blood cell is hematopoietic stem cells and the at least one specific biomarker is at least one selected from the group consisting of non-muscle myosin IIB (MYH10), CD34, THY1, PROM1, EMCN, HLF, MNDA, MME, CPA3, ALOX5AP, and GPR126.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

The patent or application file contains at least one drawing executed in color. Copies of this patent or patent application publication with color drawing(s) will be provided by the Office upon request and payment of the necessary fee.

FIG. 1A through FIG. 1D, illustrates that myosin affects MK maturation and cell fragmentation. FIG. 1A depicts an in vivo scheme of MK-poiesis and platelet fragmentation in bone marrow. FIG. 1B depicts the in vitro model of MK maturation and platelet fragmentation by myosin inhibition and micropipette aspiration on CD34+-derived cultures. FIG. 1C illustrates that myosin inhibition by blebbistatin accelerates CD41+ MK polyploidization by depicting representative flow cytometry plots for ploidy analysis (Upper), and dose-dependence (Lower). Absolute values were normalized to $10^4$ initial cell input (n≥4 donors, ±SEM). FIG. 1D illustrates that myosin inhibition increases membrane extension and fragmentation in micropipette aspiration by depicting representative fragmentation within seconds (Upper) after 30 min of 20 μM blebbistatin treatment and aspiration ΔP=1.4 kPa. Aspiration length vs. effective cortical tension (Lower) with median results shown.

FIG. 2A through FIG. 2E, depicts the effects of matrix elasticity and ligand density on MK polyploidy. All MK polyploid cell numbers were scaled to $10^4$ initial cell input (n≥3 donors; ±SEM). FIG. 2A illustrates that soft (0.3 kPa) matrices always facilitate MK polyploidization on 2 ng/cm$^2$ (low) collagen gels. Tukey's HSD Test indicates P<0.05 for all pairs except 0.3 kpa 0 μM vs. 34 kpa 20 μM. FIG. 2B depicts, on a range of collagen concentrations, ratios of polyploid MK numbers for soft (0.3 kPa) versus stiff (34 kPa) matrices fit to standard dose-response curves: untreated and blebbistatin-treated IC50~20, 1,000 ng/cm$^2$, respectively (Hill coefficients ~−1.5, −2.0 respectively). FIG. 2C depicts a graph illustrating cell adhesion on soft and stiff matrices after 3 d cell culture±blebbistatin. *P<0.05 for 0.3 kPa vs. 34 kPa untreated. FIG. 2D depicts a graph illustrating polypoid MK numbers on stiff gels cultured on a range of collagen concentrations. Dose-response curves are shown for untreated ($EC_{50}$~200 ng/cm$^2$, Hill coefficient=1.0) and blebbistatin-treated cells (IC50~0.3 ng/cm$^2$, Hill coefficient=−1.3). Cartoon depicts effects on cell adhesion and division. FIG. 2E illustrates proplatelet formation with different gels. (Left) Representative images with F-actin. (Scale bar, 5 μm.) (Right) Quantitation of branch length from cell body. (>50 measurements for each group, n≥2 donors). 3D matrices are soft with E~1 to 3 kPa. P values are reported from Tukey's HSD test.

FIG. 3A and FIG. 3B, illustrates that sustained inhibition of myosin-II blocks cytokinesis. FIG. 3A is a graph illustrating that generation of polyploid cells is exponential in duration of exposure to 20 μM blebbistatin with doubling time of 18.2 h. All values were scaled to an initial cell input of $10^4$ cells (n=3, ±SEM). FIG. 3B depicts live cell imaging that shows reversal of cytokinesis with blebbistatin for ~80% of cells observed; without drug, all cells divided. (Scale bar, 10 μm.)

FIG. 4A through FIG. 4C, illustrates that phosphorylation of NMM-IIA regulates polyploidization. FIG. 4A is a graph depicting MS analyses of phospho-S1943 in primary cells. Each pS1943 signal was normalized first to total NMM-IIA signal, which was then normalized to values from CD41+ sorted cells (untreated), and averaged between experiments (n=2). Ion current of pS1943 in CD41+ is ~1% of total NMM-IIA signal. *P<0.05 from one-way ANOVA with Tukey's HSD test. FIG. 4B illustrates that blebbistatin treatment leads to overall reduction of pTyr levels under both unstimulated and pervanadate (100 μM)-stimulated conditions as assessed by flow cytometry (Upper). IP of NMM-IIA from lysates of cells treated with pervanadate±blebbistatin, followed by immunoblot of pTyr and densitometry (Lower) shows reduced pTyr levels in NMM-IIA head (150 kDa) region (n=3, ±SEM). FIG. 4C illustrates that NMM-IIA head pTyr mutant (Y277F) increases polyploidization. COS cells were transfected as indicated±pretransfection with NMM-IIB siRNA. Cultured cells were stained with Hoechst 33342 to quantify polyploidy (≥8 N) by flow cytometry (n≥3, ±SEM).

FIG. 6A through FIG. 6D, is a series of images characterizing platelets derived from myosin-inhibited MKs. FIG. 6A illustrates the number of platelets per CD41$^+$ cell. (Left) NSG mice transplanted intratibially with human-CD34$^+$-derived cells that were pretreated ex vivo with blebbistatin for 3 d (versus untreated cells) show enhanced circulating human platelets. ($P<0.0001$; n=9 mice±SEM). (Right) MKs exposed to blebbistatin (20 μM for 3 d, then 3 d of no drug) show more in vitro platelets ($P<0.05$; n=5 donors, ±SEM). (B) Similar immunostaining of microtubules in the various MK-derived platelets (n=3 donors). FIG. 6C is a series of images depicting similar adhesion and filipodia formation of various MK-derived platelets on collagen-I upon thrombin (1 U/mL) stimulation. (n=3 donors). FIG. 6D illustrates that platelets derived from blebbistatin-exposed MKs show normal PAC-1 binding with thrombin (1 U/mL). Tirofiban (10 μM) selectively antagonizes αIIbβ3 and inhibits as expected. Representative flow cytometry plots from three experiments. (Scale bars, 5 μm.)

FIG. 7A through FIG. 7D, illustrates that down-regulation of myosin leads to increased multi-nucleation in different cell systems. FIG. 7A depicts a dose-response curve of THP-1 cell number with different ploidy shows increased polyploid cell number by blebbistatin. FIG. 7B depicts a dose-response curve of COS-1 shows increased polyploidy by blebbistatin. Absolute cell number was scaled by 10,000 initial cell input before drug treatment. FIG. 7C illustrates that MIIA transcript knock-down leads to polyploidization in THP-1 cells. THP-1 cells were transduced with MIIA shRNA by lentiviral vector. The THP-1 MIIA knock-down cells were previously established (Tsai et al., 2008, J Cell Biol, 180:989-1003). Cells were cultured for 1 wk before ploidy analysis under microscope. Blue, nucleus (Hoechst 33342); red, dead cells (propidium iodide). (Scale bar, 10 μm.) DNA content was measured under a microscope and integrated nuclear intensity was calculated, followed by normalization against median value. Data were fit into bimodal Gaussian distribution for untreated cells, given that these cells consist of diploid and tetraploid. At least 100 cells were analyzed for each group. FIG. 7D illustrates that MIIB transcript knock-down by siRNA transfection leads to polyploidization in COS-1 cells. siRNA was transfected and incubated for 3 d. Green, NMM-IIB; purple, Lamin A/C; blue, Hoechst 33342. (Scale bar, 10 μm.) At least 50 cells were analyzed for each group to measure mean NMM-IIB intensity.

FIG. 8A and FIG. 8B, depicts the results of experiments using an in vitro model of MK maturation and platelet fragmentation by myosin inhibition and micropipette aspiration. FIG. 8A depicts the complete micropipette aspiration data from: untreated (n=14), 20 μM blebbistatin unfragmented (n=10) and fragmented (n=6) cells. Slopes indicate compliance in units of (mN/m)$^{-1}$. Untreated cells have median slope of 0.46±0.05, and cells treated at 20 μM and unfragmented have a slope of 3.79±0.84 ($P<0.0001$). Median fragmentation threshold is ~1 mN/m. FIG. 8B illustrates that primary MKs and MEG01 cells show cortical microtubule coil-like structures in micropipette aspiration. Cells were labeled with a very low and cell-viable dose of fluorescent BODIPY-Taxol (10 nM), which binds specifically to microtubules and not to soluble tubulin. Micropipette aspiration was followed by fluorescence imaging. Representative images are from at least five measurements per cell type. The initial microtubule extension rate measured by lengths of the fluorescent signal over time under aspiration (<10 kPa) is ~0.7 μm/min, consistent with previously reported values. (Scale bars, 10 μm.)

FIG. 9A through FIG. 9G, illustrates the characterization of myosin inhibited cells. FIG. 9A are images depicting the increased branching and fragmentation of COS-1 cells by myosin inhibition. Cells were plated on glass coverslips and incubated with or without blebbistatin for 24 h before fixation and staining for immunofluorescence microscopy. Representative images are shown, and the right image is a composite of two large images. For 0 μM: red, F-actin; green, NMM-IIB; blue, Lamin A/C. For 20 μM: a composite image of a cell with F-actin staining is shown. (Scale bar, 20 μm.) FIG. 9B is a graph depicting the quantification of average extension length from COS-1 cells with or without blebbistatin treatment. At least 50 measurements were made from two independent cell batches for each group (±SEM). $P<0.0001$. FIG. 9C is an image illustrating that cellular fragments from COS-1 cells generated by blebbistatin contain F-actin and NMMIIB (green). (Scale bar, 20 μm.) FIG. 9D is a series of images illustrating process extension and dynamics in COS cells. (Left) Immunofluorescence staining of NMM-IIB (green), F-actin (red), and α-tubulin (blue) of COS cell treated by blebbistatin. (Scale bar, 20 μm.) (Right) Live imaging of COS cell process extension during myosin inhibition. Image indicated every 25 min. (Scale bars, 20 μm.) FIG. 9E are images illustrating the visualization of lipid "demarcation" membrane in MKs and COS cells. (Scale bars, 5 μm for primary cells and 20 μm for COS cells.) FIG. 9F illustrates process extension dynamics of CD34$^+$-derived cells during myosin inhibition analyzed by live cell imaging. Time-lapse image sequences of a cell extending processes. (Scale bar, 10 μm.) FIG. 9G is a graph depicting the measurement of process length over time. Live imaging data were collected from 11 processes from five CD34$^+$-derived cells. Each projection length was measured manually and plotted over time. Mean elongation speed and average process length during the plateau phase were also quantified. Collapse was observed for some processes and more work is needed to determine whether this reflects dynamic instability of microtubules. No elongation was observed in untreated cells under the same culture condition.

FIG. 10A through FIG. 10C, illustrates the characterization of polyploidy cells derived by various treatments. FIG. 10A illustrates the effects of contractility inhibitors on MK polyploidization. Myosin is a highly efficacious target for MK polyploidization. (Upper Left) A model highlighting a direct role of myosin-II head ATPase in cell division compared with other known targets for cellular contractility. Inhibitors tested for each target. (Upper Right) Dose-response curves for MK polyploid cell number with different contractility drugs (n≥3 donors, ±SEM): Y-27632 (EC50=0.14 μM, Hill slope=1.0), reversine (EC50=0.5 μM, Hill slope=10.8), ML7 (IC50=1.04 μM, Hill slope=−4.74), and blebbistatin (EC50=7.6 μM, Hill slope=7.0). (Lower) Dose-response curves for MK cell number in 2 N (Left) and 4 N (Right). All IC50 and Hill slope values are the same as those of MK polyploid cell number curves, except for: 2 N reversine (IC50=0.26 µM, Hill slope=−2.0), 2 N ML7 (IC50=0.5 µM, Hill slope=−0.93), 4 N reversine (IC50=0.5 µM, Hill slope=−1.6), and 4 N ML7 (IC50=0.5 µM, Hill slope=−0.8). FIG. 10B illustrates the characterization of polyploid cells generated by myosin inhibition under different cell culture conditions. Viable non-MK polyploid cells can be generated by myosin inhibition. (Left) BM CD34$^+$ cells were cultured with or without G-CSF and treated with blebbistatin. (Right) Dose-response curves for CD41$^+$ MK and non-MK polyploid cell number after blebbistatin treatment for 3 d (n≥4 donors, ±SEM), showing same IC50 (7.6 µM) and Hill slope (7.0), but different maximal polyploid cell number values: SCF+Tpo CD41$^+$ (278), SCF+Tpo+G-CSF CD41$^+$ (141), SCF+Tpo CD41$^-$ (1), SCF+Tpo+G-CSF CD41$^-$ (352). All values were scaled to 10,000 initial cell input. FIG. 10C illustrates the characterization of CD6 Y polyploid cells generated by blebbistatin. (Left) Image of a polyploid CD61$^-$ flat, adherent cell (oval arrow) and a polyploid CD61$^+$ cell with proplatelets (pointed arrow). (Right) Polyploid CD41$^-$ cells that are generated and supported by G-CSF supplementation appear to be in a stage between early hematopoietic progenitors and granulocyte/macrophage progenitors, because they do not express the myeloid marker SIRPα, but they are CD34$^+$CD38$^+$ based on flow cytometry.

FIG. 11A through FIG. 11E, depicts the MS analysis of THP-1 proteins immunoprecipitated by anti-human NMM-IIA antibody. FIG. 11A illustrates the Coomassie-stained IP of myosin-9 for samples with and without blebbistatin treatment. Boxes show areas excised for MS analysis. Calibration against interpolated molecular weight standards showed that bands were detected at 18, 46, 62, 82, 108, and 132 (analyzed as gel section #4), 146 (gel section #3), ~250 (gel section #2), and ~425 kDa (extrapolated, gel section #1). FIG. 11B is a cartoon of the assembled myosin hexamer [a dimer of heavy chain, essential light chain (ELC), and regulatory light chain (RLC)]. One of the heavy chains has been annotated with the three chymotrypsin cleavage positions (triangles) that are consistent with gel and MS analyses. Resulting protein fragments have been labeled in yellow, green, blue, and purple: these annotations are used subsequently. FIG. 11C depicts the MS analysis of the four gel sections. Each tryptic peptide derived from myosin-9 that was detected is represented by a bar, with its width indicating sequence coverage (i.e., a range of amino acids) and its height showing the span of integrated ion currents in both blebbistatin-treated and untreated samples. FIG. 11D is a plot showing the breakdown of MS ion current per residue across the four myosin-9 fragments in the four gel sections. The ion currents have been normalized assuming that the second gel section contains whole myosin-9 (~230 kDa; i.e., all four protein fragments in 1:1:1:1 ratio). It is therefore suggested that gel section 1 contains aggregates of myosin-9, possibly with partial fragmentation of the head; gel section 2 contains intact myosin-9; gel section 3 contains green/blue fragment, plus potentially dimers of the green and blue fragments; and gel section 4 contains dimers of green and purple fragments. FIG. 11E depicts Western blot analysis of the IP experiment with staining for myosin heavy chain IIa and phosphotyrosine, showing the difference in the extent of tyrosine phosphorylation upon treatment with blebbistatin.

FIG. 12A through FIG. 12C, illustrates the role of posttranslational modifications of NMM-IIA. FIG. 12A is a graph showing quantitation of selected posttranslational modification residues from MS analyses of IP proteins with NMM-IIA antibody from THP-1 cells. FIG. 12B depicts representative flow cytometry plots showing ploidy of COS-1 cells transfected with the constructs. FIG. 12C depicts representative figures showing subcellular localization of COS-1 cells transfected with GFP-NMM-IIA or GFP-Y277F mutant construct. (Scale bars, 10 µm.)

FIG. 13A through FIG. 13D, illustrate flow cytometry and MS characterization of cells. FIG. 13A is a series of flow cytometry plots to isolate viable CD41$^+$ cells from untreated and blebbistatin-treated cells. The viable cell fraction was gated as 7-AAD$^-$ and Annexin-V$^-$ (Upper). This process was followed by gating CD41$^+$ (Lower) fraction and cells were sorted accordingly. FIG. 13B is a histogram showing the percentage of changes in normalized protein quantity, relative to the untreated CD41 (-ve) sample, for the top 60 proteins detected by LC-MS/MS (ordered by the number of peptides detected per protein). Label-free quantitation was performed with an optimized peptide selection protocol, normalized against peptides selected because they form invariant sets between samples. Points were fit to log-normal functions. In general, the distributions are quite narrow, about 100%, implying general similarities in protein expression between the four conditions. The comparison between the two CD41(-ve) samples shows the fewest outliers. FIG. 13C depicts flow cytometry analysis showing that CD41$^-$ contain more cells that are CD34hi cells (HSC/progenitors) than CD41$^+$ cells, which mostly consist of CD34int. Some CD41$^-$ cells consist of CD34$^-$ cells, which likely reflect differentiated granulocytes. FIG. 13D illustrates the validation of MS results. (Left) Heatmap showing quantification of validated proteins from flow cytometry analysis and quantitative immunofluorescence microscopy. Values from both the x and y axes indicate fold-changes from untreated CD41$^-$ cells. (Right) Correlation between validation results and corresponding results from MS quantitation. Dotted lines indicate 95% confidence bands. Linear fit, $R^2$=0.7.

FIG. 14A through FIG. 14E, depicts platelet and MK structure-function evaluations, including activation. FIG. 14A depicts the evaluation of MKs remaining in tibia 72 h after intrabone transplantation. No MK were identified in other organs. FIG. 14B depicts the evaluation of human CD41 and CD42b surface expression in MKs and MK-derived platelets by mean fluorescence intensity using specific antibodies and flow cytometry. Results from n=3 donors (±SEM) with paired t test for untreated vs. bleb-exposed MKs (Upper); and for in vitro untreated or blebbistatin-exposed MK generated vs. blood platelets (Lower) (*P<0.05). CD42b-to-CD41 ratio is also plotted for both MKs and platelets (P=not significant, ns). FIG. 14C shows that in vitro platelets from blebbistatin-exposed MKs show normal adhesion, spreading, stress fibers, lamellipodia, and filopodia on fibrinogen upon thrombin (1 U/mL) stimulation. Rhodamine-phalloidin stains F-actin but antihuman-CD61 is used to confirm platelets (from n=3 donors). (Scale bars, 5 µm.) FIG. 14D illustrates that polyploid MKs exposed to blebbistatin show normal adhesion and stress fiber and lamellipodia formation on fibrinogen upon thrombin stimulation. Representative images from n=3 donors are shown. (Scale bar, 10 µm.) FIG. 14E depicts the evaluation of activation with human P-selectin (CD62P) expression on in vivo-derived human CD41$^+$ platelet-like particles after MK transplantation into NSG mice. P-selectin is also known as platelet activation-dependent granule to external membrane protein. Platelets were isolated from transplanted NSC mice, and activated by 20 µM ADP, 1 µM PMA, or in combination with 20 U/mL thrombin plus $Mg^{2+}$ and $Ca^{2+}$. Human P-selectin level after agonist stimulation was specifically evaluated by flow cytometry using specific antibodies against human CD41-APC, human P-selectin-FITC, and mouse CD41-PE. Only human CD41$^+$ fraction from xenograft blood samples was analyzed for human P-selectin expression (n=3 donors). One-way ANOVA P<0.0005 and significant P values are reported from Tukey's HSD test: P<0.05 for all pair-wise test between resting versus stimulated conditions of untreated MK-platelet, bleb-exposed MK-platelet, and blood platelet (n=3 donors for each of MK-derived platelets and blood platelets).

FIG. 15A through FIG. 15C, illustrates that myosin-II-II contributes to various cellular processes in hematopoiesis and its inhibition enriches for LT-HSCs. FIG. 15A is a cartoon that illustrates that NMM-II inhibition regulates biophysical aspects of adult hematopoiesis, including cytokinesis upon cytokine stimulation, matrix elasticity sensing, and membrane elasticity with sensitivity to shear. FIG. 15B is a series of plots that show that myosin inhibition by Bleb enriches for LT-HSCs. An experimental scheme and representative flow cytometry plots for HSC/P subpopulation analysis and dose-dependence graph for 2N cells. 15.6±4.1 fold enrichment by 20 µM Bleb. Absolute values were normalized to 104 initial cell input and fit to dose-response curves: CPP and MPP IC50=~10.5 µM, Hill coefficient=~6.5; HSC mean=646±77 (n≥4 donors, ±SEM). FIG. 15C shows that Bleb-treated CD34$^+$ cells show a gene expression profile that is close to that of fresh HSC/MPP. Boxes indicate genes that are either down or upregulated in Bleb-treated CD34$^+$ cells and HSC/MPP.

FIG. 16A illustrates microarray profiling of transcripts in cells cultured with or without Bleb treatment. CD34$^+$-derived cells at d4 culture were treated with Bleb for 3 days and live CD34$^+$ cells were re-sorted. Fresh CD34$^+$ cells further purified with CD38 and CD90 expression (HSC, MPP and CPP) were also analyzed in parallel to cultured cells. Colors on gene symbols represent average gene expression intensity levels across the samples. Values in each square represent fold changes, which were calculated relative to treated (TR)-CD34$^+$, non-treated (NT)-CD34$^-$, treated-CD34$^-$, non-treated-CD34$^+$ samples within each data set. The values were derived from two independent experiments. Scales next to dendrograms indicate Pearson's correlation coefficient values used to cluster samples FIG. 16B (Left, middle) is a series of plots that demonstrates the validation of NMM-II isoform protein expression profiles by intracellular flow cytometry (n=3 donors, ±SEM, P<0.05 paired T-test for both NMM-IIA and B). FIG. 16B (Right) depicts representative images of NMM-IIA and B. Green=NMM-IIA or B; Red=CD38 (for NMM-IIA in fresh CD34$^+$ cells) or CD34 (for NMM-IIB in d4 CD34$^+$-derived culture); Bar=5 µm.

FIG. 17A through FIG. 17D, illustrates that sustained myosin-II inhibition blocks all cell division and moderately increases apoptosis, dependent on G-CSF and AHR pathways. FIG. 17A is a plot showing that myosin inhibition blocks cell division. The division rate for each HSPC subpopulation was calculated by CFSE analysis with surface markers. Mean division number for each time point was calculated by fitting Gaussian curves to CFSE data (n≥3 donors, ±SEM). FIG. 17B illustrates the results of an experiment where CD34$^+$-derived cells cultured in SCF and Tpo were treated with Bleb, G-CSF or CH-223191 for 3 days and fixed, followed by intracellular flow cytometry with the antibody specific for cleaved caspase-3 and 7-AAD for DNA staining (n=3 donors, ±SEM, P<0.05 paired T-test for untreated vs. Bleb, untreated vs. +G-CSF, and untreated vs. +CH-223191 for 4n only). G-CSF: 100 ng/ml, CH-223191: 500 nM. FIG. 17C is a series of plots illustrating that G-CSF enhances protection of HSCs but accelerates progenitor decay under Bleb treatment. CFSE profiles ware normalized by dividing the cell numbers of each division by 2 division number (initial cell number equivalent) and plotted against mean division number. For each untreated data point, the corresponding value from Bleb treatment was plotted on the same mean division number for direct comparison (n≥3 donors, ±SEM). FIG. 17D is a series of plots illustrating that HSC number is maximized by the synergy between myosin inhibition and AHR antagonism. (Left) CD34$^+$-derived cells in SCF and Tpo were treated with different doses of the selective AHR antagonist CH-223191, with or without 20 µM Bleb for 3 days. Absolute values were normalized to 104 initial cell input and fit to dose-response curves: HSC untreated and Bleb EC50=158 nM, 211 nM, respectively (Hill coefficients=1.5, 1.0, respectively); MPP untreated and Bleb EC50=114 nM for both (Hill coefficient=1.0 for both); CPP untreated and Bleb EC50=750 nM for both (Hill coefficient=2.0 for both) (n≥3 donors, ±SEM). (Right) Enrichment of Bleb-treated HSCs relative to progenitors with AHR inhibition.

FIG. 18A through FIG. 18D, illustrates that phosphorylation of NMM-IIA regulates biophysical attributes that affect HSC differentiation. FIG. 18A is a scheme showing that HSC differentiation leads to de-phosphorylation of S1943 at NMM-IIA heavy chain tail, leading to increased NMM-IIA activity. FIG. 18B illustrates that HSC differentiation by soluble growth factors accompanies decreased MIIA heavy chain phosphorylation at S1943. Cells were stained with either phospho-specific antibody against S1943 of NMM-IIA or total NMM-IIA antibody with surface markers and mean intensity was measured by flow cytometry. Each pS1943 value was normalized by the corresponding total NMM-IIA value (n=3 donors, ±SEM, fit to Log(Y)=aX+b; CD34$^-$: a=−24.56, b=6.75; CD34$^+$: a=−12.7, b=5.74). Minimum pS1943/NMM-IIA was derived from MEG01 and THP-1 cell lines (0.07±0.01). FIG. 18C is a series of images illustrating that NMM-IIA tail phospho-mimetic mutant (S1943D) increases cortical elasticity and decreases cytoskeletal integrity. COS cells were transfected as indicated. Representative images from micropipette aspiration under 1.7 kPa, 5 µm pipette radius are shown. FIG. 17D illustrates that pS1943 and NMM-IIB downregulation limits matrix sensing. (Left) COS cells were transfected as indicated and re-plated on FN (20 µg/ml)-coated soft vs. stiff gels for 24 hr before image analysis. Each cell area value was normalized by total nuclear content to correct for ploidy. ANOVA P<0.05, paired T-test *P<0.05 for GFP-S1943D or NMM-IIB knockdown 34 kPa vs. GFP or GFP-NMM-IIA 34 kPa (≥20 measurements±SEM). (Right) Representative images of COS cells transfected with GFP-tagged DNA constructs, followed by immunofluorescence with Hoechst 33342 (blue) and phalloidin (F-actin, red). Bar=10 µm.

FIG. 19A through FIG. 19C, depicts the biophysical characterization of HSC/Ps and their microenvironments. FIG. 19A depicts that HSC/MPP cell membrane is more compliant than CPP in micropipette aspiration. (Left) Aspiration length over time for CD34$^+$CD38$^-$ (HSC/MPP, 5.7/min, Intercept=8.3, η=3.2 Pa·sec) and CD34$^+$CD38$^+$ (CPP, 2.2/min, Intercept=4.7, 8.5 Pa·sec) (n=3 donors, ±SEM). (Right) Representative aspiration of a HSC/MPP cell within seconds under low pressure (0.37 kPa, bar=10 µm). FIG. 19B is a graph illustrating the effects of matrix elasticity on HSC number. On a range of FN concentrations, ratios of HSC numbers on soft (0.3 kPa) vs. stiff (34 kPa) matrices fit to dose-response curves: untreated EC50~22.4 µg/ml (Hill coefficient=1.0), bleb mean=1.1±0.2 (n≥3 donors, ±SEM). *P<0.05 soft vs stiff, two-tail, unpaired T-test. FIG. 19C is a graph illustrating the effects of matrix density on the relative number of HSCs to MPPs (HSC/MPP ratio): untreated soft and stiff IC50~100, 20.3 µg/ml, respectively (Hill coefficients=−2.0, −1.0, respectively); Bleb soft and stiff EC50~10, 4.2 µg/ml, respectively (Hill coefficient=1.0 for both) (n≥3 donors, ±SEM). *P<0.05 soft vs stiff, **P<0.01 untreated vs Bleb.

FIG. 20A through FIG. 20E, illustrates the functional effects of myosin-II inhibition on HSC differentiation. FIG. 20A (Left) illustrates the enrichment of polyploid MKs by Bleb from CD34$^+$ cells cultured in SCF and Tpo (n=4 donors). Y-axis represents the ratios between polyploid MKs and 2n+4n MKs. EC50=7.5 µM; Hill coefficient=7.0. FIG. 20A (Middle) illustrates the enrichment of BFU-E relative to CFU-GM in the absence of Epo. CD34$^+$-derived cells were cultured with SCF and Tpo under Bleb and progenitors were enumerated by colony forming assays. The maximum ratio was observed at 12.5 µM. IC50=10 µM, Hillslope=5.0 (n=3 donors±SEM). FIG. 20A (Right) illustrates the sensitivity of erythroid progenitors against Bleb in the presence of Epo. CD34$^+$ cells were cultured with SCF, IL-3 and Epo for 4 days before treating with Bleb for 3 days, followed by flow cytometry with Hoechst 33342 to stain for nuclei. BFU-E=CD34$^+$IL-3R$^+$CD36$^-$; CFU-E=CD34$^-$IL-3R$^-$CD36$^+$. Absolute values were normalized to 104 initial cell input and fit to dose-response curves: CFU-E 2n IC50=8.7 µM, Hill coefficient=−4.4; CFU-E 4n IC50=12.9 µM, Hill coefficient=−6.3; BFU-E 2n IC50=10.9 µM, Hill coefficient=−9.7; BFU-E 4n IC50=13 µM, Hill coefficient=28; Poly≥8n IC50=0.2 µM, Hill coefficient=2.0 (n=2 donors, ±SEM). FIG. 20B is a graph depicting the limiting dilution analyses showing functional LT-HSCs after myosin inhibition. Human-CD34$^+$-derived cells were treated with Bleb for 3 days and injected intra-tibially into irradiated NSG mice. The number of transplanted cells were plotted against % unsuccessful engraftment to determine the frequency of repopulating cells (n≥4 recipients per group from 2 independent experiments). FIG. 20C illustrates that transplantation with Bleb-exposed CD34$^+$-derived cells shows comparable multi-lineage engraftment in the NSG mice compared to untreated cells, including myeloid (CD33$^+$) and lymphoid (CD19$^+$) (Top graph), and erythroid (GPA$^+$) (Bottom representative figures). FIG. 20D illustrates the kinetics of human-CD41$^+$ plts in circulation were measured after transplantation of human CD34$^+$-derived cells and normalized by the initial number of CD41$^+$ cells transplanted. Areas under curves show significant differences between drug-treated and untreated. P<0.05 in both Phase-I and Phase-II from at least 9 recipients in 3 experiments (±SEM). FIG. 20E is a graph showing that human-CD41$^+$ plts derived in vivo after transplantation into NSG mice show the normal plt size compared to human blood plts. One-way ANOVA P<0.0001, *P<0.05 for untreated in vitro vs. in vivo; P<0.01 for Bleb-exposed in vitro vs. in vivo; *P<0.001 for untreated in vivo vs. mouse plt.

FIG. 21, comprising FIG. 21A through FIG. 21C, provides a list of genes that show correlation between Bleb-treated CD34$^+$ cells and fresh HSC/MPP.

FIG. 23A through FIG. 23D, depicts flow cytometric analysis of apoptosis after Bleb treatment by Annexin-V and 7AAD. FIG. 23A is a representative flow cytometry plot showing late apoptotic/necrotic (aV$^+$7AAD$^+$), early apoptotic (aV$^+$7AAD$^-$), live (aV$^-$7AAD$^-$) populations of cells treated with 20 µM Bleb. Percentages of total nucleated cells for 2n and 4n compartments (nuclear content analyzed by Hoechst 33342) are indicated as bar graphs for (FIG. 23B) late apoptotic/necrotic (FIG. 23C) early apoptotic and (FIG. 23D) live populations.

FIG. 25A and FIG. 25B, illustrates the roles of NMM-IIB in primary and COS-1 cells. FIG. 25A is a graph depicting NMM-IIB protein expression measured by intracellular flow cytometry. *P<0.05 COS-1 vs COS-1 k.d.; **P<0.01 CD34$^+$ vs CD34$^-$ n=2 independent experiments (±SEM). FIG. 25B is a series of imagines depicting the characterization of membrane elasticity by micropipette aspirations. All cells were aspirated under 3 kPa. Representative images are shown for cells aspirated within 5 min. Bar=5 µm.

FIG. 26A through FIG. 26E, depicts the characterization of biophysical factors influencing HSC/P differentiation. FIG. 26A is a graph depicting CD34$^+$ and CD34$^-$ cell number after continuous shear for 2 days. Cell number was normalized by 104 cell input. Note that no effect was observed on total NMM-IIA, NMM-IIB and pS1943 intensities. FIG. 26A is a graph illustrating the number of adherent cells after shear (per mm$^2$) on FN or collagen-I-coated gels with different elasticity. FIG. 26C is a graph illustrating the effects of FN concentrations on cell adhesion (relative number of cells adhered). FIG. 26D depicts confocal imaging of cells adhered on FN followed by shear flow. Cells were stained with phalloidin (F-actin, red) and vinculin (green). FIG. 26E is a series of graphs depicting the effects of matrix elasticity on MPP (top) and CPP (bottom) number. MPP: untreated EC50~4.3 µg/ml (Hill coefficient=1.0), Bleb mean=1.0±0.1, *P<0.05 soft vs stiff; CPP: untreated mean=1.0±0.2, Bleb mean=0.9±0.1.

FIG. 27A through FIG. 27D, depicts the in vivo characterization of NMM-II-inhibited CD34$^+$-derived cells. FIG. 27A illustrates that colony forming assays demonstrate reduced progenitor numbers by myosin inhibition. CFU-GM IC50=10.5 µM, Hill coefficient=−6; BFU-E IC50=18.6 µM, Hill coefficient=−20 (n≥3 donors, ±SEM). Note that BFU-E and colony forming unit-granulocyte, erythrocyte, monocyte and megakaryocyte (CFU-GEMM) numbers are not changed under ~15 µM, while CFU-GM number is significantly reduced. FIG. 27B (Top) provides a summary of primary and secondary NSG transplantation data. FIG. 27B (Bottom) depicts an estimation of human SRC frequency in NSG mice by extreme limiting dilution analysis (ELDA) (Hu and Smyth, 2009, Journal of Immunological Methods, 347: 70-78). FIG. 27C (Top) is scheme depicting rare human RBC isolation from NSG blood transplanted with human CD34$^+$-derived cells by a microfluidics channel adsorbed with anti-human CD47 antibody. FIG. 27C (Bottom, left) depicts adhered human RBCs, as visualized by staining with PE anti-human GPA. FIG. 27C (Bottom, right) depicts average RBC diameter (in µm, n>20 measurements for each group). FIG. 27D provides a calculation of MK decay rate, suggesting a roughly first order process with MK fragmentation half-life regardless of drug treatment of 25~28 hrs; this is ~10 times longer than the same analysis for intravenous infused MKs (Fuentes et al., 2010, J Clin Invest, 120(11): 3917-3922) and seems suggestive of intrabone transplantation.

FIG. 31A through FIG. 31C, depicts the results of experiments which demonstrate that myosin-II inhibition increases megakaryocyte (MK) maturation. FIG. 31A illustrates an in vivo scheme of MK maturation and platelet fragmentation in the bone marrow. FIG. 31B illustrates the in vitro model used to evaluate MK polyploidization. FIG. 31C depicts the results of experiments which characterize DNA content in MKs after myosin-II inhibition.

DETAILED DESCRIPTION

Figure 1:
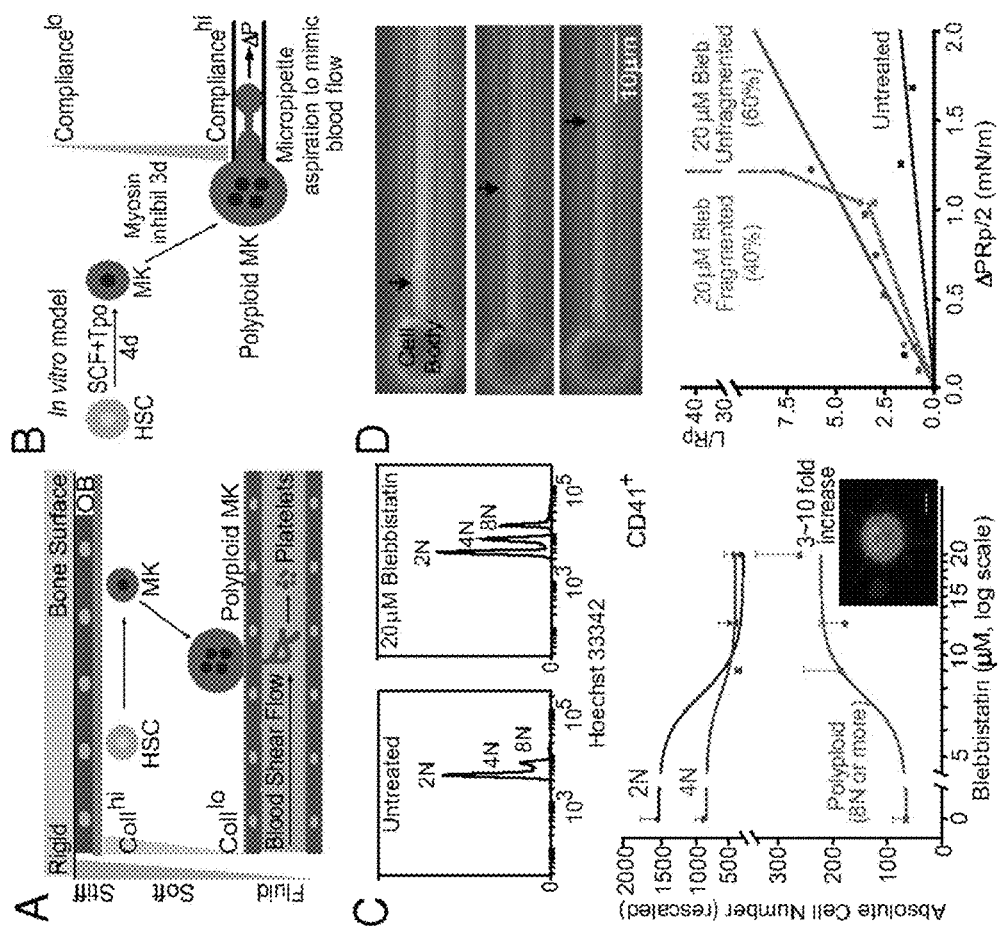
FIG. 1, comprising

The present invention relates generally to a bioreactor apparatus to isolate non-dividing cells. In one embodiment the non-dividing cells are rare blood cells. The apparatus models the vascular microenvironment of bone marrow and provides a low-cost and easy-to-use platform to enrich a variety of rare blood cells from a heterogeneous bone marrow cell population. Rare blood cells isolated by way of the present invention include, but are not limited to, hematopoietic stem cells (HSCs), polyploid megakaryocytes (MKs), polyploid non-megakaryocytes, granulocyte-macrophage progenitors, and erythroid progenitors.

The apparatus of the invention is directed towards providing a soft environment for cells within the bioreactor. In this applied environment, non-dividing cells survive, while dividing cells are eliminated. This strategy provides the ability to isolate rare blood cells without the use of biological markers such as antibodies.

In one embodiment, the apparatus provides specific biomechanical properties to cells existing within the bioreactor. Preferably, the apparatus provides a soft substrate for cells existing within the bioreactor. In one embodiment, the apparatus provides biochemical factors to cells existing within the bioreactor. In one embodiment, a provided biochemical factor comprises a composition to make the cells existing within the bioreactor soft. Preferably, the composition provides inhibition of cell contractility. In one embodiment, the apparatus provides a composition that comprises an aryl-hydrocarbon antagonist. In another embodiment, the apparatus provides a composition that comprises at least one growth factor to select for specific rare hematopoietic cells.

In one embodiment, the apparatus provides both specific biomechanical properties and biochemical factors to the cells existing within the bioreactor. Preferably, the simultaneous biomechanical properties and biochemical factors provide a soft environment to the cells within the bioreactor. The soft environment provided by the bioreactor apparatus of the invention allows for the easy isolation of rare blood cells from a population of heterogeneous hematopoietic cells.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, the term "autologous" is meant to refer to any material derived from the same individual.

"Allogeneic" refers to a graft derived from a different animal of the same species.

"Xenogeneic" refers to a graft derived from an animal of a different species.

As used herein "endogenous" refers to any material from or produced inside an organism, cell, tissue or system.

As used herein, the term "exogenous" refers to any material introduced from or produced outside an organism, cell, tissue or system.

The term "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

"Cultured" cells are isolated from tissue and expanded in controlled conditions known the art (e.g., 37° C., 5% $CO_2$), usually in a culture vessel. The "primary culture" is the first culture to become established after seeding disaggregated cells or primary explants into a culture vessel. "Expanding" as used herein refers to an increase in number of viable cells. Expanding may be accomplished by, e.g., "growing" the cells through one or more cell cycles, wherein at least a portion of the cells divide to produce additional cells.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

The term "growth medium" is meant to refer to a culture medium that promotes growth of cells. A growth medium will generally contain animal serum. In some instances, the growth medium may not contain animal serum.

The term "hydrogel" or "aquagel" refers to a network of oligomers or polymer chains that are water-insoluble, sometimes found as a colloidal gel in which water is the dispersion medium.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

The term "non-dividing cell" refers to viable cells that do not divide. In one instance, non-dividing cells do not undergo cell division. In another instance, non-dividing cells are cells that do not divide into at least two daughter cells during cell division. "Cytokinesis" refers to the process in which the cytoplasm of a single cell is divided to form two daughter cells. Some non-dividing cells, including megakaryocytes, divide their DNA during mitosis, but fail to undergo cytokinesis. This process of chromosome replication without cytokinesis is termed "endomitosis" and results in "polyploidy", referring to multiple chromosome copies in a single cell.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types.

The phrase "substrate" refers to a material and/or surface that supports the culturing of cells. A substrate of the invention can be glass, plastic, gel, hydrogel, scaffold, or any biocompatible material. A suitable substrate of the invention allows for the survival of cells, when the cells are applied within the substrate or atop the substrate surface. As should be understood by those skilled in the art, a substrate can be modified to include various agents, for example by coating the surface of the substrate with a protein, which aids in the support of the cultured cell.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to a bioreactor apparatus for the isolation of non-dividing cells from a heterogeneous cell population. In one embodiment, the non-dividing cells rare blood cells. In one embodiment, the apparatus mimics the microenvironment of the bone marrow. The apparatus of the invention provides a low-cost and easy-to-use platform to isolate rare blood cells for use in scientific research and in regenerative medicine.

In one embodiment, the bioreactor apparatus of the invention confers soft properties on cells existing within the bioreactor. The soft environment enables non-dividing cells to survive, while causing dividing cells to be eliminated. Therefore, cells with lower proliferative activity (i.e. rare blood cells) survive, while cells with higher proliferative activity do not survive. For example, HSCs and MKs, are characterized by their decreased ability for cell proliferation. MKs are unique in that they replicate their DNA without cytokinesis, in a process called endomitosis. Therefore, as MKs mature, they grow in size and increase in DNA content, without dividing.

In one embodiment, the apparatus provides a specific biomechanical environment to the cells existing within the bioreactor. For example, in one embodiment, the apparatus provides soft substrate to the cells existing within the bioreactor. In one embodiment, the substrate comprises cross-linked polyacrylamide gel having a low stiffness. In one embodiment, the substrate is a soft substrate having a low stiffness of about 0.3 kPa to 2 kPa. Preferably, the low stiffness of the substrate allows for the survival of non-dividing cells while reducing the number of dividing cells in the cell population.

In one embodiment, the apparatus provides biochemical factors to the cells existing within the bioreactor. In one embodiment, the biochemical factors comprise compositions which inhibit or reduce cell contractility. For example, in one embodiment the apparatus provides compositions that inhibit myosin-II. Preferably, reduced cell contractility enables the survival of non-dividing cells. In one embodiment, biochemical factors further comprise at least one growth factor to select for a specific set of cells. In another embodiment, biochemical factors comprise an aryl-hydrocarbon antagonist.

In one embodiment, the apparatus provides both biomechanical properties and biochemical factors to the cells existing within the bioreactor. In one embodiment, the simultaneous biomechanical properties and biochemical factors provide a soft environment for the cells existing within the bioreactor. In one embodiment, the apparatus of the invention comprises a soft substrate with embedded compositions, where the embedded compositions comprise inhibitors of cell contractility, aryl-hydrocarbon antagonists, and/or minimal growth factors.

In one embodiment, the apparatus of the invention has a cylindrical design and is easily converted into a syringe. The design of the apparatus thereby provides an easy-to-use platform to elute viable cells from the apparatus. In one embodiment, the apparatus comprises a housing comprising a hollow tube, where the hollow tube includes two openings and an inner surface to form a passage therethrough, a substrate layer conjugated to at least a portion of the inner surface of the tube; and gas permeable caps removably attached to the tube openings.

In another aspect, the invention is related to methods of isolating non-dividing cells from a cell population. In one embodiment, the methods of the invention isolate rare blood cells from a sample of heterogeneous hematopoietic cells. In one embodiment, the method comprises providing a soft environment to a heterogeneous population of hematopoietic cells. In one embodiment, the method comprises culturing hematopoietic cells on a soft substrate. In one embodiment, the method further comprises culturing hematopoietic cells in the presence of inhibitors of cell contractility. In one embodiment, the method further comprises culturing hematopoietic cells in the presence of a growth factor. In one embodiment, the method further comprises culturing hematopoietic cells in the presence of an aryl-hydrocarbon receptor antagonist. The methods of the invention enable the survival of non-dividing rare blood cells, while eliminating the dividing cells.

The invention further comprises the use of a non-divided cell, isolated by use of the bioreactor apparatus. In one embodiment, the non-dividing cell is used to program the outcome of blood cell transplantation in a subject. In another embodiment, the non-dividing cell is used for one of early recovery of platelet count, clearance of granulocyte-macrophage progenitors, maintenance of long term hematopoietic stem cell activity, or red blood cell generation. In another embodiment, the non-dividing cell is assayed for the presence of at least one type of rare blood cell by detecting the presence of at least one specific biomarker associated with the at least one type of rare blood cell Current technologies for cell isolation involve multi-step procedures to label cells with specific set of antibodies and sort cells by FACS. In the case of rare cell isolation, multiple antibodies are involved, which increases the cost. In addition, the capital cost of a FACS machine can exceed over $1 million and additional costs come from hiring technical staff dedicated to this specialized machine. In contrast, the present invention offers a low-cost solution to isolate important rare blood cells—the manufacturing cost is estimated to be less than $10 per unit. The apparatus is user-friendly, since it consists of a streamlined input and output system, hence minimizing current multi-step processes to only a few steps to obtain rare cells. The global market of cell and tissue separation and characterization technologies is estimated to be ~$2 billion as of 2011 (BCC Research, 2008). The invention is addressing this attractive market by offering a low-cost solution to isolate rare cells. Hence, this approach not only reduces scientific research costs, but also capital costs needed for clinical sample preparations.

Running FACS machine requires high power consumption. In addition, a large quantity of sheath fluid is discarded every day per each FACS machine. Therefore, with current technologies, one will have to go through a substantial amount of energy consumption to obtain a small number of rare cells. Because the procedure is all done in a single confined space, the invention offers an energy-friendly way to obtain rare cells.

In scientific settings, the invention offers a useful tool to many investigators in need of obtaining rare blood cells for discovery purposes, which is normally difficult due to the high cost of current procedures. The presently described device enables isolation of known rare blood cells (e.g. HSCs and MKs) but also enables characterization of other yet-to-be discovered rare cell types that may have physiological or pathological roles. This is particularly important for discovery of different cancer stem cells, which are present at a very low frequency and normally remain undetectable by traditional assays. In addition, the device offers a platform to study biology and test drugs under a more physiological context, instead of using plastic culture dishes. In clinical settings, the invention offers an efficient method to prepare cell products for the purpose of transfusion into patients with blood disorders, with applications for adult stem cell transplantation and treatment of thrombocytopenia (low platelet count). With the potential cost reduction in the preparation of important cell types, this method makes cell therapy more accessible to general setting. As a consequence, the presently described device and methods improve overall healthcare, especially healthcare in rural areas, underserved communities, and developing countries.

The invention provides a bioreactor apparatus that provides a soft microenvironment to cells in order to isolate non-dividing cells, including but not limited to rare blood cells. In one embodiment, the soft environment is conferred by providing a soft substrate, upon which cells are cultured. The substrate of the present invention can be of any size or thickness. The substrate comprises a surface which has a static or dynamic interaction with applied cells during culturing.

The present invention is related to the finding that a soft substrate enables the survival of non-dividing rare blood cells, and the improved maturation of MKs. In one embodiment, the substrate of the bioreactor has a stiffness ranging from 0.01 kPa to 20 kPa. Preferably, the substrate has a stiffness ranging from 0.1 kPa to 10 kPa. More preferably, the substrate has a stiffness ranging from 0.2 kPa to 5 kPa. Most preferably, the substrate has a stiffness of 0.3 kPa to 2 kPa.

The substrate of the apparatus is not limited as to the type of substrate used. For example, any substrate known in the art suitable for the culturing of cells can be used in the present invention. Non-limiting examples of types of substrates include polyacrylamide gels, hydrogels, scaffolds, and the like.

In a preferred embodiment, the substrate of the bioreactor apparatus comprises a polyacrylamide gel. The stiffness of the polyacrylamide gels of the invention can be varied by altering the ratio of N,N' methylene-bis-acrylamide and acrylamide solutions. For example, a N,N' methylene-bis-acrylamide to acrylamide solution ratio of 0.07%:3% is used to generate a soft gel (0.3 kPa), whereas a N,N' methylene-bis-acrylamide to acrylamide solution ratio of 0.3%:8% is used to generate a stiff gel (34 kPa).

In one embodiment, the polyacrylamide gel is coated with proteins, or portions thereof, including but not limited to collagen, fibronectin, laminin, vitronectin, gelatin, and the like. In one embodiment, collagen is cross-linked with the polymerized polyacrylamide gels. Cross-linking of collagen, or of any other protein, can be performed by any method known in the art. In one embodiment, collagen is cross-linked to the gel using sulfo-SANFAH by UV crosslinking. In one embodiment, the concentration of coated collagen is 0.02 ng/cm$^2$ to 20,000 ng/cm$^2$. Preferably, the concentration of coated collagen is 0.2 ng/cm$^2$ to 2,000 ng/cm$^2$. More preferably, the concentration of coated collagen is 2 ng/cm$^2$ to 200 ng/cm$^2$. In one embodiment, the substrate is coated with fibronectin. In one embodiment the concentration of coated fibronectin is 20 ng/cm$^2$ to 20,000,000 ng/cm$^2$. Preferably, the concentration of coated collagen is 200 ng/cm$^2$ to 2,000,000 ng/cm$^2$. More preferably, the concentration of coated collagen is 2,000 ng/cm$^2$ to 200,000 ng/cm$^2$. A soft polyacrylamide gel substrate of the invention allows for the survival of non-dividing rare blood cells. Further, the soft substrate induces the maturation of MKs.

As would be understood by those skilled in the art, the polyacrylamide gel of the invention can be further modified through the addition of various compounds or agents. Such compounds or agents include, but are not limited to, hormones, growth factors, proteins, anti-inflammatory agents, antibiotics, anti-fungals, anti-virals, vitamins, nutrients and the like. Such agents can be coated along the surface of the gel, or alternatively embedded within the gel such that the agent diffuses out from within the gel.

In another embodiment, the substrate comprises a hydrogel. Hydrogels can generally absorb a great deal of fluid and, at equilibrium, typically are composed of 60-90% fluid and only 10-30% polymer. In a preferred embodiment, the water content of hydrogel is about 70-80%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility can be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66; Peppas and Mikos. Preparation Methods and Structure of Hydrogels in Hydrogels in Medicine and Pharmacy, Peppas, Ed. 1986, CRC Press: Boca Raton, Fla., pp 1-27). The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose (see.: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical crosslinking synthetic polymers include but are not limited to (meth)acrylate-oligolactide-PEO-oligolactide-(meth)acrylate, poly(ethylene glycol) (PEO), polypropylene glycol) (PPO), PEO-PPO-PEO copolymers (Pluronics), poly (phosphazene), poly(methacrylates), poly(N-vinylpyrrolidone), PL(G)A-PEO-PL(G)A copolymers, poly(ethylene imine), etc. (see A. S Hoffman, 2002Adv. Drug Del. Rev, 43, 3-12). In some embodiments, the transparent hydrogel scaffold comprises poly(ethylene glycol) diacrylate (PEGDA).

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels can also be made degradable in vivo by incorporating PLA, PLGA or PGA polymers. Moreover, hydrogels can be modified with fibronectin, laminin, vitronectin, or, for example, RGD for surface modification, which can promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes can influence strength, elasticity, and degradation properties of the instant hydrogels (Nguyen and West, 2002, Biomaterials 23(22):4307-14; Ifkovits and Burkick, 2007, Tissue Eng. 13(10):2369-85).

Hydrogels can also be modified with functional groups for covalently attaching a variety of proteins (e.g., collagen) or compounds such as therapeutic agents. Therapeutic agents which can be linked to the matrix include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like. The therapeutic agent can also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix can be via a protease sensitive linker or other biodegradable linkage. Molecules which can be incorporated into the hydrogel matrix include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α.-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art.

It should be appreciated by those in skilled in the art that the mechanical properties of the hydrogel are greatly influenced by the cross-linking time and the amount of cross-linking agents.

In another embodiment utilizing a cross-linking agent, polyacrylated materials, such as ethoxylated (20) trimethylpropane triacrylate, may be used as a non-specific photo-activated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Continuous exposure of this reactive mixture to long-wavelength light (>498 nm) would produce a cross-linked hydrogel network The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent can include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents can be added to the matrix composition before or during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

The apparatus of the invention comprises a pharmacological manipulation of cell contractility of cells existing within the bioreactor. The present invention is related to providing a soft environment for the cells, thereby providing an environment to allow for the selective viability of non-dividing cells. In one embodiment, the pharmacological manipulation comprises inhibiting the activity of proteins known to regulate cell contractility. In one embodiment, the pharmacological manipulation inhibits myosin-II. As described herein, myosin-II inhibition promotes the maturation of MKs. Therefore, the bioreactor apparatus of the invention comprises compositions known to inhibit myosin-II, thereby promoting the isolation and maturation of MKs and other rare blood cells.

Actomyosin forces drive a number of general cellular processes. Fission at the end of cytokinesis is one such process promoted by myosin-II with inhibition of non-muscle myosin-II (NMM-II) in proliferating cells producing more binucleate and polyploid cells (Straight et al., 2003, Science, 299:1743-1747). Actomyosin forces also help to establish an active cortical tension, which stiffens and stabilizes the plasma membrane (Engler et al., 2006, Cell, 126:677-689). Inhibition of NMM-II thus tends to cause at least some adherent cell types to exhibit more filipodia-like membrane extensions and appear more dendritic (Straight et al., 2003, Science, 299:1743-1747). Finally, NMM-II contributes to adhesion as cells attach to ligand and sense the elasticity of their microenvironment, impacting differentiation of both adult (Engler et al., 2006, Cell, 126:677-689) and embryonic stem cells (Conti et al., 2004, J Biol Chem, 279:41263-41266). These basic functions of myosin are also partially coupled. Membrane or cortical rigidity increases with matrix rigidity as cells apply more tension to adhesion complexes on stiff substrates, promoting focal adhesion growth (Engler et al., 2006, Cell, 126:677-689). Cytokinesis is also modulated by cell adhesion (Zang et al., 1997, Mol Biol Cell, 8:2617-2629) with nonspecific attachment overriding the polyploidization described originally for suspensions of myosin-II-null *Dictyostelium* amoeba (De Lozanne et al., 1987, Science, 236:1086-1091). However, cells in tissues do not grow in suspension: contact and adhesion are unavoidable in vivo. In all of these contexts, megakaryocytes (MKs) are intriguing in that they are polyploid, they exhibit proplatelet extensions suggestive of a highly flexible membrane, and they adhere within a complex bone marrow microenvironment (FIG. 1A). Furthermore, MKs and MKgenerated platelets express abundant NMM IIA (MYH9) (Maupin et al., 1994, J Cell Sci, 107:3077-3090).

Differentiation to MKs in vivo starts with multipotent hematopoietic stem cells (HSCs) that are located at osteoblastic niches on rigid, high collagen bone (Calvi et al., 2003, Nature, 425:841-846). As MKs mature, they replicate their DNA but do not divide, a process termed endomitosis. These cells also migrate into the soft marrow space and into perivascular niches (Junt et al., 2007, Science, 317:1767-1770). Whereas, MKs do not transmigrate into blood, they do extend tubular membrane projections, known as proplatelets, into blood, where shear flow fragments the extensions to generate circulating platelets (Junt et al., 2007, Science, 317:1767-1770). In case of injury to a vessel wall, or perhaps other activating signals, platelets adhere to the wall or to a multiplatelet thrombus and use actomyosin forces to contract the thrombus forming a tight seal on the wall.

Human mutations in the MYH9 gene cause May-Hegglin anomaly, characterized by large platelets and thrombocytopenia (low platelet count) (Kelley et al., 2000, Nat Genet, 26:106-108; Seri et al., 2000, Nat Genet, 26:103-105). In mouse, deletion of MYH9 in MKs also produces May-Hegglin-like defects (Eckly et al., 2009, Blood, 113:3182-3189; Eckly et al., 2010, J Thromb Haemost, 8:2243-2251). Paradoxically, pharmacological inhibition of NMM-II ATPase by blebbistatin in mouse adult (Eckly et al., 2010, J Thromb Haemost, 8:2243-2251) and mouse embryonic (Chen et al., 2007, Blood, 110:171-179) systems is reported to produce a two- to ~threefold increase in proplatelet extensions but not affect MK ploidy or size, at least for the doses or times tested.

In one embodiment, the apparatus of the invention comprises anti-contractility agents. These anti-contractility agents are compositions that are known to inhibit cell contractility. Such compositions can include chemical agents (such as toxins), pharmaceuticals, peptides, proteins (such as antibodies, cytokines, enzymes, etc.), and nucleic acids, including gene medicines and introduced genes, which may encode therapeutic agents such as proteins, antisense agents (i.e. nucleic acids comprising a sequence complementary to a target RNA expressed in a target cell type, such as RNAi or siRNA), ribozymes, etc. Non-limiting examples of such compositions include ML-7, a specific inhibitor of myosin light chain kinase, and Y-27632, an inhibitor of RhoA kinase. In another embodiment, the apparatus comprises nucleotide sequences (e.g. RNAi, siRNA) that are specific to knock down the expression of myosin-II or any other protein known to regulate cell contractility. In yet another embodiment, the apparatus comprises delivery and expression of mutant proteins that lack the functionality of myosin-II or other proteins known to regulate cell contractility. As would be understood by those skilled in the art, such compositions can be delivered to the cells by a variety of means known in the art. Non-limiting examples of delivery vehicles include polymersomes, vesicles, micelles, plasmid vectors, viral vectors, retroviral vectors and the like. In one embodiment, the apparatus of the invention comprises compositions known to inhibit myosin-II. Such compositions can be chemical agents (such as toxins), pharmaceuticals, peptides, proteins (such as antibodies, cytokines, enzymes, etc.), and nucleic acids, including gene medicines and introduced genes, which may encode therapeutic agents such as proteins, antisense agents (i.e. nucleic acids comprising a sequence complementary to a target RNA expressed in a target cell type, such as RNAi or siRNA), ribozymes, etc. For example, in one embodiment, the composition is blebbistatin. In one embodiment the effective concentration of blebbistatin is 0.05 µM to 2 mM. Preferably, the effective concentration of blebbistatin is 0.5 µM to 200 µM. More preferably, the effective concentration of blebbistatin is 5 µM to 20 µM.

In one embodiment, the applied composition to inhibit cell contractility, for example an agent to inhibit myosin-II, is applied in a reversible manner. That is, in an aspect of the invention cell contractility is inhibited for a defined period, but is later restored. In one embodiment, restoration of cell contractility comprises removing an applied inhibitor, for example blebbistatin. In another embodiment, restoration of cell contractility comprises administration of nucleic acid sequences or proteins to the cells to increase the expression of functional proteins that function in cell contractility.

In another embodiment, the apparatus comprises compositions to inhibit the aryl-hydrocarbon receptor. As would be understood by those skilled in the art, such compositions can be chemical agents (such as toxins), pharmaceuticals, peptides, proteins (such as antibodies, cytokines, enzymes, etc.), and nucleic acids, including gene medicines and introduced genes, which may encode therapeutic agents such as proteins, antisense agents (i.e. nucleic acids comprising a sequence complementary to a target RNA expressed in a target cell type, such as RNAi or siRNA), ribozymes, etc. Non-limiting examples of compositions to inhibit the aryl-hydrocarbon receptor include StemRegenin-1 (4-(2-((2-Benzo[b]thiphen-3-yl)-9-isopropyl-9H-purin-6-yl)amino) ethyl)phenol), CH-223191 and resveratrol. In one embodiment the concentration of StemRegenin-1 is 0.005 µM to 100 µM. Preferably, the concentration of StemRegenin-1 is 0.05 µM to 10 µM. More preferably, the concentration of StemRegenin-1 is 0.5 µM to 1 µM In one embodiment, the culturing of cells within the bioreactor comprises culturing in the presence of cell culture media supplemented with minimal growth factors. Basal media useful in mammalian cell culture are known in the art. Non-limiting examples of basal media useful in the defined culture medium of the invention include Minimum Essential Medium Eagle, ADC-1, LPM (Bovine Serum Albumin-free), F10 (HAM), F12 (HAM), Dulbecco's Modified Eagle Medium (DMEM—without serum), DMEM/F12, DCCM1, DCCM2, RPMI 1640, BGJ Medium (with and without Fitton-Jackson Modification), Basal Medium Eagle (BME—with the addition of Earle's salt base), Yamane, IMEM-20, IMDM, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non-essential amino acids), StemLine-I, StemLine-II, StemSpan, among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. These and other useful media are available from GIBCO, Grand Island, N.Y., USA, and Biological Industries, Bet HaEmek, Israel, among others. A number of these media are summarized in Methods in Enzymology, Volume LVIII, "Cell Culture", pp. 62-72, edited by William B. Jakoby and Ira H. Pastan, published by Academic Press, Inc In some embodiments, the culture medium of the invention may further include any components known by the skilled artisan to be useful in the culturing of blood cells (including HSCs and the like). In one embodiment, the media comprise animal serum, for example horse serum, goat serum, and fetal bovine serum. In another embodiment, the media comprises conditioned media. In another embodiment, the media comprises serum-free media. In an embodiment, a medium may include at least one additional growth factor. Growth factors useful in the present invention include, but are not limited to, stem cell factor (SCF), glial cell line-derived neurotrophic factor (GDNF), GDNF-family receptor (including GFRα1), leukemia inhibitory factor (LIF), hepatocyte growth factor (HGF), acidic fibroblast growth factor (aFGF), epidermal growth factor (EGF), insulin-like growth factor (including IGF-1 and IGF-2), keratinocyte growth factor (KGF), nerve growth factor (NGF), transforming growth factor beta (TGF-β), vascular endothelial cell growth factor (VEGF), platelet-derived growth factor (PDGF), FMS-like tyrosine kinase 3 ligand (Flt3L or Flt3LG), transforming growth factor (including TGF-β I through V, as well as the TGF-β superfamily: BMP-1 through 12, GDF-1 through 8, dpp, 60A, BIP, OF), various interleukins (such as IL-1 through IL-18), various colony-stimulating factors (such as granulocyte/macrophage colony-stimulating factor (GM-CSF)), Sonic hedgehog, notch, leptin, hormones (such as Thrombopoietin (Tpo) and Erythropoietin (Epo)), and various interferons (such as IFN-gamma). It is further recognized that additional components may be added to the culture medium, provided they support the culturing of HSCs, progenitors cells, MKs, and other blood cells. Such components may be biologically-relevant lipids, antibiotics, antimycotics, anti-oxidants (reducing agents), amino acids, and other components known to the art for the culture of cells. Biologically-relevant lipids include neutral triglycerides of predominantly unsaturated fatty acids such as linoleic, oleic, palmitic, linolenic, and stearic acid, as well as phospholipids such as phosphatidylethanolamine and phosphatidylcholine. Anti-oxidants useful in the defined medium of the invention include, but are not limited to, β-mercaptoethanol, ascorbic acid, monothioglyceroll and dithiothreitol. Antibiotics that can be added into the medium include, but are not limited to, penicillin and streptomycin. Additionally, components may be added to or removed from the medium to induce or enhance the differentiation process.

Preferably, the components are free of endotoxins. Endotoxins are a pyrogen, which is defined as a substance that can cause a fever response. Endotoxins are also toxic to cells grown in tissue culture conditions.

In preferred embodiments, a medium's endotoxicity, as measured in endotoxin units per milliliter ("eu/ml"), will be less than about 0.1 eu/ml, and, in more preferred embodiments, will be less than about 0.05 eu/ml. In particularly preferred embodiments, the endotoxicity of the base medium will be less than about 0.03 eu/ml. Methods for measuring endotoxicity are known in the art. For example, a preferred method is described in the "Guideline on Validation of the *Limulus Amebocyte* Lysate Test as an End-product Endotoxin Test for Human and Animal Parental Drugs, Biological Products and Medical Devices," published by the U.S. Department of Health and Human Services, FDA, December 1987.

Bioreactor

The present invention is related to a bioreactor apparatus for the isolation of non-dividing cells from a cell population. In one embodiment, the bioreactor of the invention isolates rare blood cells from a heterogeneous population of hematopoietic cells. The initial population of hematopoietic cells can be derived from a variety of sources, including but not limited to the bone marrow, umbilical cord blood, peripheral blood, spleen, liver, and thymus of a subject. Cells to be provided to the apparatus of the invention includes, but are not limited to, hematopoietic mononuclear cells, CD34$^+$ cells, and CD133$^+$ cells. As would be understood by those skilled in the art, any bioreactor or culture vessel can be used in the present invention. Any suitable culture vessel can be adapted to culture hematopoietic cells in accordance with the invention. For example, vessels having a substrate suitable for matrix attachment include tissue culture plates (including multi-well plates), pre-coated (e.g., gelatin-pre-coated) plates, T-flasks, roller bottles, gas permeable containers, and bioreactors. To increase efficiency and cell density, vessels (e.g., stirred tanks) that employ suspended particles (e.g., plastic beads or other microcarriers) that can serve as a substrate for attachment of an extracellular matrix can be employed. In other embodiments, cells can be cultured in suspension by providing the matrix components in soluble form. As will be appreciated, fresh medium can be introduced into any of these vessels by batch exchange (replacement of spent medium with fresh medium), fed-batch processes (i.e., fresh medium is added without removal of spent medium), or ongoing exchange in which a proportion of the medium is replaced with fresh medium on a continuous or periodic basis. Large-scale culturing devices and continuous cell culture systems are known in the art. See, for instance, Ulloa-Montoya et al. (2005, J. Biosci. Bioengineer. 100:12-27).

In one embodiment, the bioreactor of the present invention comprises a housing or vessel, where the surface of the housing or vessel is modified to be coated with a substrate layer. For example, in one embodiment the substrate layer is coated along a glass surface using silane chemistry with allytrichlorsilane (ATCS) solution. However, the bioreactor of the invention is not limited as to if or how the substrate layer is coated on the housing surface.

In one embodiment, the bioreactor of the present invention comprises a soft substrate, for example a polyacrylamide gel. In one embodiment, the gel is embedded with compositions comprising growth factors, hormones, arylhydrocarbon receptor antagonists and inhibitors of cell contractility. Examples of such compositions have been provided elsewhere herein. Examples of growth factors which can be used in present invention include, but are not limited to, stem cell factor (SCF) and thrombopoietin (Tpo), G-CSF, Epo, IL-3. In one embodiment, the inhibitor of cell contractility is blebbistatin. However, as would be understood by those skilled in the art, any composition that inhibits cell contractility can be used in the present invention. The gel, embedded with the compositions of the invention, provides a matrix-elasticity tunable solid biomaterial that provides a soft microenvironment for cells within the bioreactor.

Although in various embodiments of the invention described herein, the bioreactor apparatus for isolation of rare blood cells comprises a soft substrate, the skilled artisan will understand that the invention described herein also includes a bioreactor apparatus for the isolation of rare blood cells where the substrate layer is not soft, including bioreactors comprising substrate layers that are stiff.

As described elsewhere herein, in one embodiment, the substrate layer of the invention is coated with proteins including but not limited to collagen and fibronectin via an amine-reactive cross linker, for example sulfo-SANPAH. As would be understood by those skilled in the art, any protein, at any protein concentration, may be attached to the surface of the substrate layer.

As would be understood by those skilled in the art, the bioreactor of the present invention is not limited by its size or shape. For example, in one embodiment, the bioreactor comprises a flat substrate coated along a flat housing. Thus, the bioreactor can be two-dimensional or three-dimensional. In one embodiment the bioreactor has a cylindrical shape, for example a hollow tube. In one embodiment, the inner surface of a hollow glass cylindrical housing is coated with ATCS and then coated with a soft substrate layer. In one embodiment, coating of the housing with the soft substrate layer comprises inserting a glass mold having diameter smaller than the diameter of the housing cavity and pouring the unpolymerized solution into the space between the inner surface of the housing and the mold. After polymerization of the substrate layer, the mold is removed, thereby producing a cylindrical bioreactor comprising a hollow cylindrical housing with an inner coating of a substrate layer, where the substrate layer is a polyacrylamide gel. In one embodiment of the bioreactor, the substrate layer is embedded with compositions including, but not limited to anti-contractility agents, aryl-hydrocarbon receptor antagonists, and growth factors.

In one embodiment, hematopoietic cells, obtained from a subject, are suspended in a culture medium and placed into the bioreactor. In one embodiment, the bioreactor further comprises an inlet and an outlet that supplies gas (e.g. oxygen) to the cells while being cultured. In one embodiment, the ends of the bioreactor are capped with gas-permeable caps. During culturing of the cells within the bioreactor, the embedded compositions diffuse from the substrate layer and exert their activity on the cells. In another embodiment, compositions including, but not limited to, growth factors, aryl-hydrocarbon receptor antagonists, and anti-contractility agents are added to the culture media.

The soft environment of the bioreactor, provided by the low stiffness of the substrate layer along with the contractility inhibitors allows for survival of non-dividing rare blood cells (e.g. HSCs and MKs), while not supporting the survival of the dividing cells. In one embodiment, the bioreactor is easily converted into a syringe. In this aspect, the syringe is used to elute the cells from the bioreactor. In one embodiment, the conversion of the apparatus into a syringe comprises removal of the gas permeable ends from the cylinder, and adding a sterile tip to one end while adding a plunger unit to the opposite end. In this aspect pushing of the plunger unit into the hollow portion of the apparatus removes adherent cells from the apparatus through the tip so that the cells are captured.

In one embodiment, the methods of the invention comprise the separation of viable cells from non-viable cells. One technique for this separation includes contacting the cell population with an antibody for Annexin V, and recovering from the cell population all the cells that do not bind to the Annexin V antibody. In one embodiment, magnetic beads coated with an antibody against Annexin V are applied to the cells, and cells that are not bound by the magnetic beads are recovered, thereby isolating the viable rare blood cells. In one embodiment, the magnetic beads coated with an antibody against Annexin V are added to the sterile tip, when the apparatus is in its syringe conformation. Thus, when the cells pass through the tip, dead cells bind to the beads and are retained in the tip, while viable cells are collected.

The bioreactor apparatus of the invention enables the simple, easy-to-use, and inexpensive isolation of rare blood cells. Whereas current methods to isolate blood cells require a multitude of antibodies and/or the use of an expensive FACS machine, the present invention utilizes the soft microenvironment of the apparatus to easily and cheaply select for non-dividing rare blood cells. Further, the present invention is a self-contained unit, not requiring the use of other machinery.

The present invention is directed towards a bioreactor apparatus for the isolation of rare blood cells. As such, the bioreactor apparatus may comprise different biomechanical properties and/or biochemical factors that are specific for the isolation of a specific rare blood cell. For example, in one embodiment, for the isolation of polyploid MKs, the bioreactor comprises a soft substrate, blebbistatin, collagen-I, SCF, and Tpo. In another embodiment, for the isolation of polyploid non-megakaryocytes, the bioreactor comprises a soft substrate, blebbistatin, collagen-I, SCF, Tpo, and G-CSF. In yet another embodiment, for the isolation of HSCs, the bioreactor comprises a soft substrate, blebbistatin, fibronectin, StemRegenin-1, SCF, Tpo, and G-CSF. In yet another embodiment, for the isolation of granulocyte-macrophage progenitors, the bioreactor comprises a substrate, blebbistatin, SCF, IL-3, and Epo. In yet another embodiment, for the isolation of erythroid progenitors, the bioreactor comprises a substrate, blebbistatin, SCF, Tpo, and G-CSF. However, has would be understood by those skilled in the art, any composition can be substituted with an effective amount of an alternative composition that provides the same functional activity. For example, in one embodiment, blebbistatin is substituted by an effective amount of a nucleotide sequence (e.g. RNAi or siRNA) to knock down myosin-II expression, thereby inhibiting myosin-II activity. In another embodiment, blebbistatin is substituted with other compositions that impair cell contractility, including reversine or Y-27632.

In another aspect, the present invention is related to methods of isolating specific populations of non-dividing cells. In one embodiment, the non-dividing cells are rare blood cells. As described elsewhere herein, the present invention is related to providing soft microenvironment to cultured blood cells and progenitor cells. As such the methods of the invention comprise providing a soft substrate to hematopoietic cells obtained from a subject, and culturing the cells in the presence of at least one anti-contractility agent. In one embodiment, the method further comprises culturing cells in the presence of at least one aryl-hydrocarbon receptor antagonist. In yet another embodiment, the method further comprises culturing cells in the presence of at least one growth factor. As described elsewhere herein, the soft substrate provided to the cells can be of any suitable biocompatible substrate, including, but not limited to polyacrylamide gels, hydrogels, scaffolds, and the like. In the preferred embodiment, the substrate has a stiffness of 0.3 kPa to 2 kPa. In one embodiment, the methods of the invention further comprise capturing the viable rare blood cells. In one embodiment the capturing of viable rare blood cells comprises separating the viable rare blood cells from the dead cells. In one embodiment, the separation of viable and dead cells comprises applying an antibody specific for a marker known to exist on only dead cells. In this aspect, cells that do not bind to the antibody are then collected as the specific population of rare blood cells. As would be understood by those skilled in the art, the dead cell marker may be of any kind known in the art, for example Annexin V. In another embodiment, the separation of viable and dead cells comprises applying an antibody specific for a marker known to exist only on viable cells, and collecting only cells that bind to such an antibody.

In one embodiment, the methods of the present invention comprise the use of isolated non-dividing cells. In one embodiment, the methods comprise the use of isolated rare blood cells. In one embodiment, the methods of the invention comprise using the selected cells to program outcomes for blood cell transplantation in vivo. For example, the methods can comprise the isolation of megakaryocytes and the use of isolated megakaryocytes to increase the platelet count of a subject. Low platelet count, known as thrombocytopenia, can occur for a variety of reasons, including but not limited to, Vitamin B deficiency, leukemia, sepsis, hereditary disorders, idiopathic thrombocytopenic purpura, and thrombotic thrombocytopenic purpura. The present invention includes the use of isolated rare blood cells, for example megakaryocytes, for the early recovery of platelet counts in subjects with thrombocytopenia or otherwise in need of an increase in platelet count. In another embodiment, the methods of the invention comprise using isolated rare blood cells for the maintenance of long term hematopoietic stem cell activity. In another embodiment, the methods of the invention comprise using isolated rare blood cells for increasing red blood cell production. In yet another embodiment, the methods of the invention comprise using the isolated rare blood cells for the clearance of granulocyte-macrophage progenitors.

In one embodiment, the methods of the present invention comprise measuring the presence of specific cells in the isolated non-dividing cells. In one embodiment, the measuring the presence of specific cells comprises evaluating the expression of specific biomarkers. For example, isolated cells can be measured for the presence of megakaryocytes and functional HSCs. For example, biomarkers used to identify cells as MKs include, but are not limited to, myosin regulatory light chain 12A, gelsolin, vinculin, filamin A, talin 1, actin, tropomyosin alpha-4 chain, vimentin, MYH9, MYL6, tubulin alpha 1A, plastin 2, tubulin beta 2C, actin-related protein 2/3 complex 4, transgelin 2, moesin, plectin, profiling 1, stathmin, cofilin 1, and alpha-actinin-4 Biomarkers used to identify HSCs include but are not limited to non-muscle myosin IIB (MYH10), CD34, THY1, PROM1, EMCN, HLF, MNDA, MME, CPA3, ALOX5AP, and GPR126. As would be understood by those skilled in the art, expression of biomarkers can be assessed by a variety of techniques known in the art, including, but not limited to, PCR, qRT-PCR, microarray, western blot, mass spectrometry, immunofluorescence, and the like.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Myosin-II Inhibition and Soft 2D Matrix Maximize Multinucleation and Cellular Projections Typical of Platelet-Producing Megakaryocytes Cell division, membrane rigidity, and strong adhesion to a rigid matrix are all promoted by myosin-II. Thus, it is predicted that multinucleated cells with distended membranes—typical of megakaryocytes (MKs)—result from low myosin activity in cells on soft matrices. Paradoxically, myosin mutations lead to defects in MKs and platelets. As described herein, reversible inhibition of myosin-II, sustained over several cell cycles, produce 3- to 10-fold increases in polyploid MK and a number of other cell types. Even brief inhibition generates highly distensible, proplatelet-like projections that fragment readily under shear, similar to what is seen in platelet generation from MKs in vivo. The effects are maximized with soft 2D collagenous matrices, like the perivascular niches in marrow, rather than rigid 3D matrices, like bone. Although multinucleation of other primary hematopoietic lineages helps to generalize a failure-to-fission mechanism, lineage-specific signaling is described herein, with increased polyploidy regulated by phosphorylation of myosin-II heavy chain. Label-free mass spectrometry quantitation of the MK proteome uses a unique proportional peak fingerprint (ProPF) analysis to also show upregulation of the cytoskeletal and adhesion machinery critical to platelet function. Myosin-inhibited MKs generate more platelets in vitro and in vivo, while agonist stimulation activates platelet spreading and integrin $\alpha IIb\beta 3$. Myosin-II thus is a central, matrix-regulated node for MK-poiesis and platelet generation.

Here, the role of NMM-IIA role in MK maturation and subsequent platelet production is examined directly starting with human bone marrow (BM)-derived CD34$^+$ cells cultured with just two cytokines to differentiate into MK progenitors followed by sustained reversible inhibition of myosin-II for 3 days (FIG. 1B). Further detail or interpretation of the experiments and data presented herein is found in Shin et al., 2011, PNAS, 108(28): 11458-11463, whose entirety is incorporated by reference herein as if set forth herein in its entirety.

The materials and methods employed in these experiments are now described.

Materials.

For washing or antibody staining of cells, PBS without $Ca^{2+}$ or $Mg^{2+}$ (Invitrogen) was supplemented with either 1% BSA or 2% FBS (Sigma-Aldrich). For cell culture, DMEM, RPMI-1640 medium, 0.05% trypsin-EDTA, penicillin-streptomycin were all purchased from Invitrogen. For Western analysis, protease inhibitor mixture was purchased from Sigma. For flow cytometry, 7-Amino-actinomycin D (7-AAD) was purchased from Sigma and Hoechst 33342 was purchased from Invitrogen. The (±)-blebbistatin was purchased from EMD Biosciences, and reversine, ML-7, and Y-27632 were purchased from Sigma. All cytokines, including human recombinant stem-cell factor (SCF), thrombopoietin (Tpo), and granulocyte colony-stimulating factor (G-CSF), were purchased from R&D Systems.

Antibodies.

Primary antibodies used for flow cytometry and cell sorting include mouse anti-human CD41-FITC or -APC, mouse anti-human CD42b-PE, rat anti-mouse CD41, mouse anti-human CD38-PE-Cy7 (eBioscience), mouse anti-human CD61-Alexa 488 (AbD Serotec), anti-Annexin V-PE (BD Biosciences), mouse antihuman CD34-PE (Invitrogen), and mouse anti-human SIRPa-PE (Santa Cruz). Phalloidin-TRITC was purchased from Invitrogen. Primary antibodies for Western blotting, immunoprecipitation (IP) and imaging include nonmuscle myosin-II (NMM-IIA) (Sigma), NMM-IIB (Cell Signaling Technology), β-actin and pTyr-specific (Santa Cruz) antibodies. Secondary antibodies include donkey anti-rabbit Alexa 594 or Alexa 488 (Invitrogen), anti-mouse or anti-rabbit HRP-conjugated IgG antibodies (GE Healthcare).

Human Hematopoietic Stem Cell Culture, Pharmacological Perturbation, and Ploidy Analysis.

Fresh purified bone marrow (BM)-derived humanCD34$^+$ cells were obtained from either the Penn Xenograft Core Facility or AllCells. Cells from at least 10 different donors were used in this study. Purity of the samples (>98%) was confirmed by flow cytometry with monoclonal antibody against human CD34 conjugated to phycoerythrin (PE). All experiments were performed in hematopoietic stem cell (HSC) expansion media (StemLine-II; Sigma) supplemented with 1× antibiotics, and the following human recombinant cytokines SCF (100 ng/mL) and Tpo (100 ng/mL). In some occasions, the media was also supplemented by G-CSF (100 ng/mL). All cytokines were purchased from R&D Systems. After cells were cultured for 4 days, they were treated with different doses of cellular contractility inhibitors, including (±)-blebbistatin (EMDBiosciences), reversine, ML-7, and Y-27632 (Sigma) for indicated durations of up to 3 days. Unfortunately, longer exposure to drug proves toxic even to polyploidy cells under the present culture conditions. Cells were then resuspended in PBS/2% FBS medium and subjected to ploidy analysis: cells were stained with CD41-FITC (BD Biosciences) at room temperature for 30 min, followed by Hoechst 33342 at 37° C. for 30 min. Then cells were stained with Annexin-V-PE (BD Biosciences) in the Annexin-V staining medium, followed by addition of 7-AAD. Stained cells were subjected to flow cytometric analysis (LSR-II; BD Biosciences): only viable cells (7-AAD$^-$ and Hoechst 33342$^+$) were analyzed for ploidy. Cells with the DNA content of 8 N or higher were considered polyploid. To quantify absolute number of polyploid cells, viable cell number was counted before flow cytometry by Trypan blue exclusion, and this number was multiplied by percentages of each DNA compartment and subpopulations. Each multiplied number was then normalized by initial cell input number before drug treatment in culture.

Plasmid Construction and RNA Nucleotides.

The original construct that contains GFP-fused human NMM-IIA heavy-chain sequence with the cytomegalovirus promoter was described previously (Wei et al., 2000, Mol Biol Cell, 11:3617-3627) and obtained from Addgene (GFP-NMM-IIA). Single and double point mutants Y277F and Y1805F were constructed previously (Tsai et al., 2008, J Cell Biol, 180:989-1003). A serine residue GFP-NMM-IIA point mutant S1943A was created by point-mutation, using the QuikChange II XL Site-Directed Mutagenesis Kit (Stratagene), according to the manufacturer's instructions, with the following primers:

```
                                      (SEQ ID NO: 1)
5'-GCCGGGGATGGCGCCGACGAAGAGG-3' (sense)

(SEQ ID NO: 2)
5'-CCTCTTCGTCGGCGCCATCCCCGGC-3' (antisense)
```

All mutant constructs were confirmed by sequencing. For NMM-IIB siRNA duplexes, the sequences were obtained (Bao et al., 2005, J Biol Chem, 280: 19594-19599) and were synthesized by Dharmacon, Inc., along with scrambled siRNA.

Cell Culture, Transfection, and Ploidy Analysis in COS-1 Cells.

COS-1 cells were obtained from ATCC and were maintained in high-glucose DMEM with 10% FBS. Lipofectamene 2000 was used for both siRNA knockdown of NMM-IIB and overexpression of NMM-IIA constructs, according to the manufacturer's instructions (Invitrogen), when cells were 5% to 10% and 60% to 70% confluent, respectively. Efficiency of NMM-IIB siRNA was confirmed to be >90%, as indicated by quantitative immunofluorescence analysis (FIG. 7D). For GFP-tagged NMM-IIA constructs, the transfection efficiency was about 30% to ~40%. For overexpression studies without siRNA, cells were supplemented with fresh medium 24 h after transfection, followed by culturing for 3 more days before ploidy analysis. For rescue studies, NMM-IIB siRNA was transfected and cultured for 2 d, followed by transfection of GFP-tagged NMM-IIA constructs. The medium was changed to fresh media, and cells were cultured for 3 additional days before the analysis. Ploidy analysis of adherent COS-1 cells was done by detachment of cells in the presence of PBS/10 mM EDTA/5% FBS at 37° C. for 5 min. After making a single-cell suspension with pipetting and filtering, cells were then labeled with Hoechst 33342 at 37° C. for 30 min. Cells were chilled on ice and 7-AAD was added. Only 7-AAD$^-$ (viable) and GFP (transfected) cells were analyzed for cellular ploidy.

In Vivo Transplantation Studies with Xenograft Models.

Eight- to 10-wk-old nonobese diabetic (NOD)/SCID/IL-2Rγ−/− (NSG) mice were obtained and maintained in-house at the Penn Xenograft Core Facility. Before transplantation (~24 h), mice received a sublethal dose of 320 cGy total body irradiation. Cultured human CD34$^+$-derived cells (0.5–3×10$^5$ uncultured BM CD34$^+$ equivalent) with or without drug treatment was suspended in 20 µL PBS and injected directly into the tibia. Peripheral blood (PB) was then obtained from the transplanted mice via retroorbital bleeding and human platelet quantification was done at indicated times. To calculate human platelet in NSG circulation, the total platelet concentration count was done by Hemavet (Drew Scientific), and 2 µL of PB per staining sample was washed in the presence of PGE1 inhibitor (Sigma) and resuspended in PBS. Cells were incubated with mouse Fc-blocker (BD Biosciences) for 5 min, followed by addition of mouse anti-human CD41-FITC and rat anti-mouse CD41-PE antibodies (eBioscience). After 30 min incubation at room temperature, cells were fixed by addition of 0.5% paraformaldehyde and analyzed by flow cytometry within 2 h. Platelets were gated on based on forward and side scatters, and at least 50,000 events were acquired. Human platelet concentration was obtained by multiplying the total platelet count by the percentage of human CD41-FITC of the total CD41$^+$ platelets (mouse plus human). Microscopic determination and isotype control with mixing known number of human platelets indicate the threshold detection limit of 0.001%. The total human platelet number in each transplanted NSG mouse was estimated by assuming that the average total mouse blood is ~1.5 mL (Riches et al., 1973, J Physiol, 228:279-284). All animal experiments were performed in accordance with institutional guidelines approved by the ethical committee from the University of Pennsylvania.

Functional Characterization of Megakaryocyte-Derived Platelets.

Platelets derived from megakaryocytes (MKs) in culture or from xenograft blood were isolated by density gradient separation, as previously published (Lambert et al., 2007, Blood, 110:1153-1160). For structural analysis of microtuble coils in platelets, platelet-sized isolate was fixed with 4% paraformaldehyde and immobilized on poly-D-lysine (100 µg/mL)-coated glass slides for 20 min, followed by permeabilization with 0.5% Triton-X in PBS. After samples were incubated with 1% BSA/PBS for 30 min to block nonspecific binding, cells were labeled with antihuman α-tubulin antibody overnight at 4° C., followed by secondary anti-mouse antibody (Alexa 488-conjguated) for 1 h at room temperature. A 60× oil lens was used to acquire images.

For platelet-spreading assays, platelet-sized isolate was resuspended in Tyrode's buffer supplemented with $Mg^{2+}$ and $Ca^{2+}$, and adhered on fibrinogen (100 µg/mL) or collagen-I (200 µg/mL)-coated glass slides for 45 min at 37° C. in the presence of indicated agonists. After washing out nonadherent fragments cells three times with Tyrode's buffer, cells were fixed with 4% paraformaldehyde, followed by immunofluorescence staining with anti-human CD61 antibody and phalloidin (F-actin).

For platelet-activation assays, platelet-sided fraction isolated from either MK culture or NSG blood was resuspended in Tyrode's buffer supplemented with $Mg^{2+}$ and $Ca^{2+}$, and incubated with indicated agonists for 15 min at 37° C., followed by staining with FITC-conjugated anti-human P-selectin or PAC-1 antibody (BD Bioscience), APC-conjugated anti-human CD41, and in the case of xenograft samples, PE-conjugated anti-mouse CD41 for 15 min at room temperature, followed by fixation with 1.5% paraformaldehyde. Antibody-stained samples were then analyzed by flow cytometry. Platelet number was evaluated by mixing each sample with a defined number (~10,000 beads per sample) of APC-conjugated beads (BD Bioscience). The number of platelets per sample was evaluated by: number of $CD41^+$ events/number of APC-bead events multiplied by total known number of APC-bead added per sample.

Micropipette Aspiration.

Cells from $BMCD34^+$, cultured in SCF and Tpo between 3 and 8 days, were treated with 20 µM blebbistatin for 30 min to 1 h, followed by micropipette analysis. Capillary tubes of 1.0-mm inner diameter (World Precision Instruments) were pulled into micropipettes using a Flaming-Brown Micropipette Puller (Sutter Instrument) and cut further using a deFonbrune-type microforge (Vibratome). The average micropipette diameter was around 3 µm. Micropipettes were attached to a dual-stage water manometer with reservoirs of adjustable height. Suction was applied by a syringe, and the corresponding pressure was measured by pressure transducer (Validyne), calibrated by a mercury U-tube manometer. Pressures for different experiments ranged from 0.5 to 20 kPa. In some cases, cells were labeled with a very low dose (10 nM) of fluorescent BODIPY-Taxol (Invitrogen) for 1 h at 37° C. to visualize the initial stage of microtubule polymerization during micropipette aspiration.

Construction of Collagen-Coated Gels with Different Matrix Elasticity.

Fifteen- to ~18-mm glass coverslips were treated in order with ethanol, RCA solution (1:1:3 for 15N $NH_4OH$:30% $H_2O_2$:$dH_2O$), methylene chloride, and 0.1% allyltrichlorosilane solution. To control the gel's stiffness, N,N' methylene-bis-acrylamide and the acrylamide solution was mixed at the ratio of 0.07%:3% for soft gels (0.3 kPa), or the ratio of 0.3%:8% for stiff gels (34 kPa), final concentrations in PBS. Approximately 25 µL of the mixed solution was polymerized on a coverslip with 10% ammonium persulfate and N,N,N',N'-tetramethylethylenediamine. During polymerization, gels were covered with another coverslip to obtain a uniform gel surface with the final thickness of ~100 µm. Different concentrations of collagen-I were then cross-linked with polymerized gels using sulfo-SANFAH (Pierce) by UV-crosslinking Thickness of gels and relative collagen concentrations were verified by confocal microscopy. It is assumed that most collagen from the solution was attached to gels (>70%). Collagen-coated gels were then treated with UV in PBS for at least 1 h before use in cell culture.

Preparation of Collagen Matrix Cultures.

Three-dimensional collagen gels embedded with cells were prepared as previously published (Rhee et al., 2007, Proc Natl Acad Sci USA, 104:5425-5430). BM-derived cells were added to the collagen solution prepared by neutralizing 2.0 mg/mL collagen-I (BD Biosciences) with HSC expansion media adjusted to appropriate the pH, so that cells could be embedded to the polymerized matrices ($1 \times 10^5$ cells/mL). Next, 200 µL of this collagen mixture was placed in a well of 24-well plate and incubated at 37° C. 5% $CO_2$ overnight before being formaldehyde-fixed and processed for microscopic analysis. Washing steps were done gently using pipette to minimize disturbance of gels. After completion of staining, matrices were released from the plate by gentle shaking and transferred to glass slides in mounting medium with either a spatula or gentle pipetting.

Adhesion Assay.

BM $CD34^+$-derived cells were cultured on collagen gel coverslips for 3 days. Each well was filled gently with PBS and the coverslip from each well was immobilized. The plate was then immersed in a bath filled with PBS and inverted for 30 min to detach nonadherent cells at 1 g. After cell detachment, the plate was recovered and each coverslip was immediately fixed with 4% paraformaldehyde, followed by staining with F-actin and Hoechst 33342. Viable adherent cells were counted by looking at intact nuclear morphology and positive F-actin staining. The total cell number per well at day 3 in culture before inversion was estimated from a separate culture plate, in which all cells were detached by 10 mM EDTA/5% FBS solution for 5 min at 37° C. and were counted by hemocytometer. The total adherent cell number was divided by the total cell number to estimate the percentage of adherent cells.

Immunoprecipitation and Western Blotting.

In general, cells were washed with ice-cold PBS and lysed on ice with lysis buffer (150 mM sodium chloride, 1% Nonidet P-40, 1% protease inhibitor mixture, 1 mM activated sodium orthovanadate, 50 mM Tris at pH 8.0) for 30 min. For immunoprecipitation (IP), 30 mM of pervanadate solution was prepared by mixing sodium orthovanadate with $H_2O_2$ for 15 min at room temperature. At least $1 \times 10^7$ THP-1 cells were treated with pervanadate with or without blebbistatin at 37° C. for 15 min. Cells were then washed, lysed, and whole-cleared lysate was mixed with anti-NMM-IIA antibody at 4° C. overnight, followed by incubation with Protein G (Invitrogen) for 1 h. For Western blot, whole lysate or IP proteins were separated on 4% to 12% SDS/PAGE gels (NuPAGE 4-12% Bis-Tris, Invitrogen). The proteins were then transferred to a polyvinylidene fluoride (PVDF) membrane with an iBlot Gel Transfer Device (Invitrogen), followed by blocking with 5% nonfat dry milk solution for 1 h. Incubation with primary antibodies was done at 4° C. overnight with 1:1,000β-actin, 1:250 pTyr, and 1:1,000 NMM-IIA antibodies. After washing, the membrane was incubated with 1:2,500 anti-rabbit and 1:1,000 anti-mouse HRP-conjugated IgG antibodies at room temperature for 1 h. The blot was developed with ChromoSensor (GenScript) for 5 min, followed by digital scanning to perform densitometry analysis by ImageJ (National Institutes of Health).

Live Cell Imaging Analysis.

At least 20,000 BM CD34+-derived cells were put into Ibidi µ-slide VI (Ibidi GmbH) in cell culture medium. Analysis was done in an insulated chamber maintained at 37° C., 5% $CO_2$. A series of images were collected every 5 min for 18 to ~24 h with an Olympus IX70 inverted microscope with 300 W Xenon lamp illumination using 10× or 20× objectives under bright field. Image stacks were further analyzed by ImageJ to analyze cell division with or without blebbistatin treatment.

Immunofluorescence Analysis and Quantification.

Cells on coverslips were fixed with 4% paraformaldehyde, followed by permeabilization with 0.5% Triton X-100 in PBS for 15 min and blocking with 1% BSA in PBS for 30 min. Samples were then stained with primary antibodies (1:100 for all antibodies used) overnight at 4° C. After washing, staining with appropriate Alexa-conjugated secondary antibodies (1:400) was performed for 45 min at room temperature. Cells were washed three times with PBS and mounted in ProLong Gold antifade medium (Invitrogen). Samples were then analyzed by fluorescence microscopy. For quantitative analysis, pictures from each experiment were taken under a defined set of exposure times on the same day with 40× objectives. Intensity of labeled NMM-II proteins for each cell was analyzed by ImageJ by subtracting a background, defining a threshold of cell boundary, followed by calculation of mean intensity. At least 10 images from each experiment were analyzed from three independent experiments. For proplatelet quantification, the process length from each cell was measured by manual tracing with ImageJ. Only processes above detection limit (≥1 µm in length from cell body) were considered for statistical analysis.

Visualization of Lipid "Demarcation" Membrane.

Lipid "demarcation" membrane of MKs and COS cells was visualized as described previously (Mahaut-Smith et al., 2003, Biophys J, 84:2646-2654). Briefly, cells stained with Hoechst 33342 were resuspended in PBS with 20 µM of a reversible styryl dye, FM 2-10 (Invitrogen). Cells were stained with the dye at room temperature for at least 20 min before visualization under fluorescent microscope with 488-nm excitation length. The images were obtained within 1 h of staining, as prolonged staining leads to penetration of the dye into the cytoplasm.

Cell Sorting.

Figure 5:
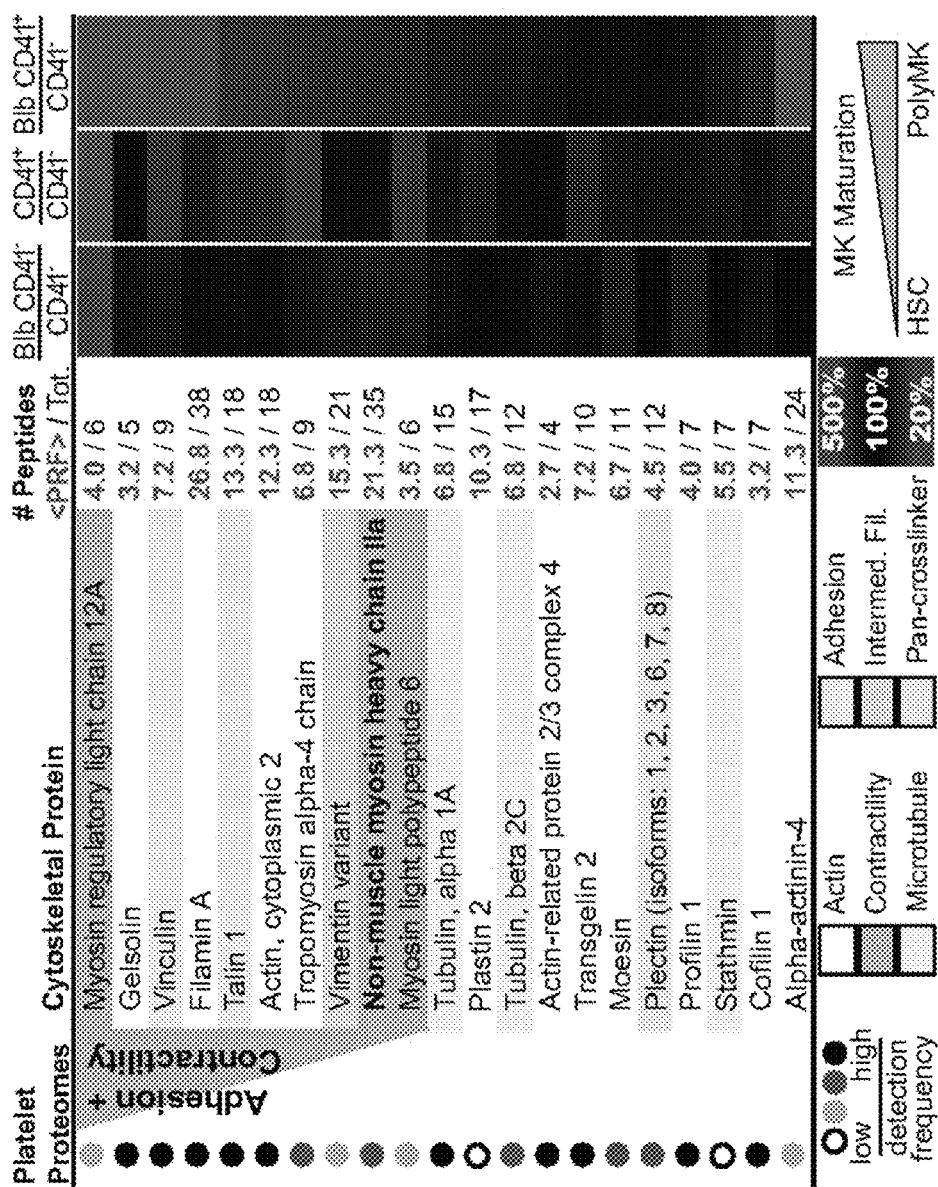
FIG. 5 illustrates the label-free MS quantitation of myosin-inhibited cytoskeletal proteome. CD34$^+$ cells were treated with blebbistatin for 3 d. The viable cell fraction (Annexin-V$^-$ and 7-AAD$^-$) of CD41$^+$ MKs was isolated by sorting, followed by MS. The first column summarizes detectability in prior literature on platelets. <PRF> refers to the number of peptides retained in propotional peak fingerprint for protein quantitation, whereas "Total" refers to all peptides detected.

BM CD34+-derived cells at day 7 were stained with CD41-FITC at room temperature for 1 h, followed by with Annexin-V-PE (BD Biosciences) in the Annexin-V staining medium for 15 min. Cells were then resuspended in 2% FBS/PBS with 7-AAD. Viable HSC-containing cell populations and differentiated MK lineages at day 7 in culture were separated on the basis of CD41 surface expression by cell sorting performed on a FACS Vantage machine (Becton Dickinson). Dead cells stained with 7-AAD and Annexin-V were excluded from sorting. Sorted cells were directly processed for mass spectrometry (MS) analyses (FIG. 5).

Proportional Peak Fingerprints (ProPF) in Label-Free Mass Spectrometry.

Figure 13:
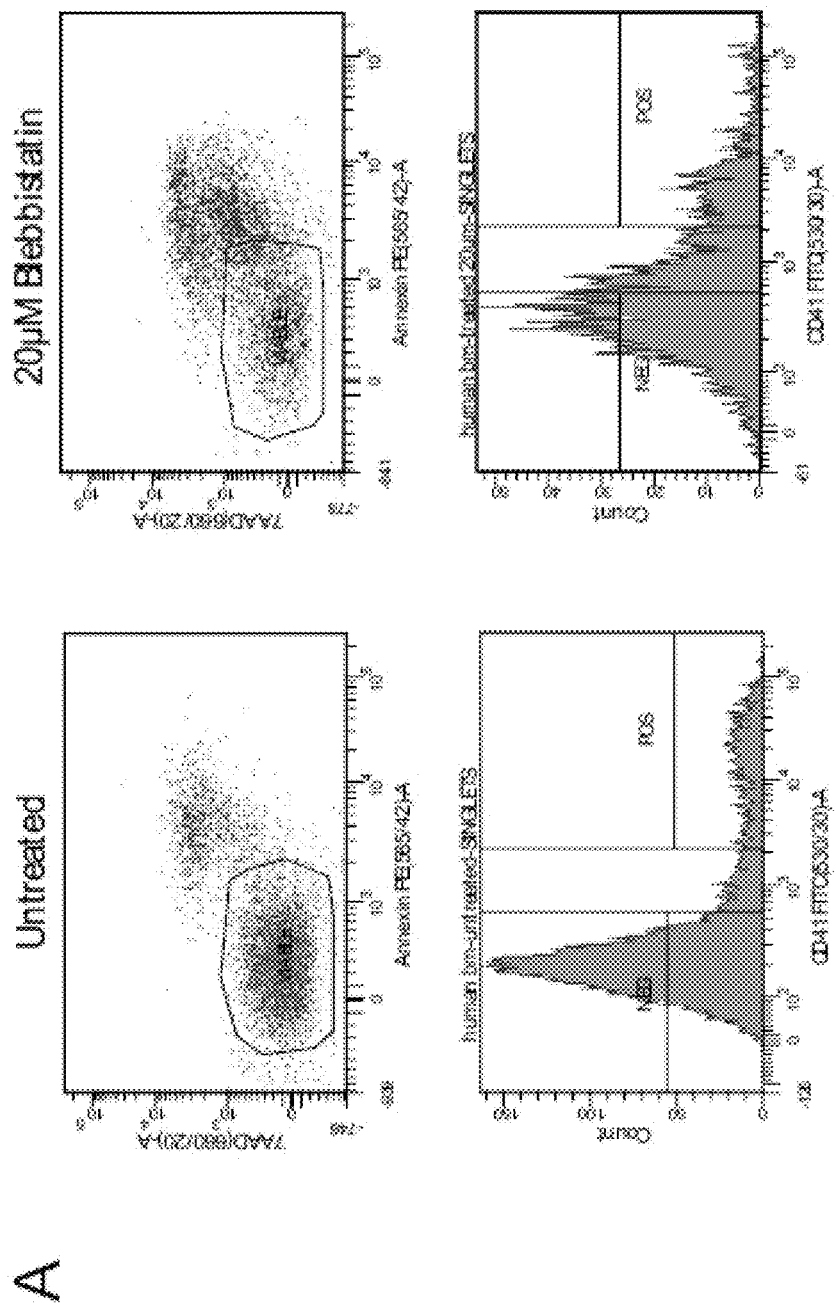
FIG. 13, comprising
Figure 13:
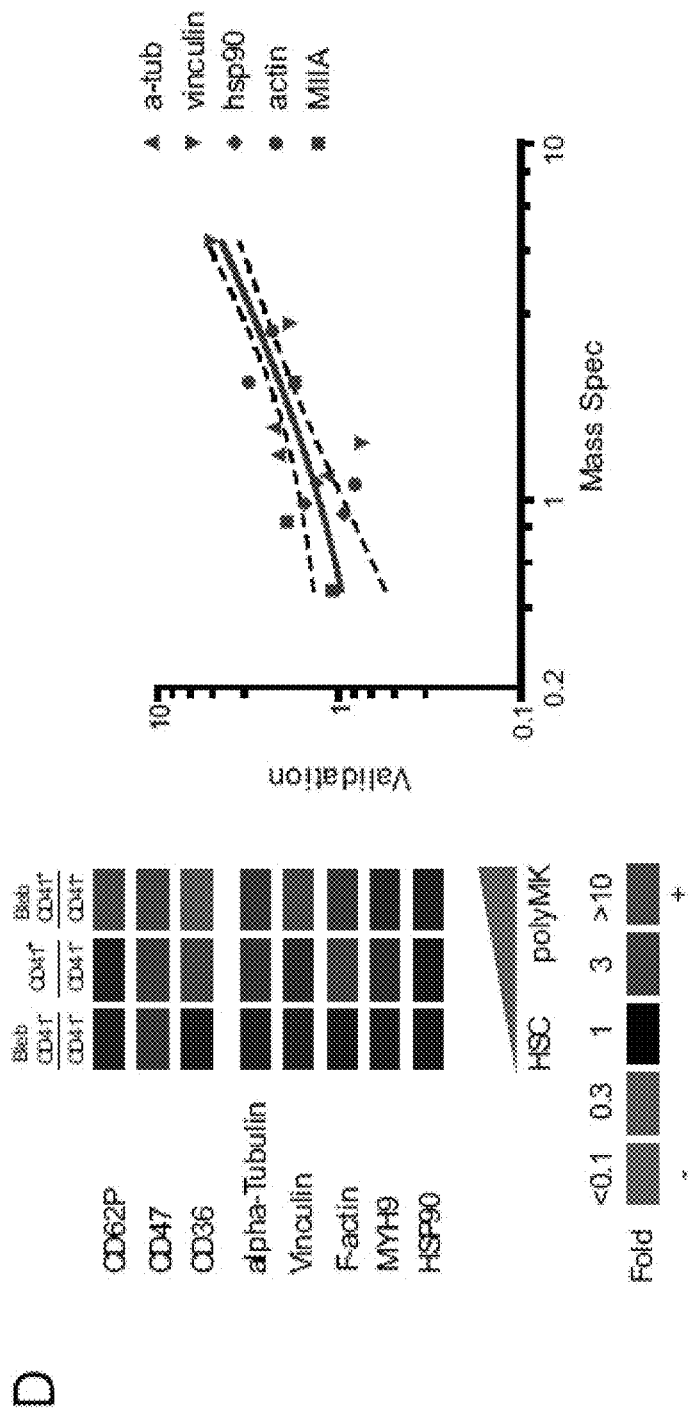

Samples were prepared for mass spectrometry by gel-free (Wiśniewski et al., 2009, Nat Methods, 6:359-362) or in-gel digestion methods. For in-gel digestion, sections of excised polyacrylamide gel were washed (50% 0.2M ammonium bicarbonate (AB) solution, 50% acetonitrile, 30 min at 37° C.), dried by lyophilization, incubated with a reducing agent (20 mM Tris(2-carboxyethyl)phosphine in 25 mMAB solution at pH 8.0, min at 37° C.), and alkylated (40 mM iodoacetamide in 25 mM AB solution at pH 8.0, min at 37° C.). The gel sections were dried by lyophilization before in-gel trypsinization (20 µg/mL sequencing grade modified trypsin in buffer as described in the manufacturer's protocol (Promega Corp.), 18 h at 37° C. with gentle shaking) Before analysis, peptide solutions were acidified by addition of 50% digest dilution buffer (60 mM AM solution with 3% methanoic acid). Peptide separations (5-µL injection volume) were performed on 15-cm analytical columns (75-µm inner diameter) packed with 5-µm C18 beads using a nanoflow high-pressure liquid chromatography system (Eksigent Technologies), which was coupled online to a hybrid LTQ-Orbitrap mass spectrometer (Thermo Fisher Scientific) via a nano-electrospray ion source. The LTQOrbitrap was operated in the data-dependent mode to automatically switch between full-scan MS (m/z=350-2000 in the orbitrap analyzer, with resolution of 60,000 at m/z 400) and the fragmentation of the six most-intense ions by collision-induced dissociation in the ion trap mass analyzer. Raw MS data were processed using Elucidator (version 3.3, Rosetta Biosoftware). The software was set up to align peaks in data from samples derived from the same ranges of molecular weight. Peptide and protein annotations were made using SEQUEST (Thermo Fisher Scientific) with full tryptic digestion and up to two missed cleavage sites. Peptide masses were selected between 800 and 4,500 amu, with peptide mass tolerance of 1.1 amu and fragment ion mass tolerance of 1.0 amu. Peptides were searched against a database compiled from UniRef100 human, plus contaminants and a reverse-decoy database. Search results were selected with a deltaCn filter of 0.05 and mass error better than 10 ppm. Data attained from different slices of the same gel lane was combined by summing ion currents on a peptide-by-peptide basis based upon the peptide sequence annotation. Ion currents of oxidized peptides were summed with their parent peptide. When considering a total ion current, only signals from annotated peptides were summed. Label-free relative peptide quantitation was performed on proportional peak fingerprints (ProPF) of proteins with in-house software coded in Mathematica (Wolfram Research). Datasets were normalized against optimized peptide sets that were found to be invariant between experimental conditions. Proteomes from primary MKs were analyzed using this unique method and a selected group of proteins were validated by antibodies (FIG. 13D). COS cells transfected with GFP-NMM-IIA and siRNA NMM-IIB knockdown were also analyzed by the method, and show increased NMM-IIA expression by 17-fold and partial knockdown (~40%) of NMM-IIA compared with cells transfected with GFP and scrambled siRNA. There was minimal perturbation to other proteins detected. The analysis of two different cell types indicates that the label-free method is capable of quantifying protein levels in a reliable manner.

Statistical Analyses.

All statistical analyses were performed using GraphPad Prism 4. Unless otherwise noted, all statistical comparisons were made by unpaired two-tailed Student t test and were considered significant if $P<0.05$. All dose-response data were fitted to sigmoidal dose-response with variable slope with the x axis in a log scale.

The results of the experiments are now described.

Myosin-II Inhibition Increases MK Polyploidy and Membrane Fragmentability.

Mature polyploid MKs are increased in number by 3- to ~10-fold by blebbistatin, without affecting total MKs. Polyploid MKs are CD41 (CD41: $\alpha_{2b}\beta_3$-integrin) with a high multiple of chromatin pairs per cell (≥8 N) (FIG. 1C). Sustained application of drug also depletes the pool of MK progenitors, with responses that are all highly cooperative in drug concentration (Hill exponents: n~7) with similar inhibition constants $K_i$ (~7.6 µM). $K_i$ is approximately twofold higher than blebbistatin inhibition of purified NMM-IIA (Straight et al., 2003, Science, 299:1743-1747), but the relatively small difference in $K_i$s likely reflects the shift toward higher cooperativity in cell division. Importantly, polyploidization upon sustained inhibition of NMM-II is observed in both human-derived hematopoietic THP-1 cells and monkey-derived epithelial COS-1 cells (FIGS. 7A and 7B). THP-1 cells express NMM-IIA primarily (Tsai et al., 2008, J Cell Biol, 180:989-1003), and lentiviral-knockdown using shRNA also increases polyploidy (FIG. 7C). COS-1 cells express NMM-IIB almost exclusively, and knockdown by siRNA transfection likewise increases polyploidy (FIG. 7D). Polyploidy is therefore not a pharmacological artifact of blebbistatin.

To investigate the additional role of myosin in membrane integrity under shear, cells were subjected to micropipette aspiration with stepwise decreases in pressure using pipettes similar in diameter to human capillaries (~3 µm). The cell and its membrane shear and flow into the micropipette, resembling, in shape, elongated proplatelets. After just 30 min of blebbistatin, cells are approximately four fold more compliant (FIG. 1D and FIG. 8A), and 40% of treated cells also rapidly fragment to average sizes similar to those of large human platelets (3 to ~4 µm). Platelets are now known to be generated by shearing of proplatelets (Thon et al., 2010, J Cell Biol, 191:861-874). Further, no fragmentation was observed in untreated cells. Projection lengths up to the point of divergent fragmentation vary from 10 to ~20 µm, which is similar to in vivo fragmented proplatelet lengths of ~14 µm (Junt et al., 2007, Science, 317:1767-1770). Fragmentation stresses here correspond to effective membrane tensions of ~1 mN/m, which is 10-fold lower than cell membrane lysis tensions (Hategan et al., 2003, Biophys J, 85:2746-2759). Platelets not only maintain membrane integrity but also exhibit characteristic structures, such as cortical, coil-like microtubules (MTs). Thus, primary MKs and MEG01 cells (an MK-like line) were aspirated after labeling with a very low and cell-viable dose of fluorescent-Taxol (10 nM) (Guminski et al., 2001, Cancer Chemother Pharmacol, 48:229-234). Even at a 1,000-fold higher dose of Taxol, proplatelets are known to extend (Italiano et al., 1999, J Cell Biol, 147:1299-1312). In slow aspirations, MT-coils were visualized extending into the projection tips at ~0.7 µm/min (FIG. 8) and bundles of MTs appeared more often than individual MTs, all consistent previously reported rates and structures (Italiano et al., 1999, J Cell Biol, 147:1299-1312). Although final structures are rate- and force-dependent as transition rates~exp(force) (Hategan et al., 2003, Biophys J, 85:2746-2759), the basic findings described herein indicate that both nonlytic fragmentation under shear and MK polyploidization is promoted in part by myosin inhibition, even with microtubule polymerization as reported (Italiano et al., 1999, J Cell Biol, 147:1299-1312).

Soft Matrix with Low Collagen Maximizes MK Polyploidy.

Cell interactions with extracellular matrix (ECM) are unavoidable in vivo, and such interactions are modulatory, as found originally with substrate-assisted cytokinesis of myosin-null *Dictyostelium* (De Lozanne et al., 1987, Science, 236:1086-1091). Furthermore, it seems inevitable in BM (FIG. 1A) that migrating MKs encounter gradients in both tissue elasticity and collagen density (Nilsson et al., 1998, J Histochem Cytochem, 46:371-377). The bone surface is high in collagen-I (collagen$^{hi}$) and stiff, with an estimated elasticity $E_{ECM}$ for osteoid of ~34 kPa (Engler et al., 2006, Cell, 126:677-689), whereas the marrow space is collagen$^{lo}$ and very soft, with approximated $E_{ECM}$=0.3 kPa (Winer et al., 2009, Tissue Eng Part A, 15:147-154). MKs express two collagen receptors: GPVI and integrin-α2β1 (Zutter et al., 1995, Blood, 86:3006-3014; Lagrue-Lak-Hal et al., 2001, J Biol Chem, 276:15316-15325). Previous results indicate that collagen suppresses maturation of MKs in vitro (Pallotta et al., 2009, PLoS ONE, 4:e8359), and so it was examined if a low collagen, compliant ECM favors MK polyploidization. CD34$^+$ cells were cultured on polyacrylamide gels of controlled stiffness with different collagen concentrations per previous studies with BM-derived mesenchymal stem cells (Engler et al., 2006, Cell, 126:677-689), which showed matrices as soft as muscle are myogenic, whereas matrices that are stiff like osteoid induce osteogenesis.

At low collagen (2 ng/cm$^2$) and on soft gels (0.3 kPa), polyploid MK increase (by 50%) compared with stiff gels (34 kPa), indicating roles of matrix elasticity in regulating polyploidy (FIG. 2A). This effect is maintained over a range of collagen concentrations (2-200 ng/cm$^2$) (FIG. 2B), but is abolished by blebbistatin except for the lowest collagen (2 ng/cm$^2$). Above a matrix ligand threshold, cells can sense elasticity via myosin (plus other mechanisms, per FIG. 2A). These processes are fully decoupled in suspension cultures (FIG. 1C).

Because adhesion opposes polyploidy of myosin-null amoeba (Zang et al., 1997, Mol Biol Cell, 8:2617-2629), it was further tested—by a simple inversion of submerged cultures (1 g for 30 min)—whether increased adhesion could explain reduction in polyploid MK numbers on stiff gels. Although standard plastic-dish cultures under serum-free conditions show no attachment and are thus suspension cultures, 50% more cells remained anchored to stiff matrices versus soft matrices, with the greater adhesion depending on active NMM-II (FIG. 2C). Nonetheless, adhesion to all collagenous gels with or without myosin inhibition was at least 20-fold higher than the near-zero attachment to plastic. Understandably, polyploidy increases (almost twofold) with increasing collagen concentration on stiff gels as cells anchor so strongly that they cannot migrate away to complete division (FIG. 2D). Migration is well-known to be biphasic in adhesive ligand, with low ligand promoting migration but high ligand leading to immobilization. Matrix ligand density and stiffness therefore factor in as cells complete cytokinesis by crawling apart, even when myosin is ablated (De Lozanne et al., 1987, Science, 236:1086-1091).

Soft 2D Collagenous Matrices Are Better than Stiff or 3D.

Figure 9:
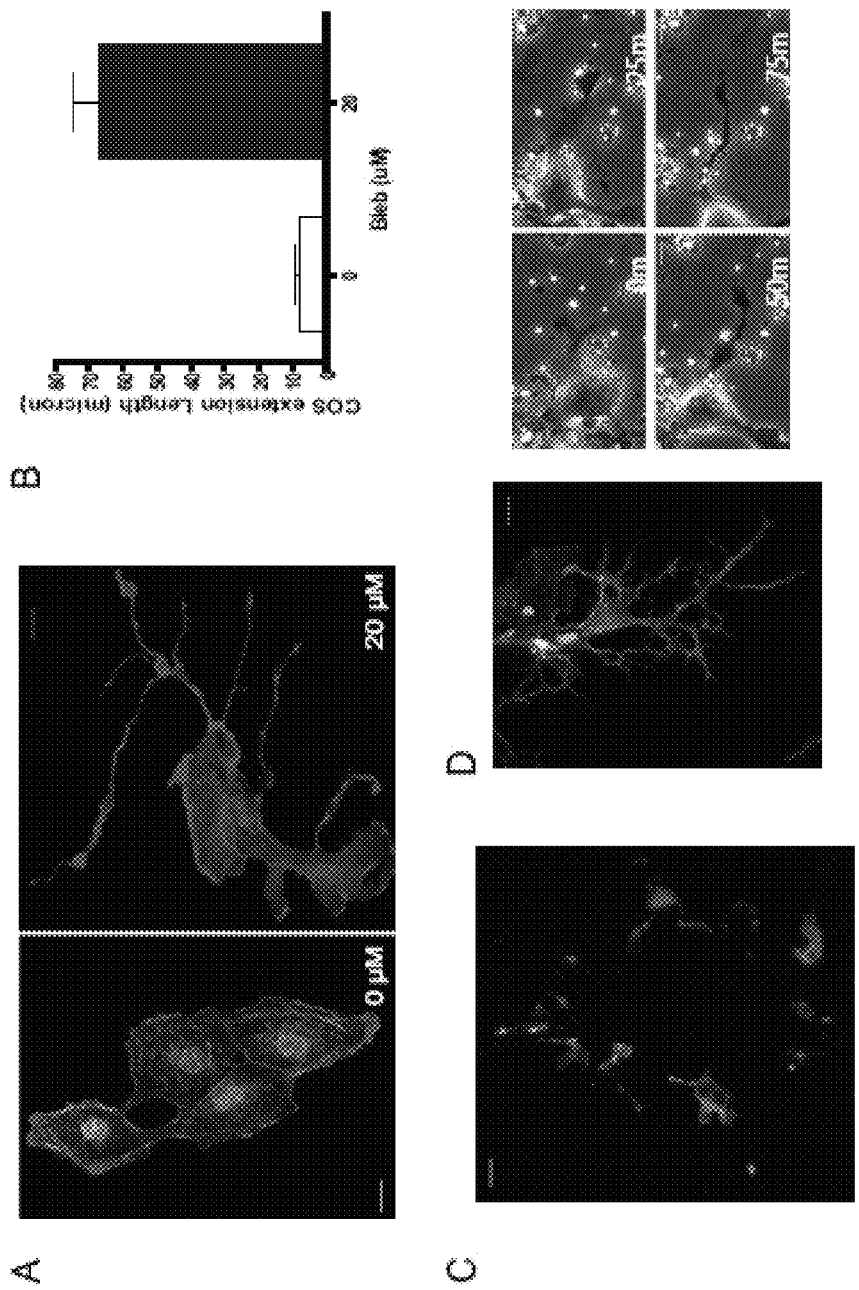
FIG. 9, comprising
Figure 9:
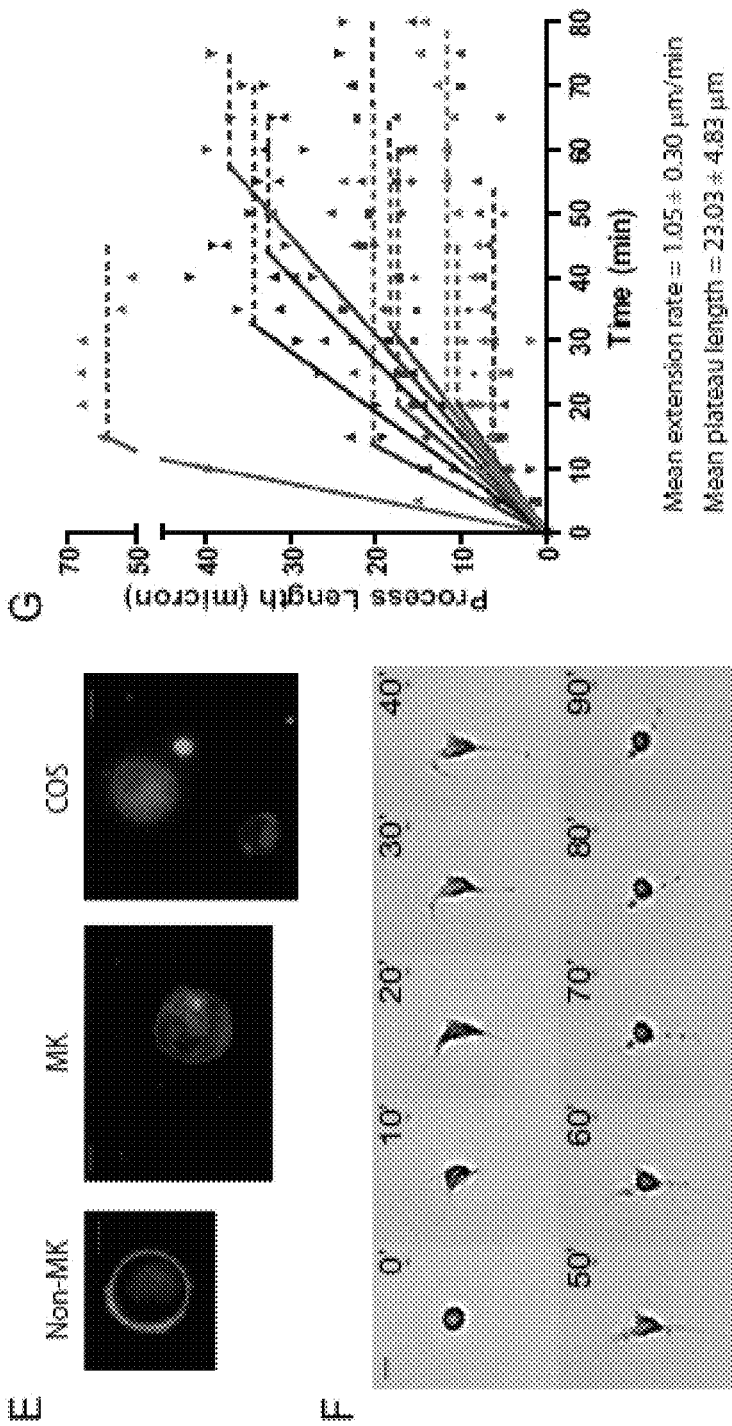

For some cells, NMM-II inhibition is known to cause a dendritic morphology on rigid substrates (Straight et al., 2003, Science, 299:1743-1747). This is observed for the COS-1 cell line as well (FIG. 9A-9D). These cells also stain positive with a dye for lipid "demarcation" membranes, a marker of polyploid MKs, even though some major differences are expected between lineages (FIG. 9E)(Mahaut-Smith et al., 2003, Biophys J, 84:2646-2654). The morphology effects are reminiscent of blebbistatin, causing an increased number of MKs with proplatelet extensions when cells are grown on plastic (Eckly et al., 2010, J Thromb Haemost, 8:2243-2251; Chen et al., 2007, Blood, 110:171-179). Indeed, an approximately threefold increase in mean length of proplatelet extensions was found under such conditions (FIG. 2E). Live imaging shows the average proplatelet extension velocity is ~1 µm/min, consistent with a previous study (Thon et al., 2010, J Cell Biol, 191:861-874) (FIGS. 9F and 9G).

Soft collagenous gels—in both 2D and 3D—facilitate proplatelet extensions compared with stiff gels (FIG. 2E). Blebbistatin has a considerable additive effect only with 2D soft matrices, with the drug having no effect on cells in 3D collagen gels or on stiff, osteoid-like matrices. While not wishing to be bound to any particular theory, perhaps the major difference between 2D soft and pure 3D matrix is the high density of ligand in 3D, and as with polyploidy, high collagen tends to anchor and suppress any effect of blebbistatin (FIG. 2D).

Myosin-II Heavy Chain Is the Best Target for MK Maturation.

Figure 10:
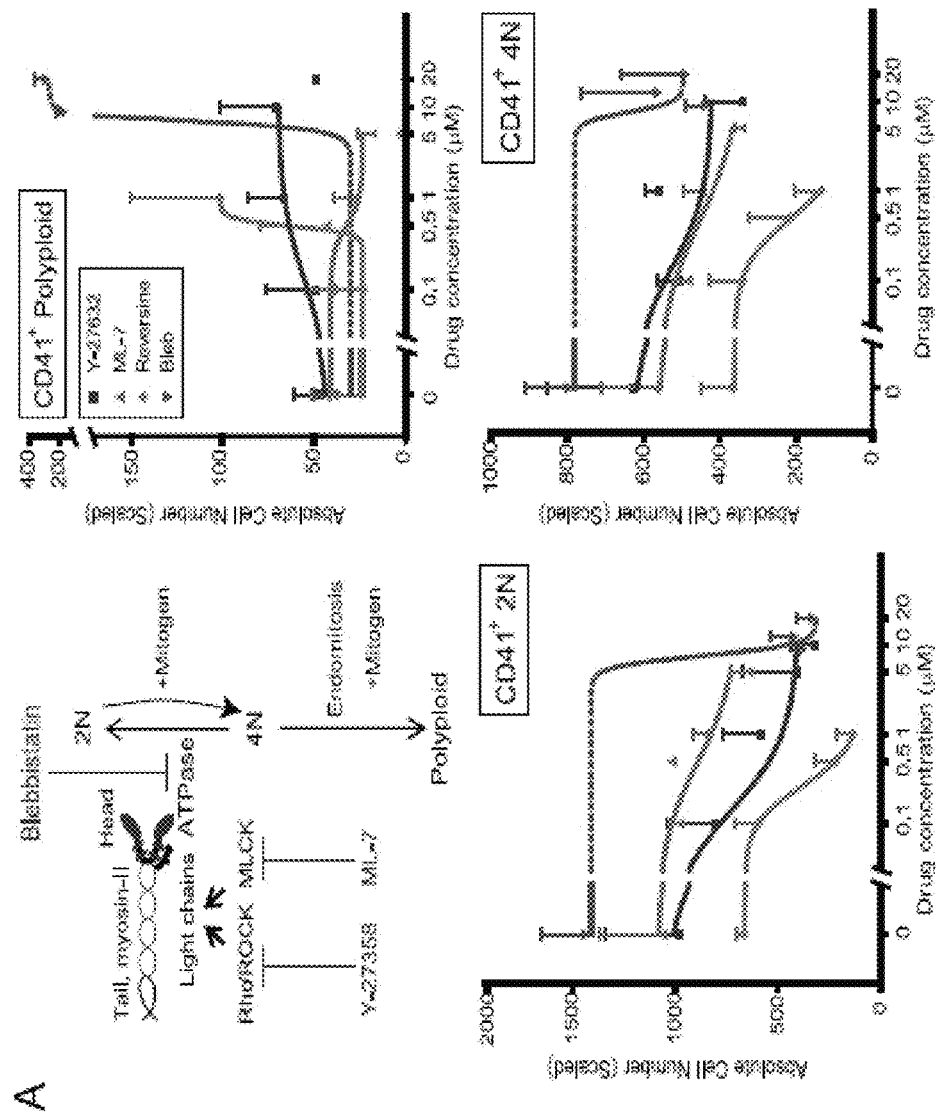
FIG. 10, comprising
Figure 10:
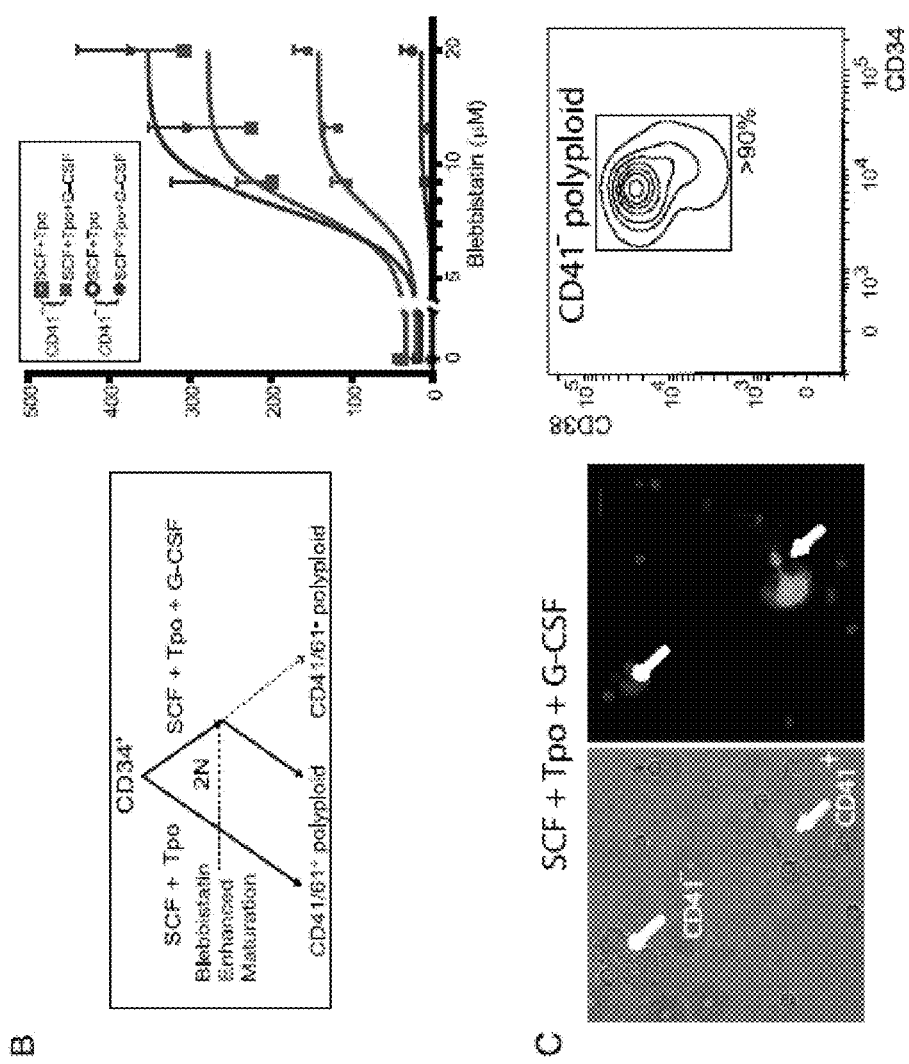

For drug treatment times much shorter than the doubling time (~18 h), cells continue to divide and a low number of polyploid MKs are generated. For longer treatment times, however, division is indeed inhibited and more polyploid MKs are generated (FIG. 3A). Polyploid cell numbers grow exponentially with duration of drug exposure, and the doubling time for polyploidization proves consistent with drug-free cell proliferation. Other contractility inhibitors are much less effective (FIG. 10A). In addition, stem-cell factor (SCF) and thrombopoietin (Tpo) favor MKs, but addition of G-CSF plus blebbistatin produces polyploid $CD41^-$ cells (FIGS. 10B and 10C), and time-lapse imaging shows most cells reverse cytokinesis (FIG. 3B). Restriction of endomitosis to MKs thus suggests lineage-specific signaling to myosin.

Phospho-Regulation of NMM-IIA and Polyploidy.

Figure 4:
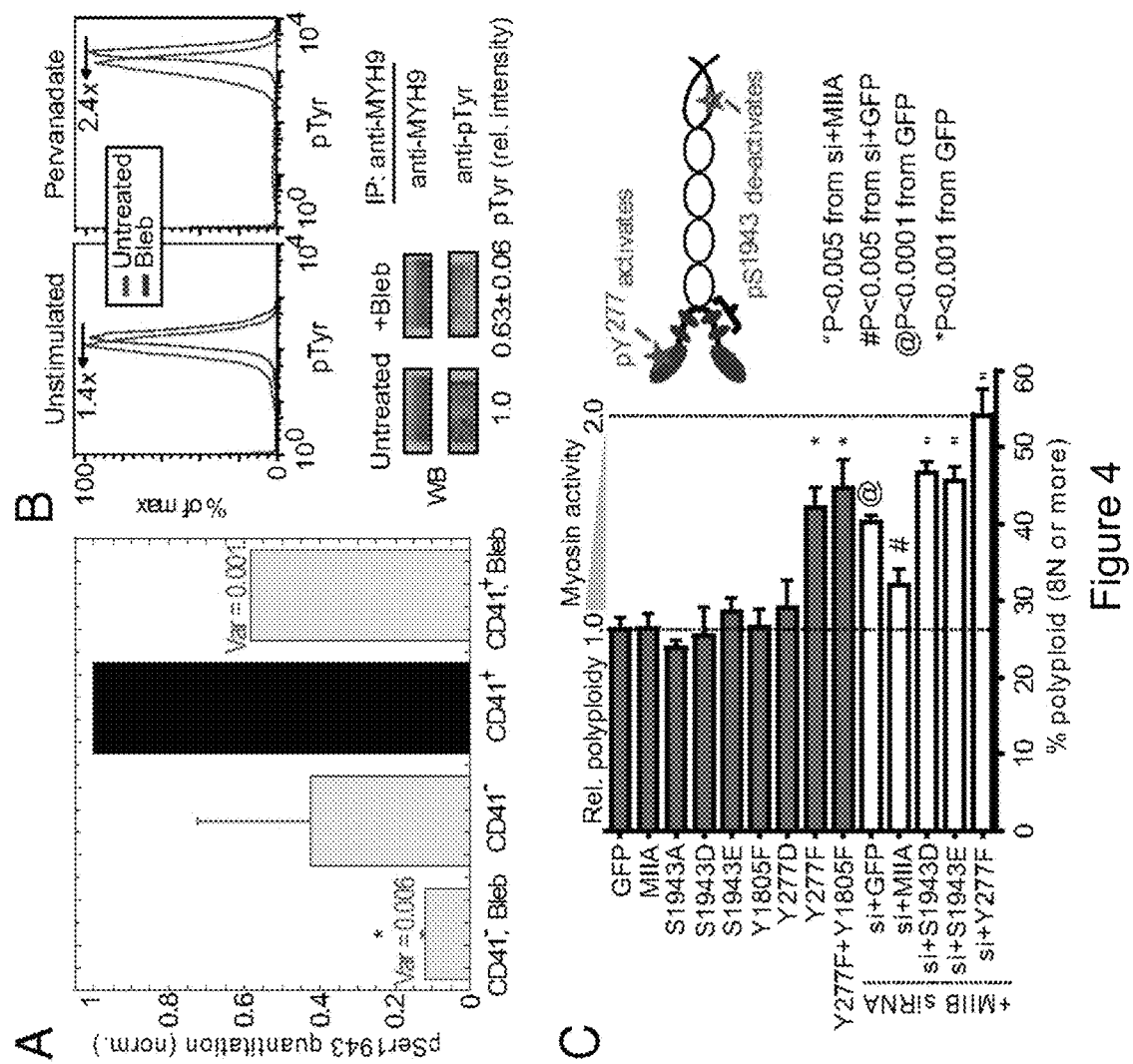
FIG. 4, comprising
Figure 11:
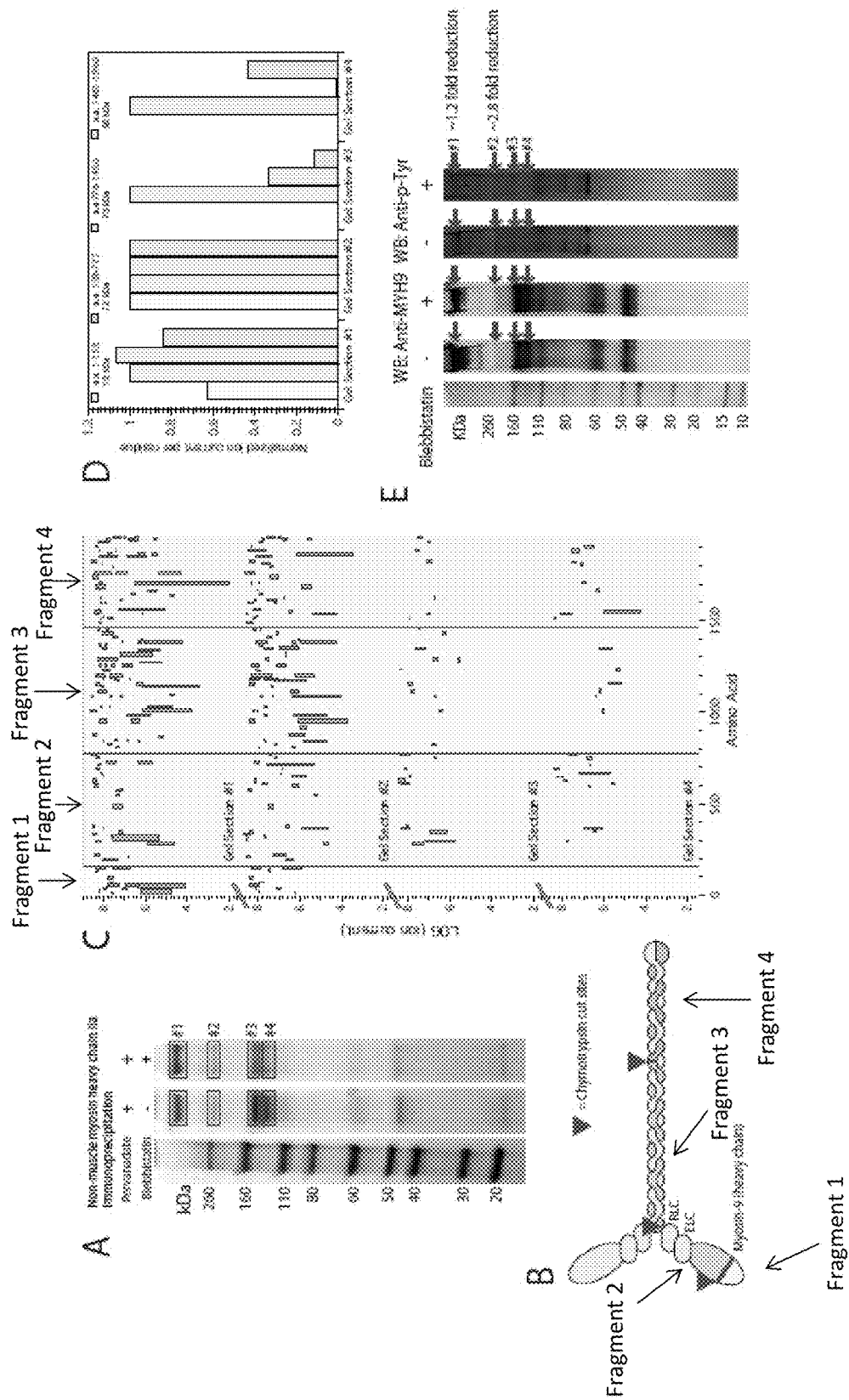
FIG. 11, comprising
Figure 12:
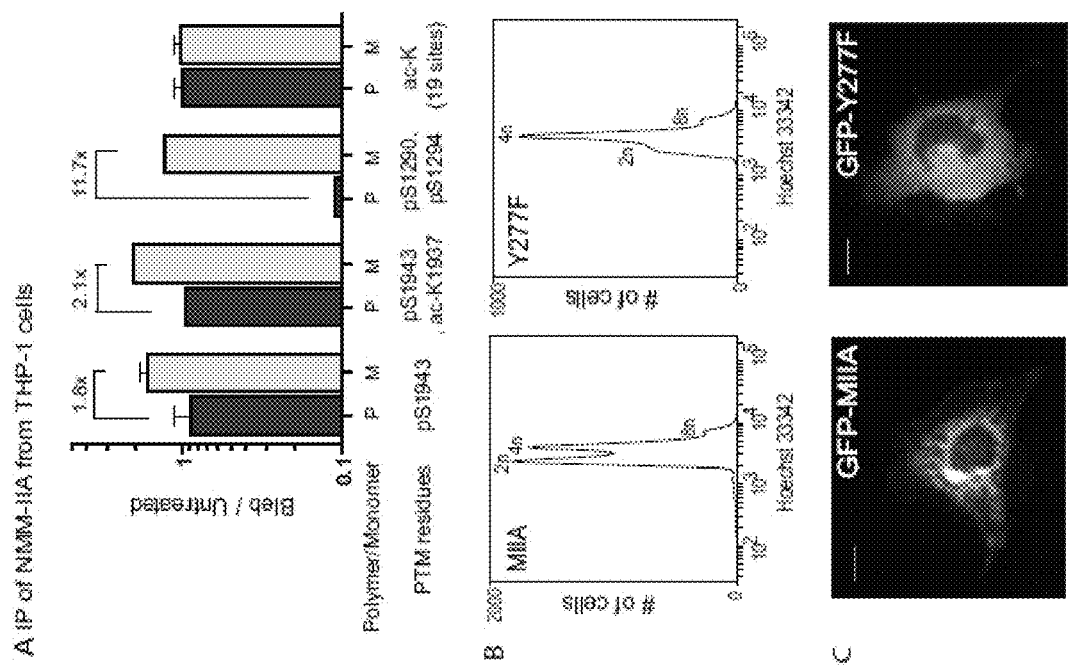
FIG. 12, comprising

NMM-II is of course abundant in platelets as well as MKs (Maupin et al., 1994, J Cell Sci, 107:3077-3090), but phospho-regulation of myosin heavy chain remains a topic of active study. Phosphorylation of S1943 is downstream of EGF receptor, inactivates myosin in epithelial cells, and impacts cell motility (Dulyaminova et al., 2007, Mol Biol Cell, 18:3144-3155). PDGF is one known ligand of EGF receptor (Saito et al., 2001, Mol Cell Biol, 21:6387-6394) and reportedly increases the number of MK progenitors (Su et al. 2001, Bone Marrow Transplant, 27:1075-1080). Mass spectrometry (MS) analyses of primary cells revealed approximately eightfold more phospho-S1943 in MKs vs. non-MK ($CD41^-$) cells (FIG. 4A), suggesting myosin inactivation accompanies MK differentiation. THP-1 cells immunoprecipitated with an antibody against NMM-IIA (FIG. 11) show blebbistatin increases phospho-S1943 when NMM-IIA is a detergent-soluble monomer rather than polymer (FIG. 12A). This finding is consistent with pSer-deactivation of myosin through inhibition of polymerization (Dulyaminova et al., 2007, Mol Biol Cell, 18:3144-3155).

Phosphorylation of Y277 has been implicated in B-cell function (Baba et al., 2003, Biochem Biophys Res Commun, 304:67-72), and phosphorylation of both Y277 and Y1805 activates myosin for phagocytosis by macrophages (Tsai et al., 2008, J Cell Biol, 180:989-1003). Because inhibition or knockdown of NMM-IIA in THP-1 cells caused a major increase in polyploidy (FIG. 7A), pTyr was examined in THP-1 and it was found that blebbistatin decreases pTyr levels under both basal and phosphatase-inhibited conditions. The difference is apparent in NMM-IIA's head plus proximal tail (a 150-kDa fragment) as characterized by immunoprecipitation (IP) (FIG. 4B) followed by detailed MS analysis (FIG. 11). Most tryptic peptides from the IP were from NMM-IIA. Myosin inhibition thus feeds back into signaling pathways.

Given the opposite roles of tyrosine (activating) and serine (de-activating) phosphorylation in modulating myosin activity, it was examined as to which phospho-sites in NMM-IIA might regulate ploidy by taking advantage of the easily transfectable COS cell lines that were previously used to study roles of NMM-II isoforms in cytokinesis. Because inhibition or knockdown of NMM-IIB in COS-1 cells increases polyploidy (FIG. 7B), NMM-IIA heavy chain phospho-mutants were expressed in native COS-1 and in the knockdowns (FIG. 4C). The head mutant Y277F increases the number of polyploid cells by approximately twofold (FIG. 12B), but phospho-mimetic mutant Y277D abolishes this effect. The pTyr mutant Y1805F in the tail also has no effect on ploidy, but the double mutant Y277F-Y1805F has the same effect on polyploidy as the head mutant. Knockdown of NMM-IIB with siRNA (FIG. 7D) shows the expected trends: polyploidy of GFP-transfection controls exceeds native levels, whereas wild-type NMM-IIA rescues partially with suppression of polyploidy. The Y277F mutant acts as a dominant negative (on residual NMM-IIB) and produces the highest levels of polyploidy, with 50% of cells showing ≥8 N. Overexpression of phospho-mimetic serine mutants of NMM-IIA, S1943D and -E, also prevents significant rescue of polyploidy, suggesting pS1943 functionally regulates myosin activity and ploidy. Visualization of the various GFP-NMM-IIA constructs shows the wild-type to be structured in cells, perhaps like stress fibers, but the Y277F mutant is far more diffuse (FIG. 12C). The results thus identify at least two specific signaling targets in myosin heavy chain that can regulate polyploidization, thereby implicating upstream signaling pathways in the marrow's perivascular niches for MKs.

Proteomic Profile of Blebbistatin-Treated MKs is Platelet-Like.

Because blebbistatin promotes maturation of $CD41^+$ cells in terms of ploidy and proplatelets, the proteomic profile of drug-treated cells might be expected to better approximate that of platelets, which have been extensively profiled. Using a unique label-free analysis of proteomes based on proportional peak fingerprints (ProPF) and motivated by the reported up-regulation in MKs of 22 actin cytoskeleton genes, five α- and β-tubulin isoforms, and just one down-regulated actin cytoskeletal gene (Raslova et al. 2007, Blood, 109:3225-3234), all cytoskeletal proteins were quantified, for which three or more tryptic peptides were detected in four distinct cell lysates: $CD41^-$, $CD41^+$, drug-treated, and not drug-treated (FIGS. 13A and 13B). $CD41^-$ cells include many hematopoietic cells that are $CD34^{hi}$, a marker of HSCs and progenitors of various lineages (FIG. 13C). Normalization to untreated $CD41^-$ cells shows blebbistatin has little effect, increasing expression modestly of only 20% of the indicated proteins (FIG. 5). In contrast, $CD41^+$ cells show considerable up-regulation: 50% of detected proteins in untreated samples and 75% in treated samples are up. This finding suggests an increasing level of differentiation especially in contractility with heavy and light myosin-II chains, and also adhesion linkers talin and vinculin. Tubulin α- and β-isoforms are also slightly up and to a similar extent as expected of heterodimers. Validation of the proteomics with antibodies against key proteins, including NMM-IIA and vinculin (FIG. 13D), proved consistent with mRNA up-regulation of NMM-IIA and vinculin in MKs (Raslova et al., 2007, Blood, 109:3225-3234).

Reversible Inhibition of NMM-II Increases Functional Platelet Numbers.

Transplantation of uncultured human cord-blood $CD34^+$ cells in immuno-deficient nonobese diabetic (NOD)/SCID mice has been shown previously to yield sustained generation of human platelets (Salles et al., 2009, Blood, 114:5044-5051), but the intravenous delivery route used to date requires a large number of cells for homing and engraftment.

Figure 6:
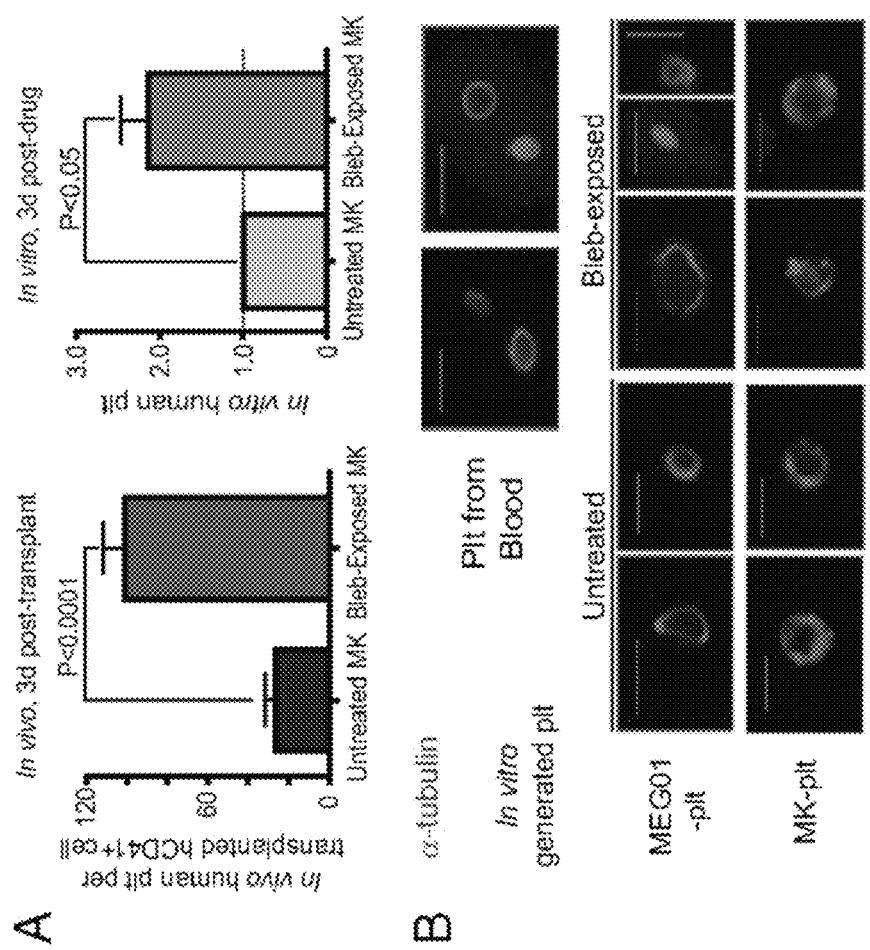
FIG. 6, comprising
Figure 6:
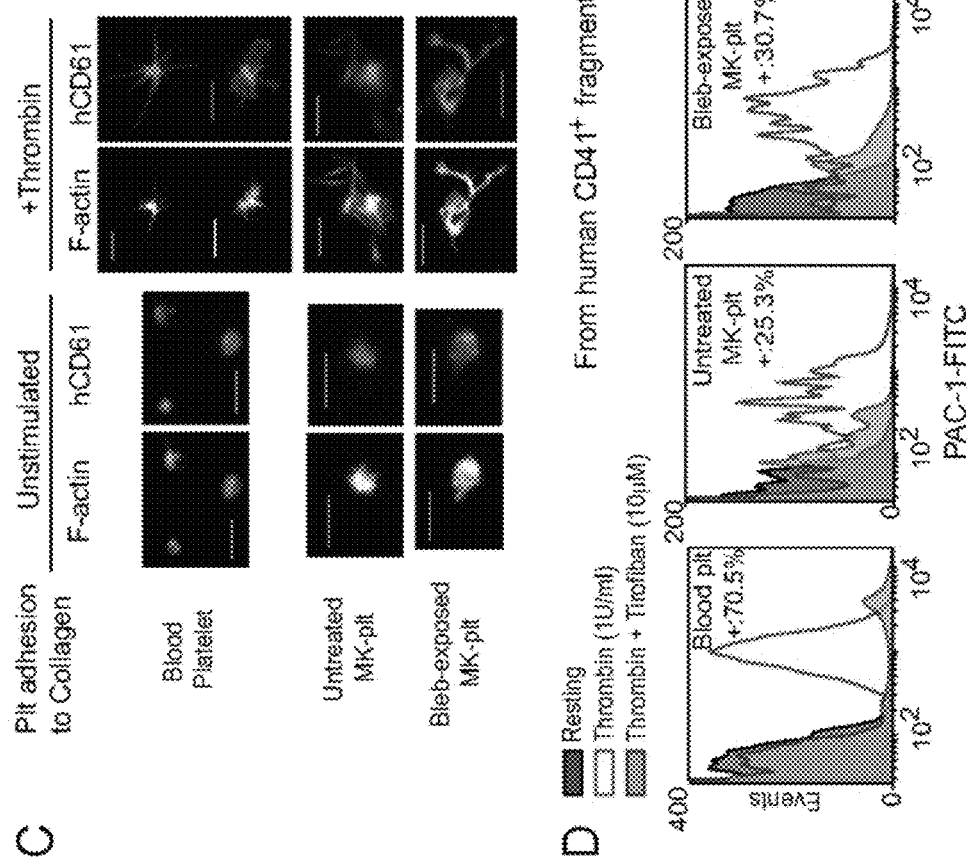
Figure 14:
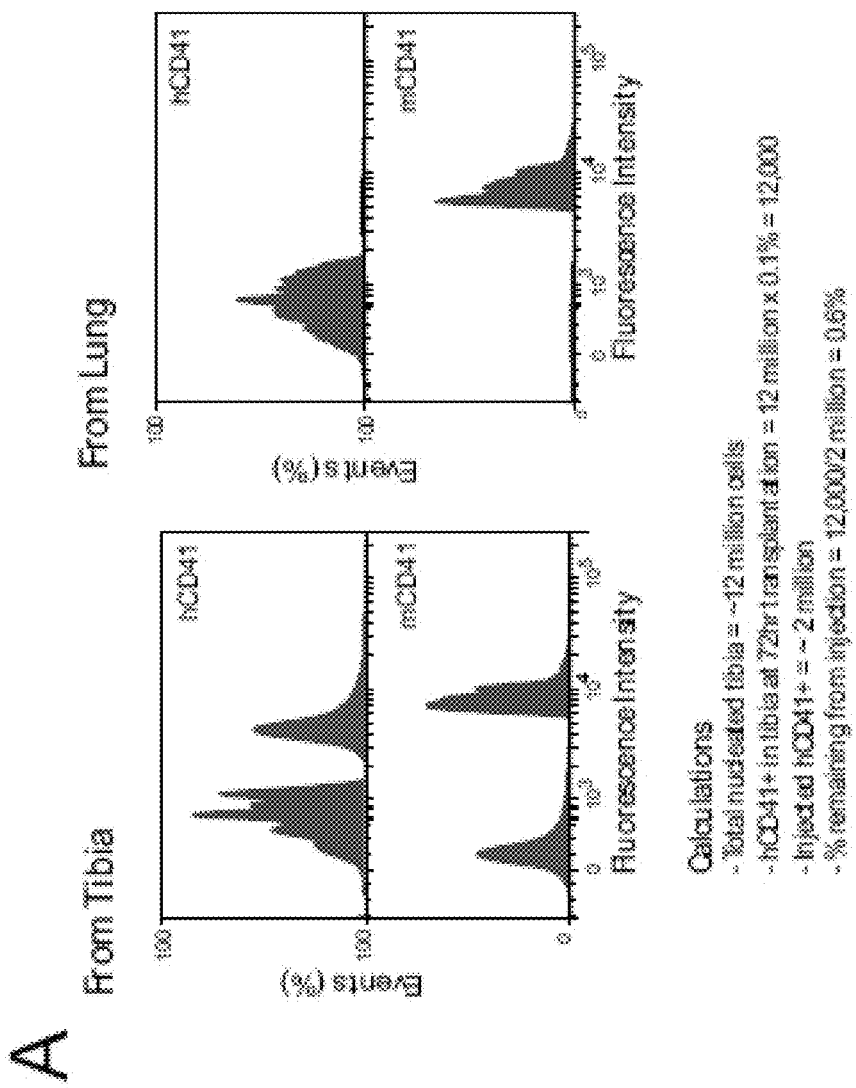
FIG. 14, comprising
Figure 14:
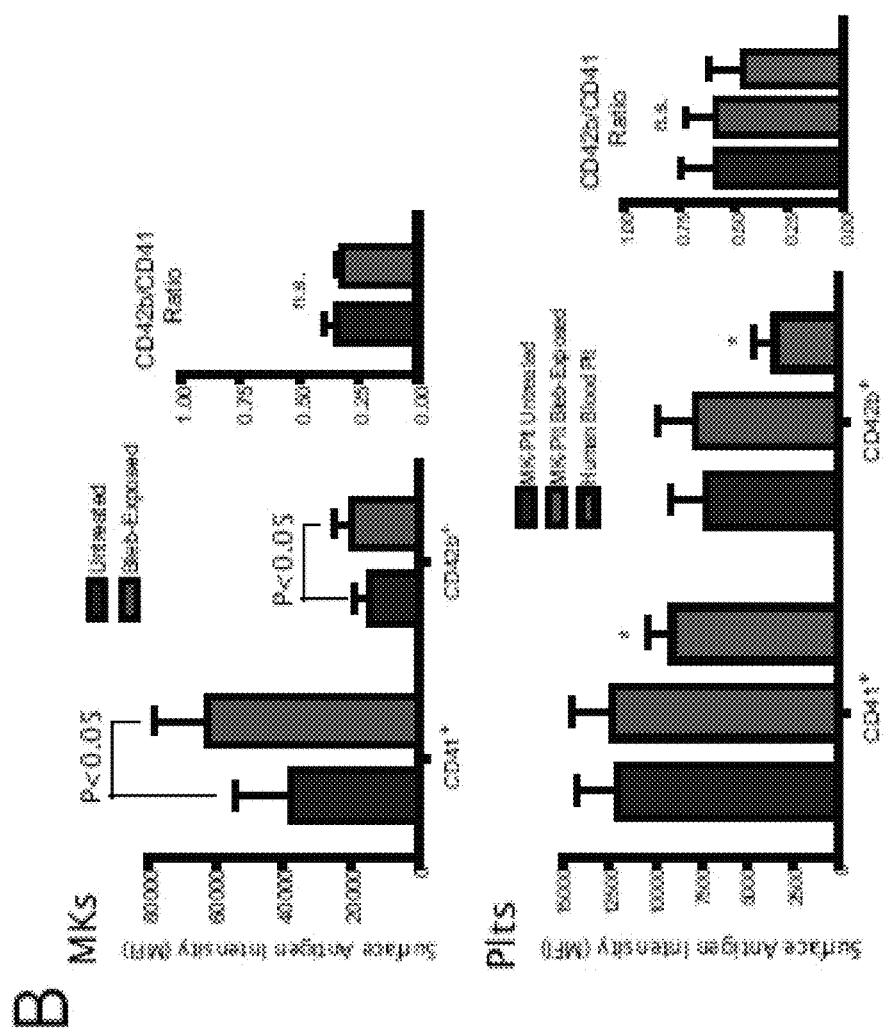
Figure 14:
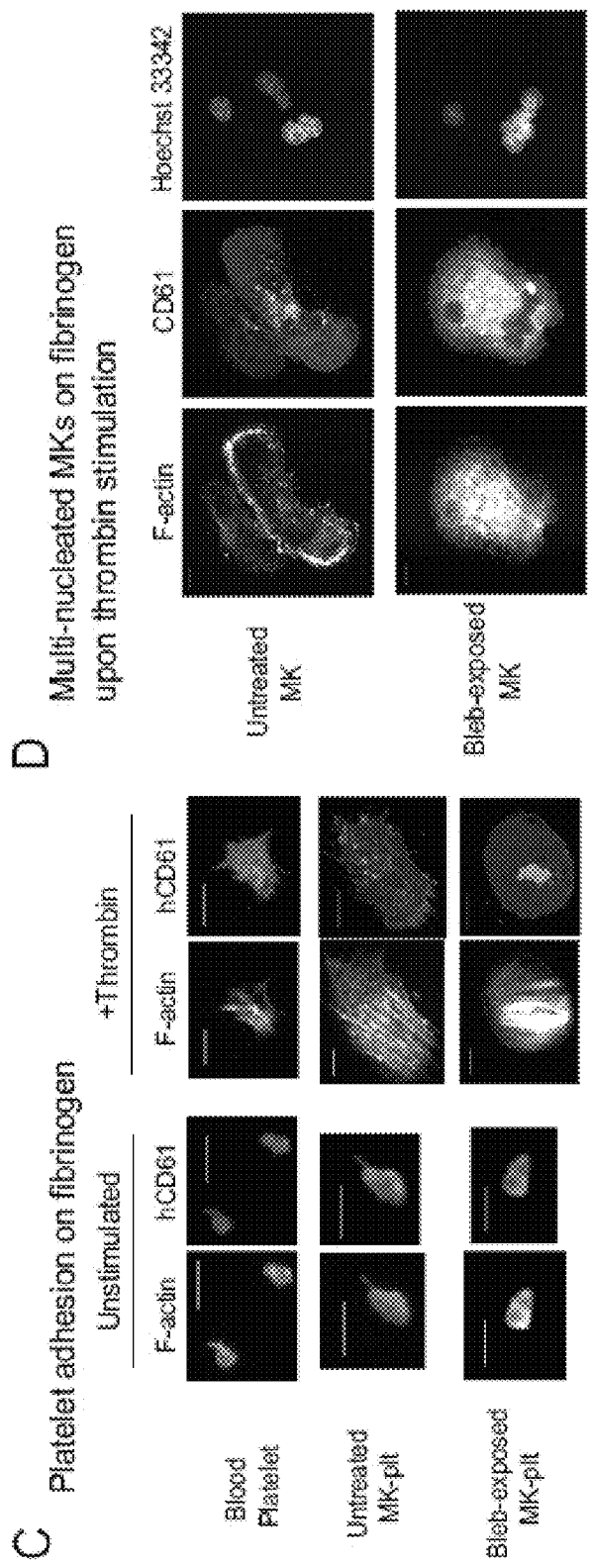
Figure 14:
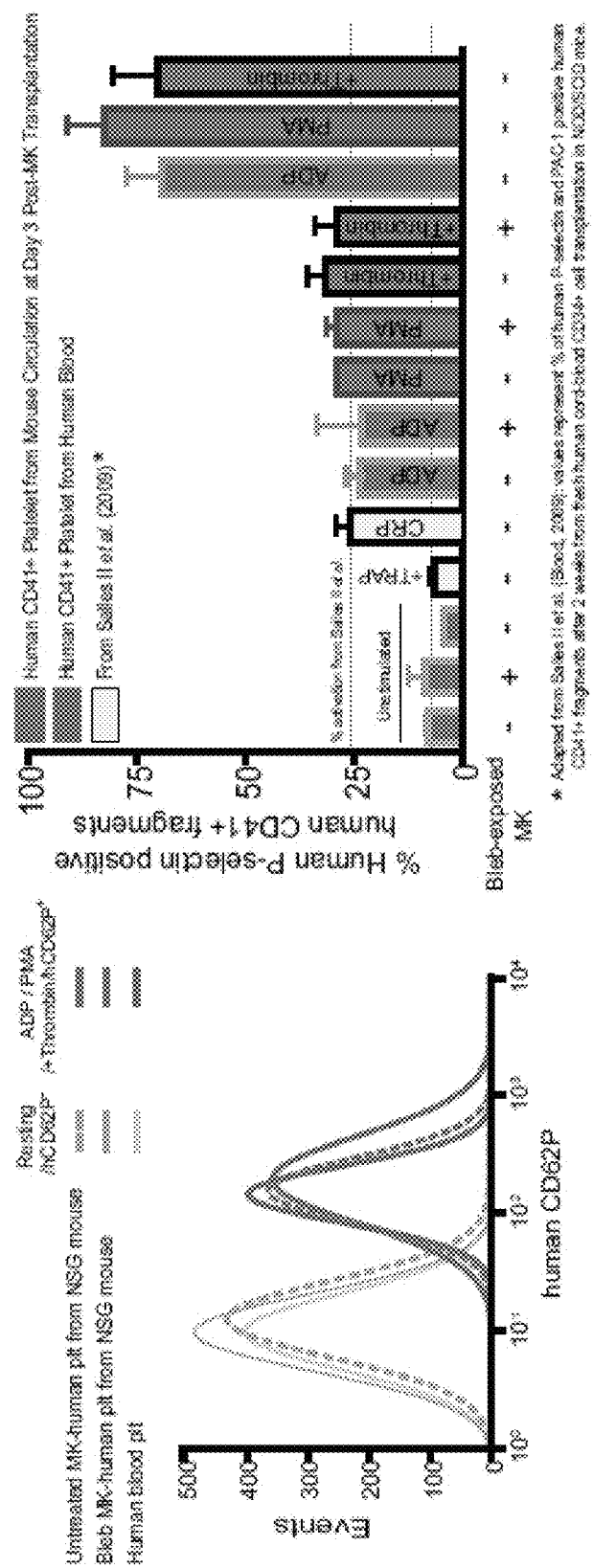

Intrabone marrow transplantation was instead used here to more rapidly expose injected cells to the marrow microenvironment per FIG. 1A. Nucleated cellular fractions of CD34+ cells cultured with SCF and Tpo with or without blebbistatin were xenografted into NOD/SCID/IL-2Rγ−/− (NSG) mice. Human MK were indeed detectable within the tibia, but not lung or spleen, at day 3 posttransplant (FIG. 14A). Subsequent quantification of circulating human-CD41+ platelets at day 3 indicates that human cells treated ex vivo with blebbistatin generate more in vivo human platelets per transplanted CD41+ cell by about fourfold (FIG. 6A, Left). These in vivo-generated platelets derive from CD41+ cells because CD34+ cells do not generate platelets until after 2 wk (Salles et al., 2009, Blood, 114: 5044-5051). To determine if the in vivo observations could be recapitulated in vitro, MKs exposed to blebbistatin for 3 d were washed and the nucleated cell fraction was isolated by a density gradient to remove any existing fragments (Fuentes et al., 2010, J Clin Invest, 120:3917-3922), followed by further culture with Tpo for 3 d. Counting the in vitro-generated, platelet-sized fragments indicates that blebbistatin-exposed MKs generate 2.5-fold more in vitro platelets per CD41+ cell than untreated MKs (FIG. 6A, Right).

Human platelet-like fragments derived from both untreated and blebbistatin-exposed MKs show cortical, coil-like MT structures as seen in some human blood-derived platelets (FIG. 6B). Furthermore, unlike platelets derived from patients with May-Hegglin anomaly (Di Pumpo et al., 2002, Haematologica, 87:943-947), platelets derived from blebbistatin-exposed MKs as well as MKs themselves do not exhibit reduced CD42b expression compared with untreated controls and blood platelets; the CD42b to CD41 mean fluorescent intensity ratio remains similar (FIG. 14B). In vitro-generated platelets are not subjected to fluid shear and are expected to be larger, as seen in imaging (FIGS. 6C and 14C), with higher CD41 and 42b intensities (FIG. 14B) and higher forward scatter compared with blood platelets. Reversible but sustained NMM-II inhibition thus does not compromise MK and platelet structure or surface marker expression (FIGS. 5 and 13D).

Regardless of blebbistatin treatment, MK-derived platelets are capable of forming filopodia on collagen-I matrix upon thrombin stimulation (at 1 U/mL) (FIG. 6C). F-actin also reorganizes through αIIbβ3 integrin outside-in signaling, as revealed by formation of filopodia, lamellipodia, and stress fibers on fibrinogen upon thrombin stimulation (at 1 U/mL) (FIG. 14C). MKs themselves spread and form stress fibers on fibrinogen regardless of blebbistatin treatment (FIG. 14D), as reported for murine ESC-derived MKs (Eto et al., 2002, Proc Natl Acad Sci USA, 99:12819-12824). Furthermore, the active conformation and clustering of human αIIbβ3, which binds fibrinogen, was directly confirmed with PAC-1 antibody binding upon stimulation of platelet-like fragments derived from both untreated and blebbistatin-treated MKs (FIG. 6D). Specificity of agonist-induced PAC-1 binding was verified by inhibiting αIIbβ3 activation with tirofiban (10 μM) (Takayama et al., 2008, Blood, 111:5298-5306). Blebbistatin-exposed MK-derived in vitro platelets thus preserve major functional responses of blood-derived platelets. Additionally, human platelets obtained from NSG mouse transplants of MKs (FIG. 6A, Left) show activation by known agonists (ADP, PMA, and thrombin) of P-selectin expression (FIG. 14E). Levels are similar to those reported for human platelets generated in NOD/SCID mice 2 wk after transplantation of CD34+ cells (Salles et al., 2009, Blood, 114:5044-5051). The results thus indicate that transient ex vivo inhibition of NMM-II by the protocol here increases the number of functional human platelets.

Promotion of Platelet Formation.

Figure 2:
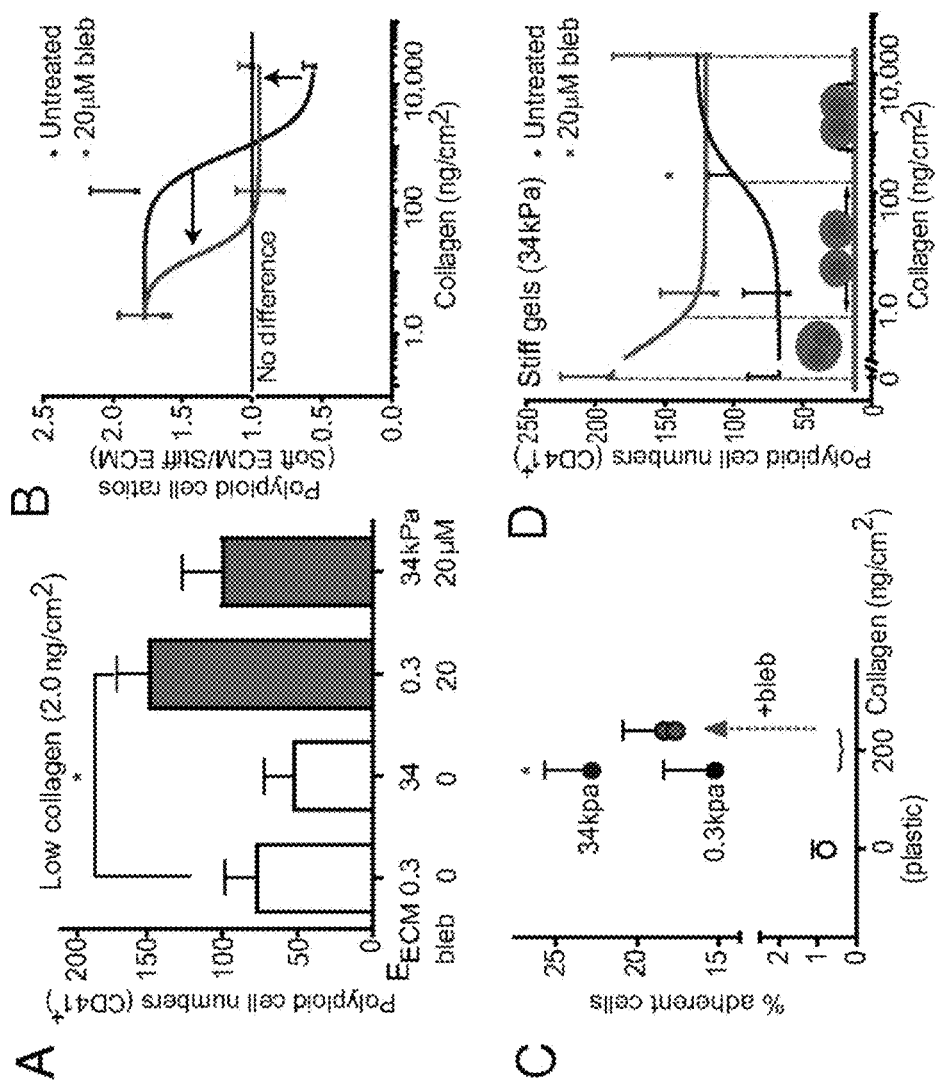
FIG. 2, comprising
Figure 2:
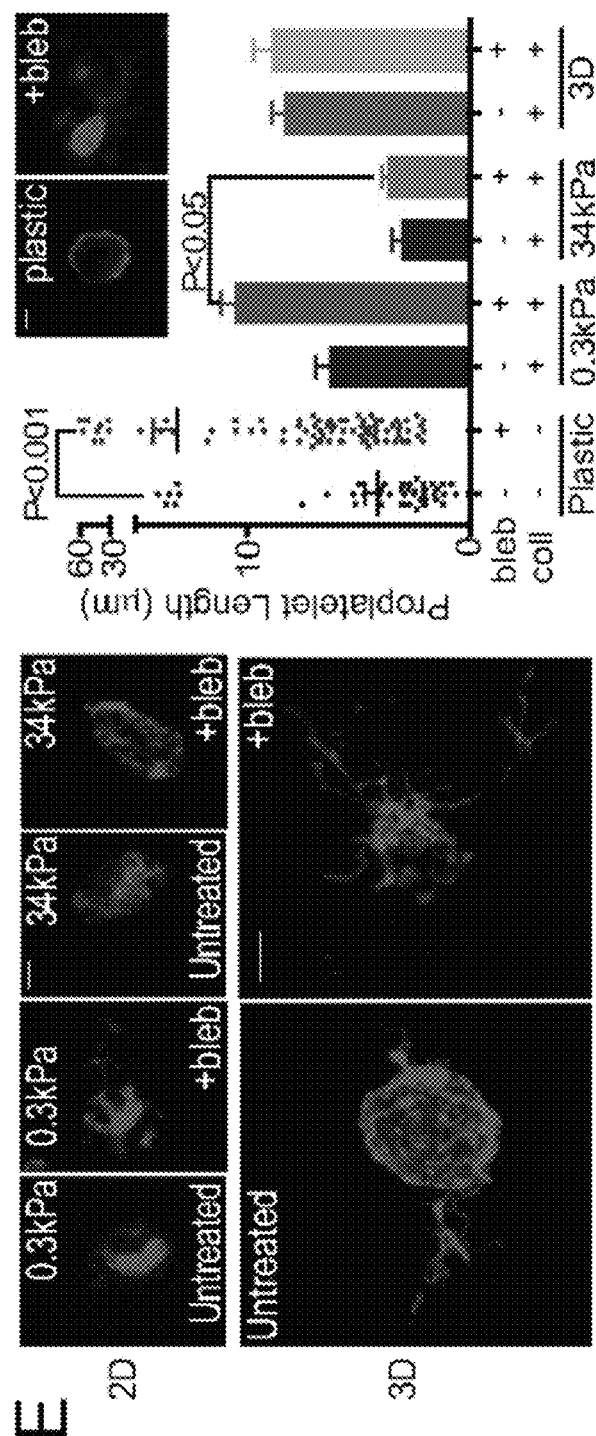
Figure 7:
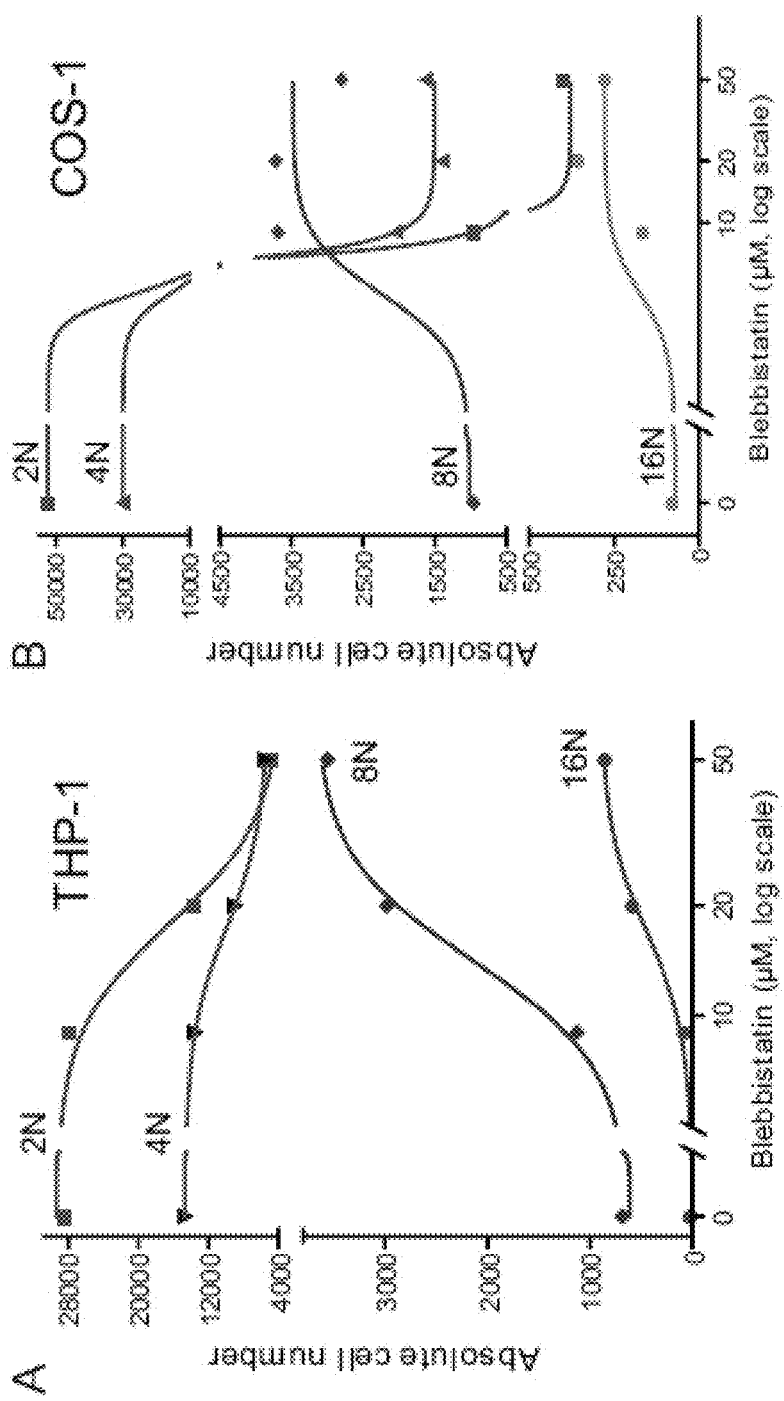
FIG. 7, comprising
Figure 7:
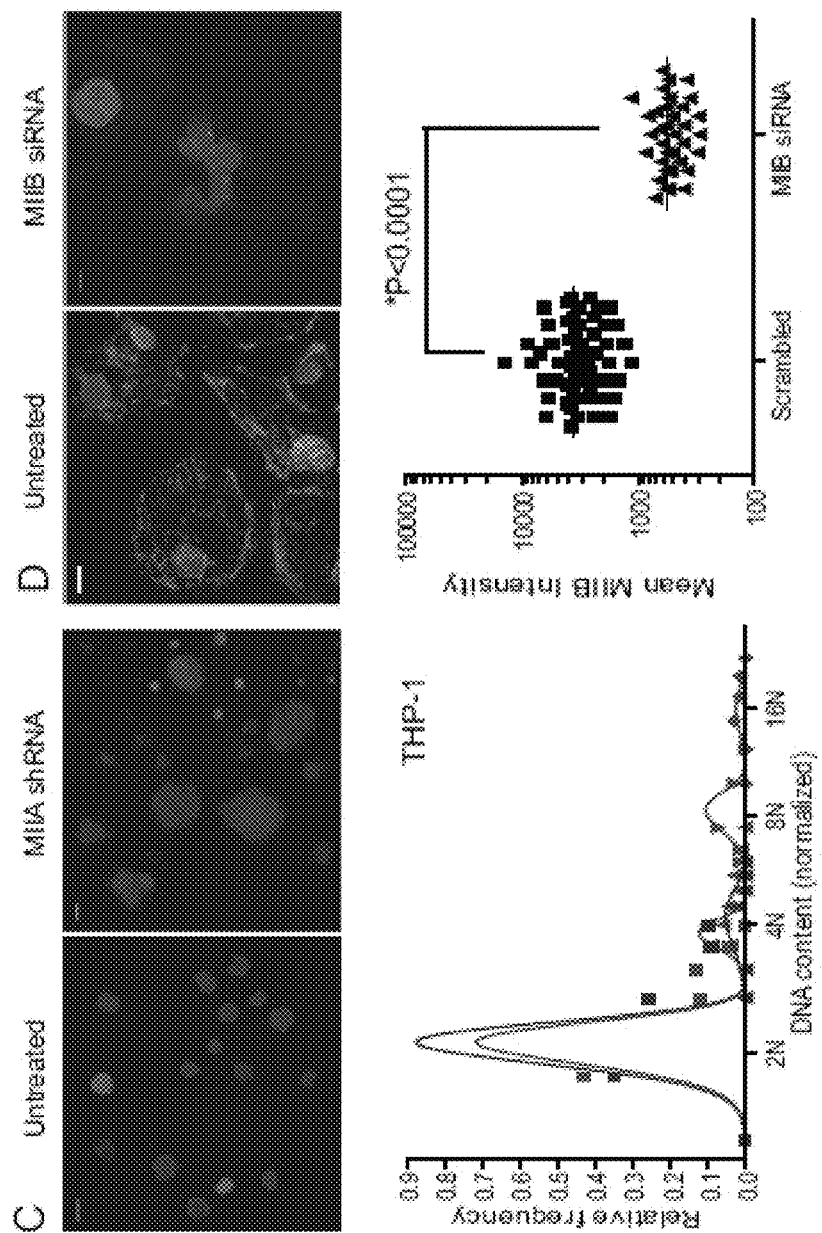

Deletion of the one myosin-II gene in *Dictyosteum* causes multinucleation of cells in suspension, but division proceeds with cells on glass coverslips via traction-mediated motility (Zang et al., 1997, Mol Biol Cell, 8:2617-2629). This finding is critical to understand more thoroughly because adhesive attachment in tissues, such as BM, is unavoidable (FIG. 1A). As described herein, inhibition of NMM-IIA over several cell cycles invariably enhances polyploidization of primary human-MKs (FIG. 1C), G-CSF-induced CD34 cells (FIGS. 10B and 10C), COS-1s, and THP-1s (FIG. 7). The effect on MKs is maximized when grown on marrow-mimetic soft matrices with low collagen density (FIG. 2). Stiff or rigid, ligand-coated matrices are well known to strengthen adhesion by mechanisms that at least involve myosin-II-dependent growth of focal adhesions (Engler et al., 2006, Cell, 126:677-689). Soft matrices here nonetheless show adherent cell numbers are still ~2,000% above nonspecific attachment to plastic, but adherent cell numbers on stiff matrices are only about 50% higher (FIG. 2C), with blebbistatin suppressing the difference. Anchorage to stiff matrix is thus not only detectably stronger but stiff, collagen$^{hi}$ matrix even promotes polyploidy (~twofold) relative to MK on plastic (FIG. 2D), presumably through anchorage-limited motility. Blebbistatin is nonetheless more potent to cells on soft collagen$^{lo}$ matrix, which minimizes adhesion-facilitated motility, and thereby maximizes polyploidy.

Previous reports demonstrated that mouse ESC-derived MKs treated with blebbistatin (Chen et al., 2007, Blood, 110:171-179) did not show higher polyploidy, probably because treatment duration was too brief relative to cell cycle (FIG. 3A). In addition, drug doses of ~100 μM are 20-fold above the $K_i$ (FIG. 1C) and in a range that are found to be toxic, indicative of off-target effects. Lineage-specific NMM-IIA knockout mouse models also did not show increased polyploidy in previous studies (Eckly et al., 2009, Blood, 113:3182-3189), probably because the knockout is irreversibly sustained; the 3-day treatment used herein is long relative to cell cycle but not so long that off-target effects accumulate and undermine cell viability. A physiological pathway of myosin-II deactivation (FIG. 4) conceivably involves transient signaling from lineage specific upstream factors, which remain to be identified. Y277 on the myosin-II head involves SHP-1/2 phosphatase (Baba et al., 2003, Biochem Biophys Res Commun, 304:67-72), and S1943 in the tail is downstream of growth factors (perhaps PDGF). The drug approach here mimics such niche signaling to maintain cell viability and even enhance myosin protein levels in MKs (FIG. 5).

Figure 8:
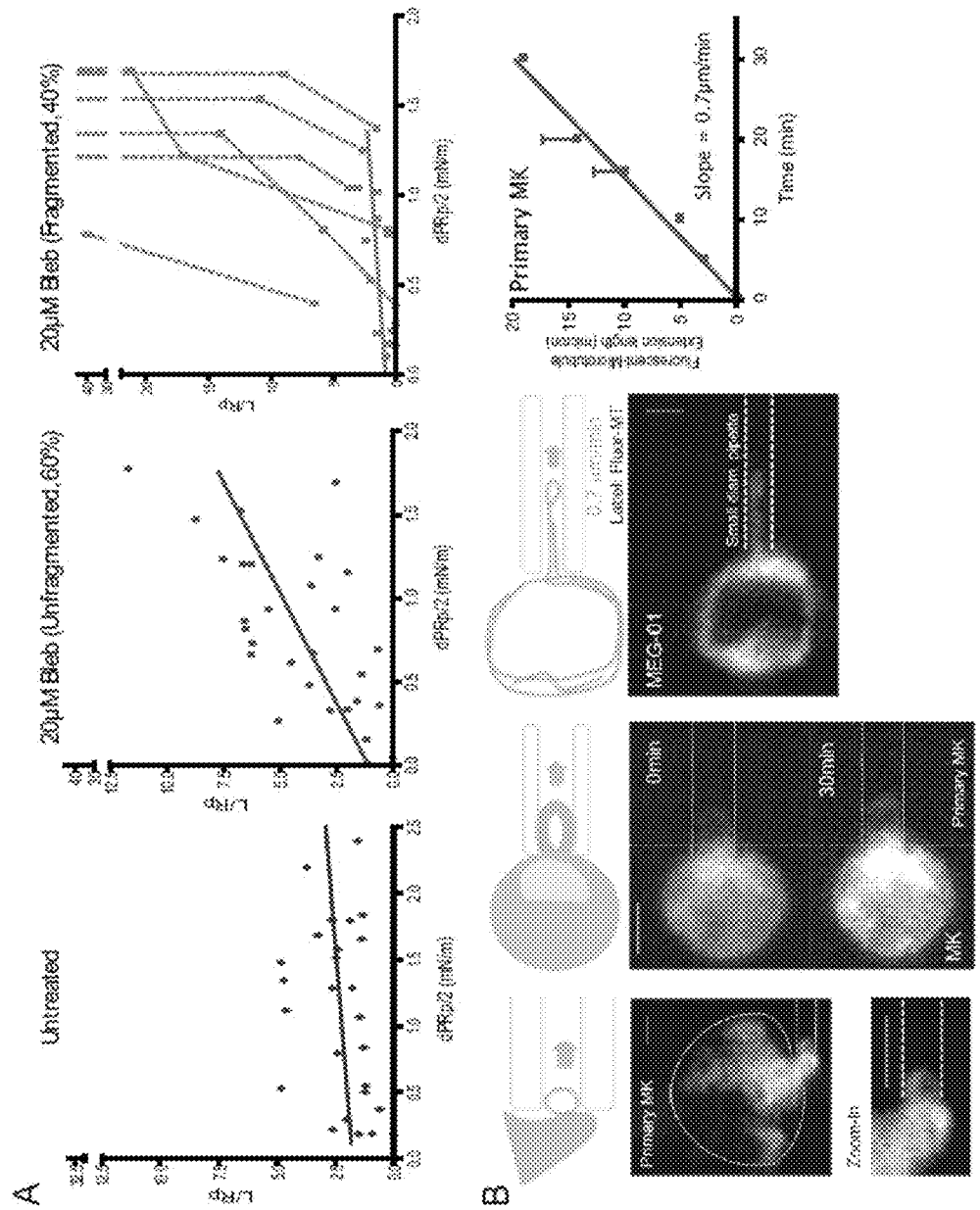
FIG. 8, comprising

The activity of NMM-II typically contributes a cortical tension that stiffens and stabilizes the plasma membrane (Engler et al., 2006, Cell, 126:677-689), and so inhibition of NMM-II understandably causes at least some adherent cell types to generate more filipodia-like extensions (Straight et al., 2003, Science, 299:1743-1747), as seen here also with COS-1 cells (FIG. 9A-9D). In addition, with strongly adherent cells, NMM-II is activated into stress fibers on rigid matrices (Engler et al., 2006, Cell, 126:677-689), and so a soft, collagen$^{lo}$ matrix would seem optimal to minimize adhesive activation of NMM-II. For these reasons, blebbistatin-treated MKs on the marrow-mimetic soft, collagen$^{lo}$ matrix are optimal for proplatelet extensions (FIG. 2E). Micropipette aspiration indeed demonstrates that myosin inhibition allows fluid forces to extend and fragment cell membranes (FIG. 1D), while aspiration also bends and distends microtubule loops (FIG. 8). This finding is fully consistent with the emerging picture (FIG. 1A) that proplatelet extensions into blood flow permit shear fragmentation to generate circulating platelets (Junt et al., 2007, Science, 317:1767-1770). A similar magnitude of softening with myosin inhibition was also documented with mesenchymal stem cells (Engler et al., 2006, Cell, 126:677-689) as well as in natural MK maturation (Smith et al., 1989, Blood, 73:1570-1575).

MK maturation involves changes in the proteome (FIG. 5) that fit a remodeled, platelet-generating phenotype. Adhesion proteins up-regulated in CD41$^+$ cells, with or without blebbistatin, include talin and vinculin, indicative of an adherent phenotype. Blebbistatin-treated CD41$^+$ cells up-regulate NMM-IIA, myosin light chains, and also actin and tropomyosin which seems consistent with previous results showing myosin inhibition reduces actin turnover and leads to F-actin stabilization (Wilson et al., 2010, Nature, 465: 373-377), contributing to membrane extensions. Microtubules also show a tendency to polymerize into such extensions, as seen in proplatelets (FIGS. 8B and 3D) (Thon et al., 2010, J Cell Biol, 191:861-874), and CD41$^+$ cells are indeed seen here to up-regulate α- and β-tubulin heterodimers.

MKs exposed to blebbistatin for several days generate platelets with a morphology and functionality similar to those from untreated MKs and approximating blood platelets. Increased functional platelet number is therefore a result of NMM-II inhibition of MKs. The NMM-II inhibition here is reversible after drug washout (Straight et al., 2003, Science, 299:1743-1747) and, given the abundance of NMM-II in platelets (Maupin et al., 1994, J Cell Sci, 107:3077-3090), it seems more likely that the irreversible deficiencies or mutations of NMM-II in May-Hegglin anomaly will undermine platelet function, as observed clinically with macrothrombocytopenia and reduced surface platelet proteins, such as CD42b (Di Pumpo et al., 2002, Haematologica, 87:943-947). Results here thus implicate regulated NMM-II coupled to a soft marrow-mimetic matrix in the polyploidization of MKs and in membrane softening with proplatelet extensions, ultimately amplifying platelet numbers in vivo.

Example 2: Role of Myosin-II in Early Hematopoietic Stem Cell and Progenitor Differentiation Activation of HSCs and progenitors in a bone marrow niche involves cytokinesis and motility processes that normally require cytoskeletal contractility. Here, enrichment of long-term human HSCs by up to 20-fold from a mixed culture of CD34$^+$ human bone marrow cells is achieved by inhibiting NMM-II which blocks cytokinesis of rapidly proliferating progenitors. HSC pathways are largely preserved in culture as elaborated by high-accuracy titration microarray analyses of ~1000 recognized hematopoietic genes that also reveal transient expression of NMM-IIB, an isoform previously not described in HSCs. NMM-IIB has been implicated in firm attachment, consistent with anchorage in a niche, whereas constitutive NMM-IIA is regulated in HSCs not at the level of expression, but by tail phosphorylation that deactivates this isoform. Functional analyses demonstrate key roles of NMM-II in cortical rigidity and mechanosensing, which is evident with HSC and MPP numbers increasing on soft matrix at high ligand. Long-term human HSCs from reversibly-inhibited cultures prove as functional in the marrows of xenografted mice as freshly derived HSCs, but expression profiles are sufficiently distinct—especially when compared with progenitors which fail to engraft—that a small subset of genes emerge as critically 'up' for engraftment, including NMM-IIB. Furthermore, while myosin inhibition generally suppresses progenitors, megakaryocytes increase in multinucleation, with xenografts showing 4-fold more circulating plts in vivo within the first week. Multifunctional myosin-II thus contributes to division and mechanosensing in hematopoiesis, and inhibition of myosin-II enriches for engraftable HSCs without the need for labeling antibodies that can block receptor function.

Figure 15:
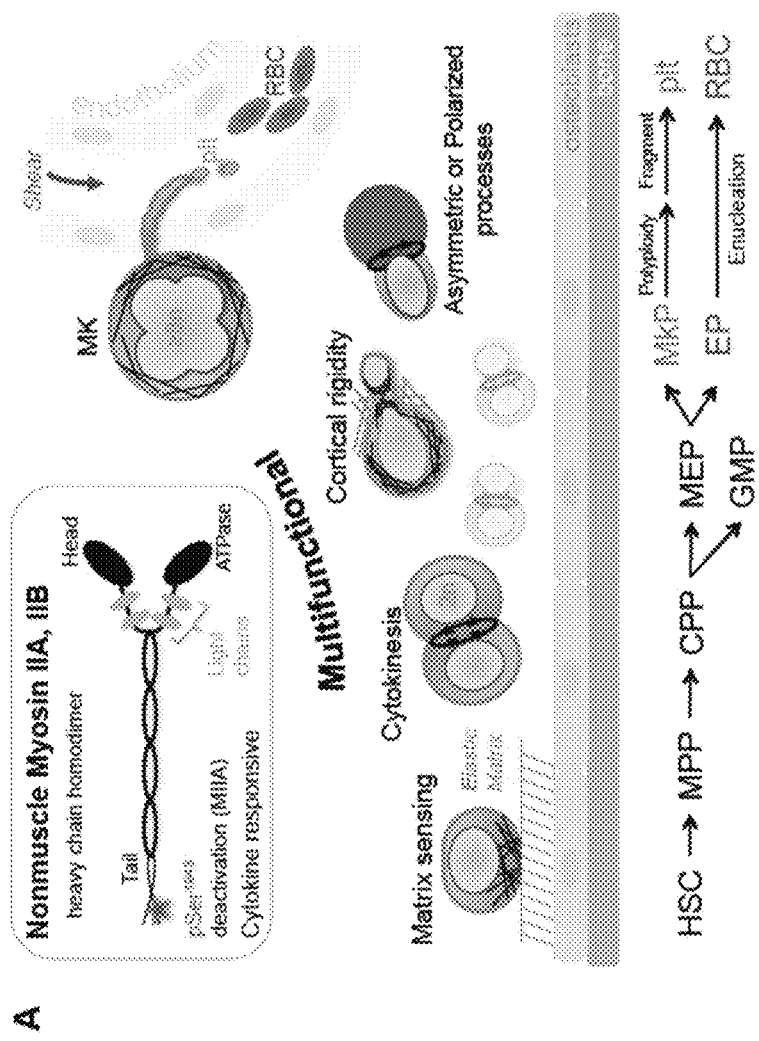
FIG. 15, comprising
Figure 15:
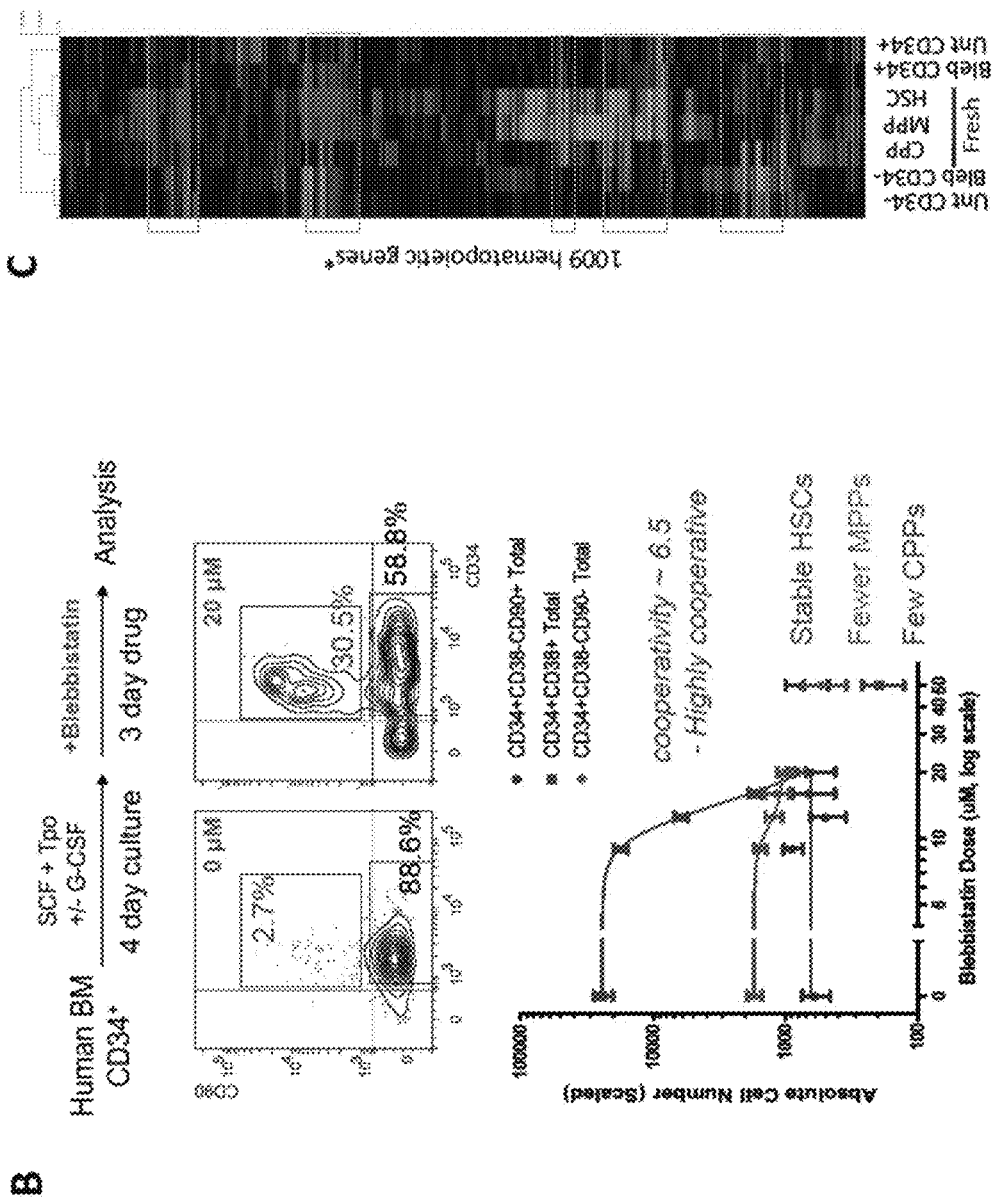

Actomyosin forces play a number of key biophysical roles (FIG. 15A). Cytokinesis is driven by myosin-II with inhibition of NMM-II often leading to multinucleated cells (Canman et al., 2003, Science, 322: 1543-1546) and symmetry/asymmetry of stem cell division in *C. Elegans* established by myosin-II (Ou et al., 2010, Science, 330(6004): 677-680). Second, NMM-II regulates adhesion when cells attach to ligand and probe matrix elasticity, promoting differentiation of MSCs (Engler et al., 2006, Cell, 126(4): 677-689) and HSC/P expansion (Holst et al., 2010, Nat Biotechnol, 28(10): 1123-1128). In addition, actomyosin forces establish an active cortical tension or rigidity that stabilizes the plasma membrane, with deletion or mutation of NMM-II increasing cell membrane flexibility (Merkel et al., 2000, Biophys J, 79(2): 707-719) and changing in MSC differentiation (Engler et al., 2006, Cell, 126(4): 677-689; Titushkin and Cho, 2007, Biophys J, 93(10): 3693-3702). All of these basic functions of myosin are also partially coupled. Cell cortex rigidity couples to cytokinesis in general (Surcel et al., 2010, Semin Cell Dev Biol, 21(9): 866-873), while in hematopoietic cells NMM-II has been implicated in erythroblast enucleation (Koury et al., 1989, J Cell Biol, 109(6 pt 1): 3005-313), T-cell motility (Jacobelli et al., 2010, Nature Immunology, 11(10): 953-961), B-cell antigen presentation (Vascotto et al., 2007, Cell Biol, 176(7):1007-1019), macrophage phagocytosis (Tsai and Discher, 2008, J Cell Biol, 180(5): 989-1003), and MK differentiation (Shin et al., 2011, PNAS, 108(28): 11458-11463) among other processes. However, very little is known about the role(s) of actomyosin forces in HSC/Ps during adult hematopoiesis.

It is described elsewhere herein that sustained pharmacological inhibition of NMM-II together with soft 2D matrices similar to perivascular niches in marrow—rather than rigid like bone or rigid like plastic—maximize both MK maturation and plt generation. HSCs are similar to mature MKs at least in that dormant cells remain undivided in vivo whereas progenitors of other lineages and maturing cells rapidly expand in number. Molecular similarities between HSCs and MKs were also highlighted recently (Huang and Cantor, 2009, J Cell Biochem, 107(5): 857-864). To understand how mechanical forces regulate adult hematopoiesis, it was sought to determine the role of NMM-II in HSC proliferation and differentiation by starting with human BM-derived CD34$^+$ cells culture with just 2~3 standard cytokines followed by sustained but reversible inhibition of NMM-II for 3 days.

The materials and methods employed in these experiments are now described.

Cell Culture

Freshly purified bone marrow-derived human CD34$^+$ cells were obtained from either the Penn Xenograft Core Facility or AllCells (Emeryville, Calif.). Cells from at least 20 different donors were used in this study. Purity of the samples (>98%) was confirmed by flow cytometry with monoclonal antibody against human CD34. All experiments were performed in HSC expansion media (StemLine, Sigma) supplemented with 1× antibiotics, 20% BIT 9500 Serum Substitute (StemCell Technologies), 2 mM Lglutamate (Gibco) and the following human recombinant cytokines: SCF (100 ng/ml) and Tpo (100 ng/ml). In some occasions, the media was also supplemented by G-CSF (100 ng/ml), epidermal growth factor (EGF, 100 ng/ml), transforming growth factor beta 1 (TGF-beta1, 100 ng/ml), erythropoietin (EPO, 1 U/ml) and interleukin-3 (IL-3, 10 ng/ml). All cytokines were purchased from R&D Systems. After cells were cultured for 4 days, they were treated with different doses of cellular contractility inhibitors, including (±)-Blebbistatin (Bleb) (EMD Biosciences) and/or CH-223191 (Sigma) for indicated durations of up to 3 days. Cells were cultured at 37° C. in 5% $CO_2$.

Antibody Staining and Flow Cytometry

Surface marker analysis for HSC/Ps was done on either a LSR II flow cytometer or FACSCalibur (Becton Dickinson). Fresh or cultured $CD34^+$-derived cells were stained in staining media (2% FBS in PBS) at room temperature for 1 hr with PE or APCCy7 anti-CD34 (581, Invitrogen or Biolegend), PECy7 anti-CD38 (HIT2, eBioscience), PECy5.5 anti-CD45RA (MEM-56, Invitrogen), APC anti-CD90 (5E10, BD Bioscience), washed and stained with Hoechst 33342 (Invitrogen) at 37° C. for 30 min to stain nuclei, followed by washing with staining media with 7-AAD (Sigma) to exclude dead cells. Cells isolated from the bone marrow stained for 1 hr with APC anti-mouse CD47 (miap301, AbD Serotec), FITC anti-human CD47 (BD Biosciences), and PE anti-human CD11b, PE anti-human CD19 (both from BD Biosciences), or PE anti-human Glycophorin A (Invitrogen). Plts and RBCs were analyzed by staining with PE anti-mouse CD41 (eBioscience) and FITC anti-human CD41 (eBioscience) for 20 min, followed by analysis on FACSCalibur on log forward and side scatter scales.

Intracellular Flow Cytometry

Cells were fixed with 4% paraformaldehyde in PBS for 10 min, washed with PBS and resuspended in 0.1% saponin in HBSS (staining medium). The samples were then stained with antibodies against cytoplasmic antigens, including NMM-IIA (Sigma), NMM-IIB, phospho-NMM-IIA and caspase-3 (all from Cell Signaling Technology) for 30 min at room temperature. In some cases, cells were concurrently stained with PE anti-CD34 or anti-human CD38 for subpopulation analysis. Cells were then washed and stained with anti-rabbit or mouse secondary antibodies conjugated with Alexa 647 (Invitrogen) for 30 min, followed by analysis on FACSCalibur.

Carboxyfluorescein Diacetate Succinimidyl Ester (CFSE) Labeling $CD34^+$-derived cells were labeled with CFSE (2.5 μM) in PBS/5% FBS for 3 min in dark at room temperature and washed once with PBS/5% FBS and once with HSC expansion media. The labeled cells were analyzed every day for 3 days using multi-color flow cytometry with HSC/P markers. Given that cell division is unsynchronized, cell numbers from different CFSE peaks are normalized by dividing the cell numbers by $2^{division\ number}$ to correct for the effect of cell expansion. The mean division number from each sample was calculated by fitting normalized CFSE data to the normal distribution curve and taking its mean value.

DNA Microarray Transcriptional Profiling

Total RNA was extracted from cells using trizol and isolated by RNeasy (Qiagen) according to manufacturer's protocol. Total RNA was amplified and converted to cDNA using WT-Ovation Pico kit (NuGen) and converted to ST-cDNA, fragmented and biotinfunctionalized using WT-Ovation Exon Mudule (NuGen). Hybridization cocktails were prepared at 45.4, 15.1 and 7.6 ng/μl ST-cDNA and mixed with Eukaryotic Hybridization Controls (GeneChip) at proportional concentrations. Each sample was interrogated by sequential hybridization, rinse and scan cycles on a single Human Gene 1.0 ST DNA microarray (Affymetrix), from low to high concentration, and followed by two rinse-scan cycles in which no sample was added. In each experiment the scanned intensities that were obtained from all samples, five scans per array, were mutually RMA-summarized to transcription clusters gene levels. Log-base-2 fold changes were calculated for each scan separately relative to the mean Bleb-treated and non-treated $CD34^+$ and $CD34^-$ intensities, gene by gene, and the average and standard deviation values (SD) were calculated across scans. Heat maps of selected genes summarize data from technical and biological replica. Average gene-expression fold changes±STD of HSC, MPP and CPP samples are shown in white. Log-base-2 fold changes of Bleb-treated and non-treated $CD34^+$ and $CD34^-$ were averaged from two biologically independent experiments and are shown±SD. The particular fold-changes are color coded on a logarithmic scale that is defined per each heat map. Color-coded gene symbols represent the absolute gene expression levels of the biologically-replicated averages of $CD34^+$ non-treated intensities. Gene expression levels are coded $<=5$ (green) to $>=10$ (red) on a log-base-2 scale. Samples and genes were clustered by Pearson Correlation (MeV). Dendograms represent the correlative proximity of log-base-2 gene expression fold changes. Mean gene expression levels were calculated by averaging across five array scans. Log-base-2 gene expression fold changes were calculated relative to the mean Bleb-treated and non-treated $CD34^+$ and $CD34^-$ intensities, gene by gene.

Cell Culture and Transfection in COS-1 Cells

COS-1 cells were obtained from ATCC (Manassas, Va.) and were maintained in high glucose DMEM with 10% FBS. Lipofectamene 2000 was used for both siRNA knockdown of NMM-IIB and overexpression of NMM-IIA constructs, according to the manufacturer's instruction (Invitrogen), when cells were 5-10% and 60-70% confluent, respectively. Efficiency of NMM-IIB siRNA was confirmed to be >90% as indicated by quantitative immunofluorescence analysis (FIG. 2.S1D). For GFP-tagged NMM-IIA constructs, the transfection efficiency was about 30~40%. Cells were then subjected to micropipette aspiration or replated on FN-coated gels to study cell spreading.

Micropipette Aspiration and Cell Culture Under Continuous Shear

Fresh BM $CD34^+$ cells or transfected COS-1 cells in suspension were subjected to micropipette analysis. Capillary tubes of 1.0 mm inner diameter (World Precision Instruments, Sarasota, Fla.) were pulled into micropipettes using a Flaming-Brown Micropipette Puller (Sutter Instrument, Novato, Calif.) and cut further using a deFonbrune-type microforge (Vibratome, St. Louis, Mo.). The average micropipette diameter was around 3 μm. Micropipettes were attached to a dual-stage water manometer with reservoirs of adjustable height. Suction was applied by a syringe, and the corresponding pressure was measured by pressure transducer (Validyne, Northridge, Calif.) calibrated by a mercury U-tube manometer. Pressures for different experiments ranged from 0.5 to 15 kPa. For cell culture under continuous shear, $CD34^+$-derived cells were cultured at 37° C. for 2 days in an incubator shaker at 200 rpm.

Construction of Fn-Coated Gels with Different Matrix Elasticity 15-18 mm glass coverslips were treated in order with ethanol, RCA solution (1:1:3 for 15N NH4OH:30% H2O2: dH2O), methylene chloride and 0.1% allyltrichlorosilane solution. To control gel's stiffness, n,n' methylene-bis-acrylamide and the acrylamide solution was mixed at the ratio of 0.07%:3% for soft gels (0.3 kPa), or the ratio of 0.3%:8% for stiff gels (34 kPa), final concentrations in PBS. ~25 µl of the mixed solution was polymerized on a coverslip with 10% ammonium persulfate and n,n,n',n'-tetramethylethylenediamine. During polymerization, gels were covered with another coverslip to obtain a uniform gel surface with the final thickness of ~100 µm. Different concentrations of FN were then cross-linked with polymerized gels using sulfo-SANFAH (Pierce, Rockford, Ill.) by UV-crosslinking Thickness of gels and relative FN concentrations were verified by confocal microscopy. It is assumed that most FN from the solution was attached to gels (>70%). FN-coated gels were then treated with UV in PBS for at least 1 hr before use in cell culture.

Immunofluorescence Analysis

Cells on coverslips were fixed with 4% paraformaldehyde, followed by permeabilization with 0.5% Triton X-100 in PBS for 15 min and blocking with 1% BSA in PBS for 30 min. Samples were then stained with primary antibodies (1:100 for all antibodies used) for overnight at 4° C. After washing, staining with appropriate Alexa 488 or 647-conjugated secondary antibodies (1:400) and TRITC-phalloidin was performed for 45 min at room temperature. Cells were washed three times with PBS and mounted in ProLong Gold antifade medium (Invitrogen). Samples were then analyzed by fluorescence microscopy.

Cell Sorting

BM $CD34^+$-derived cells in culture at day 7 were stained with CD41-FITC at room temperature for 1 hr, followed by with Annexin-V-PE (BD Biosciences) in the Annexin-V staining medium for 15 min. Cells were then resuspended in 2% FBS/PBS with 7-AAD. Viable HSC/Ps and differentiated cells at day 7 culture were separated on the basis of CD34 surface expression by cell sorting performed on a FACS Vantage™ machine (Becton Dickinson). Dead cells stained with 7-Amino-actinomycin D (7-AAD) and Annexin-V were excluded from sorting. Sorted cells were directly processed for microarray analysis.

Colony Forming Assay 1000-3000 $CD34^+$-derived cells were seeded into methylcellulose containing media (MethoCult H4434, StemCell Technologies) supplemented with SCF, GM-CSF, IL-3, Epo. They were cultured for 14 days and colonies were scored at 10× magnification based on the published morphological criteria by StemCell Technoloigies. Colony forming content was normalized per 10,000 cells seeded.

Engraftment of $CD34^+$ Cells in NSG Mice and Limiting Dilution Analysis

BM-derived $CD34^+$ cells were cultured in SCF and Tpo (100 ng/ml each) for 4 days and treated under control conditions or Bleb (20 µM) for 3 days. The cells were injected intra-tibially into sub-lethally irradiated (250 rads) 6-10-week-old NSG mice within 24 hr after irradiation. Engraftment was assessed by analysis of blood or bone marrow using anti-mouse and anti-human CD47 antibodies using flow cytometry. The mice were sacrificed after sixteen weeks post-transplantation. For secondary engraftment, 50% of the bone marrow from femurs and tibias from each mouse was transplanted into one sub-lethally irradiated NSG mouse. 16 weeks after transplantation, blood and bone marrow were harvested from the mice and analyzed by flow cytometry. All animal experiments were done in accordance with institutional guidelines approved by the ethical committee from the University of Pennsylvania. The human repopulation HSC frequency was quantified by extreme limiting dilution analysis (ELDA) software (Hu and Smyth, 2009)

Rare Human Blood Cell Isolation from NSG Mice

The surface of micro-channel slide (µ-Slide VI, Ibidi) was coated with anti-human CD47 antibody via adsorption overnight at 4° C. The coated chamber was then blocked with 1% BSA/PBS for 30 min before use. Approximately 500 µl of blood cells derived from NSG mice transplanted with human cells were diluted in PBS/1% BSA and passed through the antibody-coated chamber using a syringe pump (~10 ml/hr), followed by washout with PBS/1% BSA for 10 min. Human RBCs remaining on the chamber were subjected to immunofluorescence with anti-human GPA antibody staining. The experimental samples were compared to the control sample derived from uninjected NSG mice.

Statistical Analyses

All statistical analyses were performed using GraphPad Prism 4. Unless otherwise noted, all statistical comparisons were made by unpaired 2-tailed Student t-test and were considered significant if $P<0.05$. All dose-response data were fitted to sigmoidal dose-response with variable slope with x-axis in a log scale.

The results of the experiments are now described.

Myosin-II Inhibition Enriches for HSC/Ps and Switches Isoforms in Differentiation Adult, primitive HSCs ($CD34^+CD90'CD38^-$) are enriched 16-fold (5-24 fold in range) on average by Bleb which inhibits the A, B, C isoforms of NMM-II (FIG. 15B). The HSCs proved relatively resistant to a 3-day treatment with Bleb, which will be seen below to be long relative to the cell cycle. However, the Bleb-treated MPPs ($CD34^+CD90^-CD38^-$) and CPPs ($CD34^+CD38^+$) are depleted 1.8-fold (1.3-2.3 fold) and 31-fold (15-48 fold), respectively. Responses of MPPs and CPPs proved highly cooperative in drug concentration and display a similar inhibition constant $K_i$ (~10.5 µM) that is only about 2-fold higher than results from solution inhibition of NMM-II (Kovacs et al., 2004), and likely reflects the highly cooperative nature of myosin filament function in cells. The phenotypic observations are also supported by global mRNA profiles of over 1000 genes reported previously to be specifically upregulated or downregulated in HSCs (Novershtern et al., 2011, Cell 144(2): 296-309); Bleb-treated $CD34^+$ cells proved to be closely correlated to fresh HSC and fresh MPP but not CPP (FIG. 15C). In contrast, untreated $CD34^+$ cells appear more closely correlated with fresh CPPs, indicating a high degree of differentiation in culture. The list of specific genes that show close correlation between drug-treated $CD34^+$ cells and fresh HSC/MPP is catalogued in FIG. 21 (values expressed in a $log_2$ scale). NMM-II activity is therefore required for hematopoietic expansion at least in typical serum-free cultures with minimal cytokines and minimal adhesion.

Because Bleb enriches for the primitive HSC cellular phenotype, mRNA profiles of drug-treated $CD34^+$ cells are expected to approximate those of highly purified long-term (LT) HSCs and should also reveal cytoskeletal components of the various lineages, including the myosins. A novel 'titration microarray' analysis of mRNA samples from cultured (sorted for viable $CD34^+$ and $CD34^-$ cells) and fresh cells was applied, allowing improved quantitation with microarrays by discriminating gene probes that were either saturating in intensity or closer to non-specific background. The HSC-specific surface antigens CD133 (PROM1) and CD34 are upregulated by more than 2-fold above the pooled average (of cultured cells) only for the Bleb-treated CD34+ cells in culture and for freshly isolated HSCs and MPPs (FIG. 16A). Note that CD34 protein, but not CD133, was sorted for, which is known to be a marker for primitive HSCs (Kobari et al., 2001, Journal of Hematotherapy and Stem Cell Research 10(2): 273-281). The cultured CD34− cells consist of myeloid lineages and show that PROM1 and CD34 are downregulated by about 2-fold or more. CD34+ cells that are cultured without Bleb and sorted for CD34-protein maintain elevated CD34-mRNA, but CD133 is downregulated, emphasizing that Bleb enriches for HSCs. PROM1 and CD34 have high gene intensities, but fresh cells were also sorted for CD38 and CD90 (THY1) protein which have low gene intensities: CD38-mRNA is similarly lower in HSCs and in the cultured CD34+ cells than CD34− cultured cells, consistent with a previous report (Terstappen et al., 1991, Blood, 77: 1218-1227). In addition, THY1 shows a weak, but consistent decreasing trend from a maximum for fresh HSCs and for Bleb-treated CD34+ cells, consistent again with a previous observation (Baum et al., 1992). More generally, hierarchical clustering analysis including the key markers here plus many more (FIG. 15C) showed a positive correlation between cultured and fresh HSC/Ps only with Bleb-treated CD34+ cells (Pearson correlation coefficient p=~0.8). Without Bleb, CD34+ cells in culture show no overall correlation with fresh HSC/Ps (Pearson correlation coefficient 0.0), and so myosin-II inhibition in culture clearly enriches for early HSC/Ps.

Surprisingly, whereas past reports have indicated hematopoietic expression only of NMM-IIA (Sohal et al., 2008, PLoS One, 3(8): e2965), transcript profiling indicated two myosin-II isoforms with similarly high transcript intensities: NMM-IIA (MYH9) and NMM-IIB (MYH10). Background levels of gene intensity were detected with NMM-IIC (MYH14). NMM-IIB mRNA appears at least 3-fold higher in CD34+ (HSC/P) than CD34− (differentiated) cells, and hierarchical clustering analysis shows the expression profile for MYH10 correlates stronger with CD34's profile (p=0.8) than any other gene. In comparison, NMM-IIA is slightly but reproducibly lower in the drug-treated CD34+ cells (~30%). Note that all myosin-II isoforms are inhibited by Bleb (Straight et al., 2003, Science, 299(5613): 1743-1747). The difference in NMM-IIA mRNA expression directly reflects the difference in NMM-IIA protein expression between HSC/MPP(CD34+CD38−) and CPP(CD34+CD38+), which again shows a 30% reproducible difference (FIG. 16B, Top). NMM-IIB protein expression patterns in CD34+ and CD34− cells also directly correlate with its mRNA expression (FIG. 16B, Bottom). The results thus indicate temporal-specific regulation of NMM-II isoforms with NMM-IIA upregulated during early stage HSC differentiation and NMM-IIB downregulated in late stage differentiation.

The actomyosin cytoskeleton is not particularly well-studied in early HSC/Ps compared to many other cell types, perhaps because these cells have only a thin cortical cytoskeleton between membrane and nucleus. The cytoskeleton is nonetheless expected to link to the membrane, including integrins that some have used as markers for HSC/Ps. Previous literature on freshly isolated cells has shown that alpha 2 integrins are upregulated (Benveniste et al., 2010, Cell Stem Cell, 6(1): 48-58) while alpha 4 integrins are downregulated (Papayannopoulou and Nakamoto, 1993, PNAS, 90(20): 9374-9378) during differentiation. The studies presented herein, measuring mRNA levels in HSC/Ps, are consistent in trend: alpha 2 integrins are upregulated 1.5-fold in untreated CD34+ culture compared to Bleb-treated or fresh CD34+ cells, while alpha 4 integrins are upregulated in fresh CPP, but become downregulated in cultured CD34+ cells. Recently, alpha 6 integrin was used to distinguish between functional LTHSC and MPP populations since its surface expression is ~2 fold higher in LT-HSC than MPP (Notta et al., 2011, Science, 333(6039): 218-221). Fresh HSC shows 30% higher expression in alpha 6 integrin mRNA than MPP. However, expression profiles of alpha 6 integrin across different HSC/P subpopulations from primary or cultured cells have not been characterized. In fact, alpha 6 integrin shows high mRNA levels on average across the samples and is at least 3 times lower in fresh than cultured CD34+ cells, indicating that the mRNA is upregulated in early HSC differentiation. Beta 1 integrin is known to partner with alpha 2, 4 and 6, and follows the trend for general upregulation of alpha 2 and 6.

The prominent nucleus in hematopoietic cells also has a characteristic skeleton of lamins in HSC/Ps (Pajerowski et al., 2007, PNAS, 104: 15619-15624), and consistent with HSC/Ps: LMNA expression is similarly low in Bleb-treated CD34+ compared to any other cultured cells, while LMNB1 and LMNB2 expression levels remain relatively constant in culture. In addition to imparting the nucleus with mechanical stability (Pajerowski et al., 2007, PNAS, 104: 15619-15624), the lamins have been implicated in regulation of gene expression within mesenchymal tissues (Dechat et al., 2010, Cold Spring Harb Perspect Biol, 2: a000547), and so the similarity of lamin profiles could be important to hematopoiesis. In addition, many cytoskeletal transcripts are down-regulated in the drug-treated CD34+ cells, in contrast to MKs that show considerable up-regulation of cytoskeletal proteins upon NMM-II inhibition (Shin et al., 2011, PNAS, 108(28): 11458-11463) and MK differentiation (Raslova et al., 2007, Blood, 109:3225-3234). In HSC/Ps, low levels of adhesion linkers such as vinculin (VCL), talin (TLN1), and/or filamin (FLNA) will tend to limit integrin engagement with cytoskeleton, and the cytoskeleton will also tend to be softer with low levels of actin (ACTB) and actin crosslinkers such as actinin (ACTN1; ACTN4). Among these, FLNB is interesting in that it appears upregulated in fresh HSC/Ps and only the Bleb-treated CD34+ cells, perhaps implicating this actin-crosslinker as a stem cell 'partner' to NMMIIB. It is important to note that although not further validated, a previous microarray analysis also reports upregulation of MYH10, CD34 and FLNA in HSCs compared to other hematopoietic populations (Novershtern et al., 2011, Cell 144(2): 296-309). These findings suggest that cytoskeletal gene expression is generally low in fresh CD34+ and NMM-II inhibited CD34+ cells, while they are supported by a select set of genes, including NMM-IIB.

"Frustrated Cytokinesis" of Progenitors Enhances Apoptosis

The term "frustrated cytokinesis" has been used to refer to a process in which cells progress through the early stages of mitosis and cytokinesis without significant difficulty but were delayed at later stages, with regression of the cleavage furrow leading to an increase in binucleate cells. Such a failure to complete a standard morphological program is also illustrated by "frustrated phagocytosis" in which a phagocyte adheres, activates, and spreads on an opsonized, flat substrate, but is unable to engulf the substrate due to substrate size.

Figure 17:
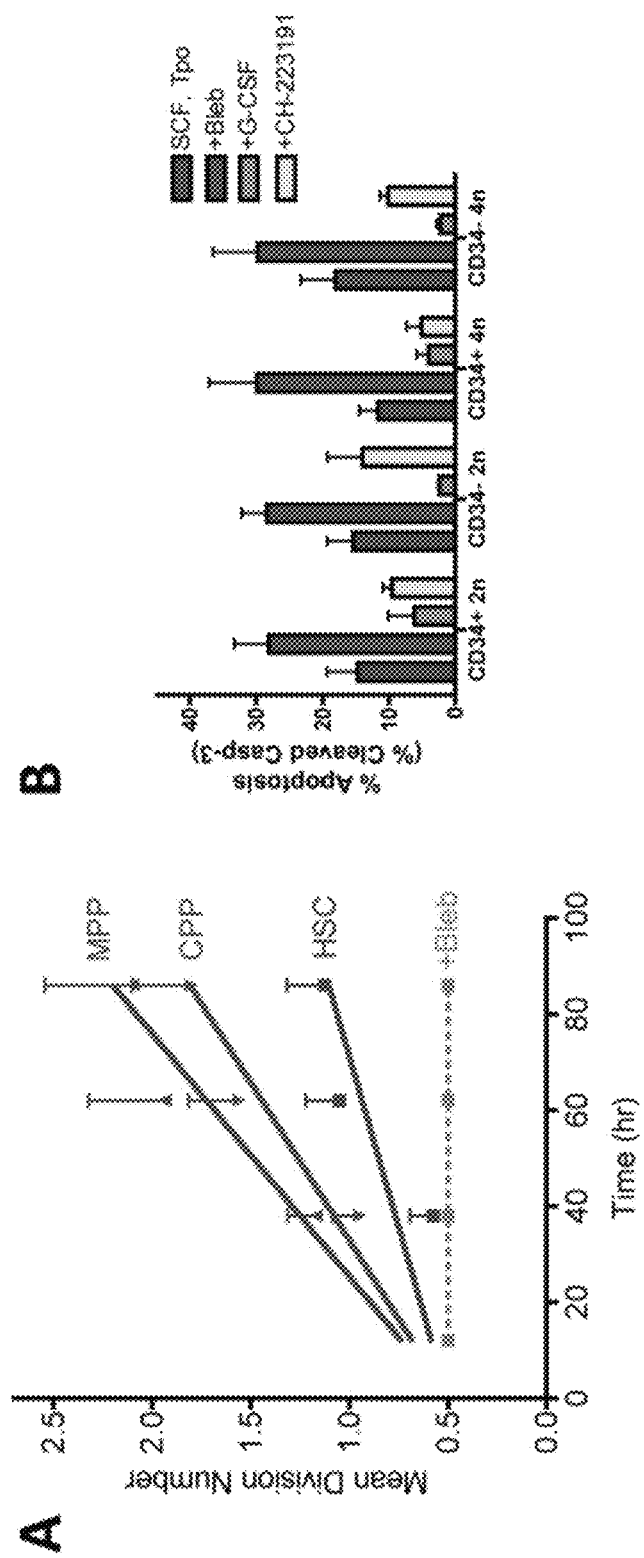
FIG. 17, comprising
Figure 17:
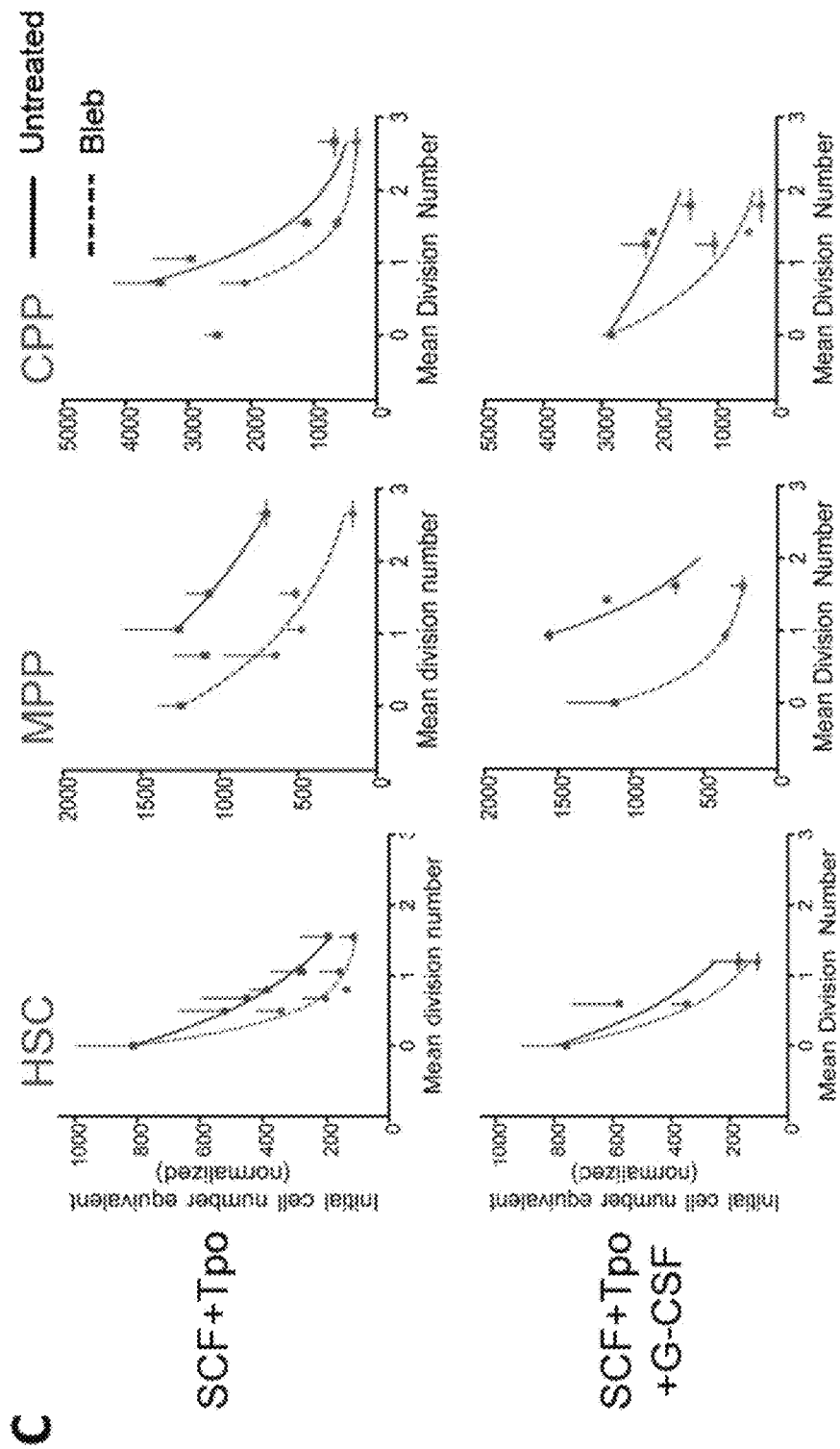
Figure 17:
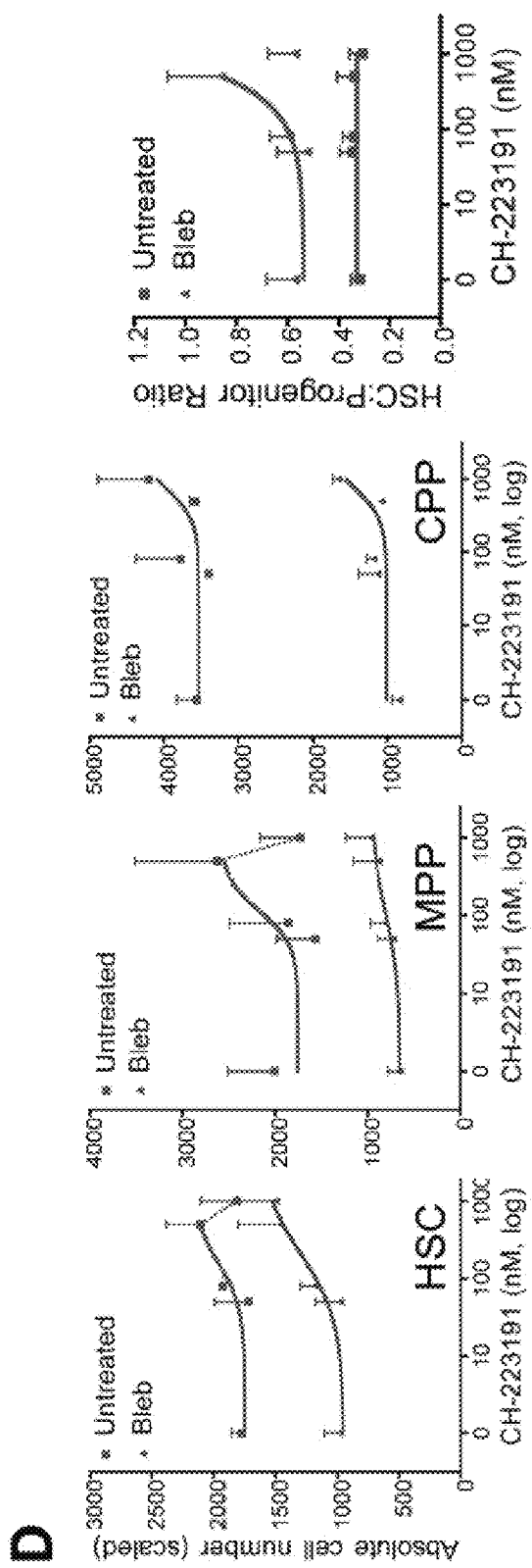
Figure 23:
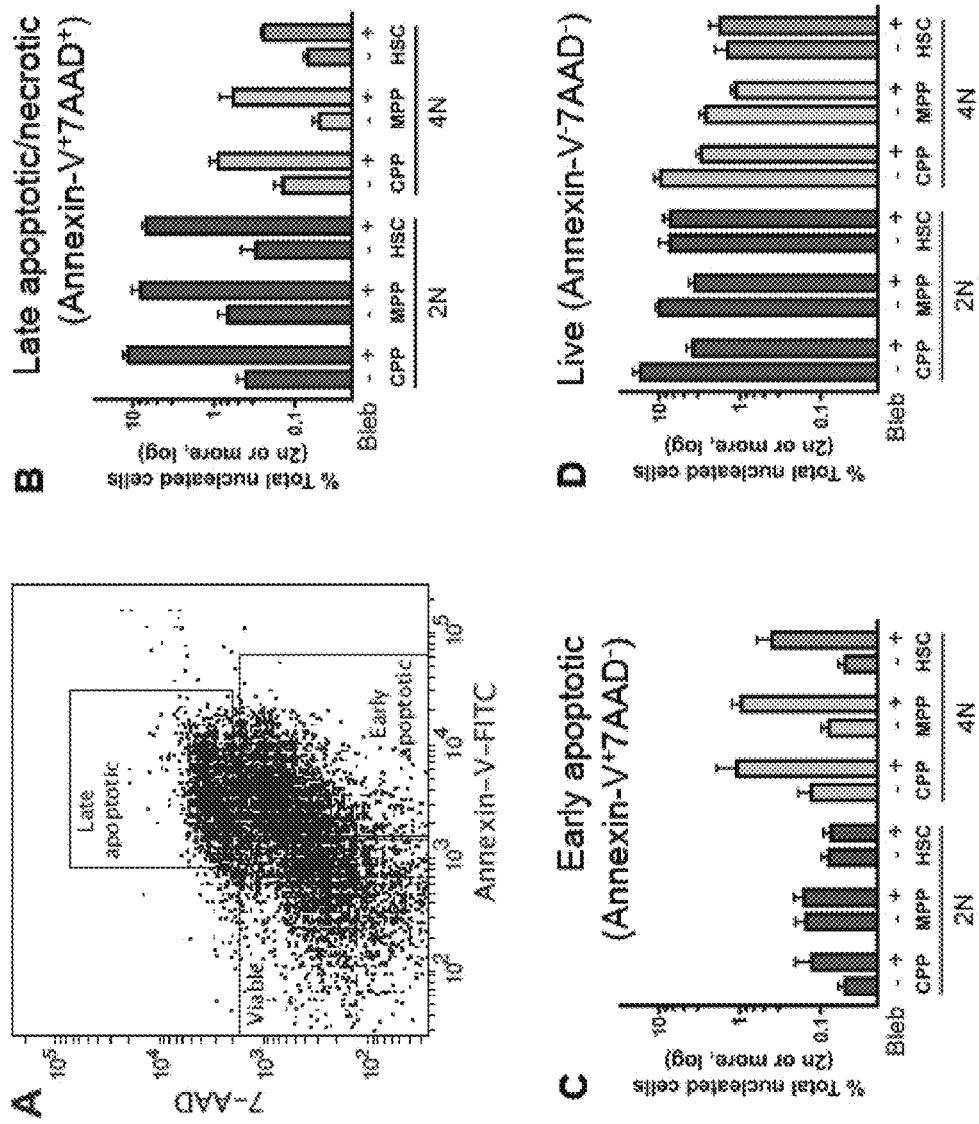
FIG. 23, comprising

Selective reduction of progenitors by Bleb could be due to inhibition of HSC/P division or else to an increase in progenitor cell death, and so cell division and viability were tracked. Cells pre-labeled with CFSE were harvested at d1 to d3 under Bleb treatment plus SCF and Tpo. For untreated cells, multiple peaks of low to high CFSE intensities were observed for each HSC/P subpopulation, allowing for the determination of the mean division number at each time point (FIG. 17A). In contrast, Bleb-treated cells remain undivided throughout the drug treatment, giving the original dye intensity for each subpopulation (flat line in FIG. 17A). Apoptosis increased about 2-fold with Bleb as indicated by increased cleaved caspase-3 expression (FIG. 17B) and Annexin-V$^+$ cells (FIG. 23). Suppression of MPP and CPP cell numbers with Bleb is therefore explained both by inhibition of cytokinesis and by cytokinesis-associated cell death. Importantly, the primitive HSC are almost unaffected in cell number by Bleb (<50% change in FIG. 15B), and so any death of HSCs is clearly matched by slow proliferation.

Figure 22:
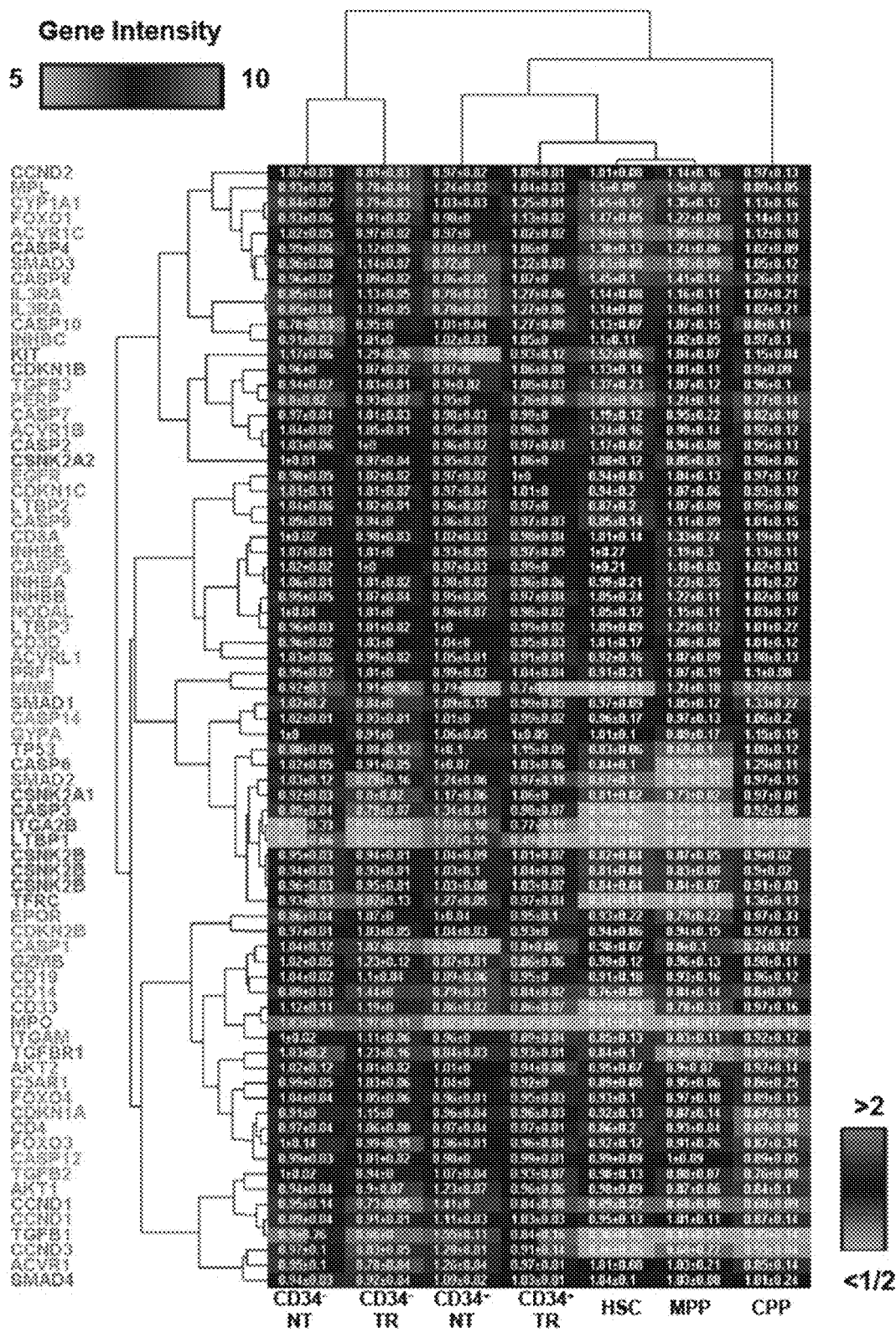
FIG. 22 depicts the expression profiles of genes relevant to HSC/P biology.

In dye-tracking of division, each peak represents a cohort of cells that entered their first division at the same time, and so one can calculate how many cells of each type underwent each division with the decay in cell number vs. division number reflecting proliferation, differentiation, and cell death. Decays for HSC, MPP, and CPP here (FIG. 17C, Top) indicate that: (1) Accumulation of the progenitors is most strongly suppressed by NMM-II inhibition, and (2) The cell decay rate is at least slightly accelerated by Bleb in all subpopulations. Interestingly, the decay half-life of Bleb-treated HSCs is improved with G-CSF (FIG. 17C, Bottom), while progenitors are more rapidly eliminated by addition of G-CSF, which leads to even greater HSC enrichment. Microarray profiling above shows as expected that the G-CSF receptor (CSF3R) is a low intensity gene that is 2-3-fold upregulated upon differentiation toward CD34$^-$ cells (FIG. 22). Consistent with this trend, G-CSF improves the viability of both untreated CD34$^+$ and CD34$^-$ cells (FIG. 17B).

Figure 24:
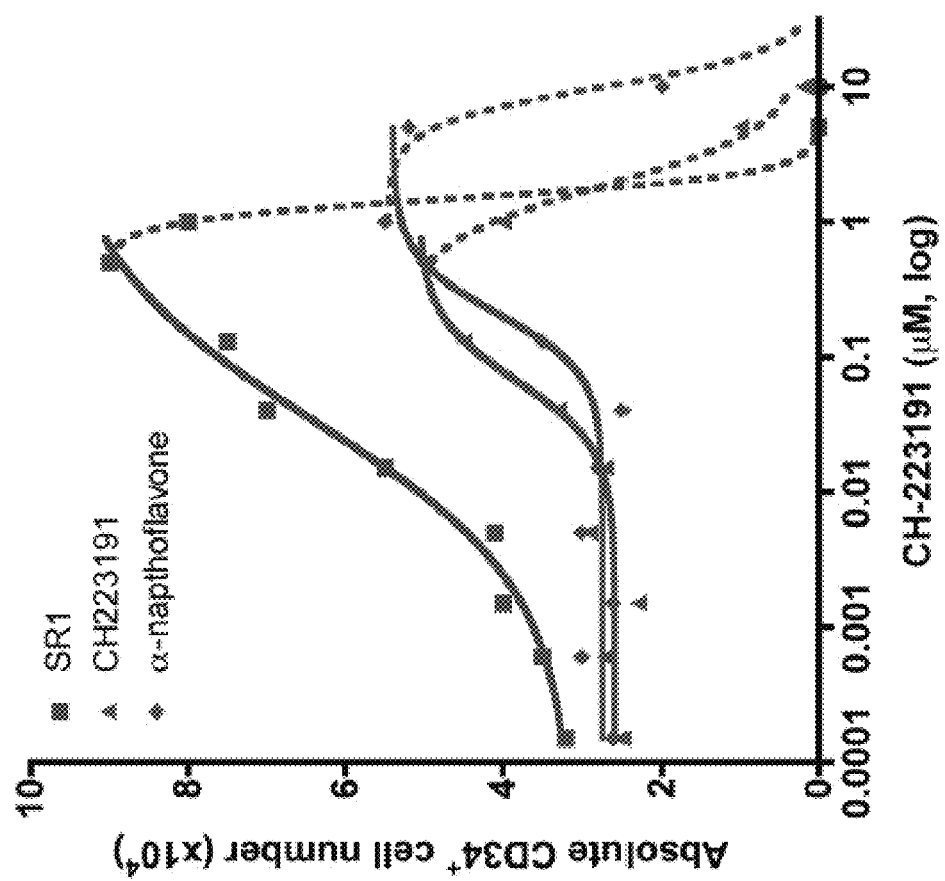
FIG. 24 depicts the dose-response effect of AHR inhibitors on CD34$^+$ cell number. Data are derived from Boitano et al. (2010) and fitted with a dose-response curve. SR1 (blue): EC50=47.4 nM, Hillslope=0.64; CH-223191 (red): EC50=74 nM, Hill slope=1.6; a-napthoflavone (green): EC50=177 nM, Hillslope=2.0. Drugs show toxic effect at 500 nM or above for SR1 and CH-223191, while 1 µM or above for α-napthoflavone.

To clarify mechanisms that underlie apoptosis upon Bleb treatment, transcription profiles of viable fraction (negative Annexin-V and 7AAD) from both untreated and drug-treated cells were obtained. The upstream initiator caspases (CASP1, 4, 8 and 10) are upregulated in treated vs. untreated CD34$^+$ (FIG. 22), indicating early induction of apoptosis in viable cells by Bleb. Consistent with previous literature, a p53 apoptosis effector (PERP), which is a direct transcriptional target of p53 and pushes cells under stress to undergo apoptosis rather than G1 arrest (Attardi et al., 2000, Genes Dev, 14(6): 704-718), is upregulated in drug-treated cells, indicating that apoptosis by Bleb accompanies induction of p53 activity. Induction of p53 is known to coincide with aryl hydrocarbon receptor (AHR)-mediated apoptosis of B-cells as triggered by polycyclic aromatic hydrocarbons (Yamaguchi et al., 1997, J Immunol, 158(5): 2165-2173), and Bleb weakly activates the AHR target gene (Cyp1a 1) not seen with NMMIIA-knockdown (Ebina et al., 2011, Biochim Biophys Acta, 1809(3): 176-183), perhaps because Bleb's multi-ring structure (Straight et al., 2003) makes it a weak AHR ligand. Cyp1a1 indeed increases reproducibly in CD34$^+$ cells with Bleb treatment (FIG. 22). AHR antagonists counteract apoptosis (Vaziri and Faller, 1997, J Biol Chem, 272 (5): 2762-2769) and can even expand the number of human HSCs and progenitors in culture (Boitano et al., 2010, Science, 329(5997): 1345-1348), although effects on hematopoietic apoptosis remain unclear. The AHR antagonist CH-223191 improves the viability of both untreated CD34$^+$ and CD34– cells, specifically for the cycling fraction (4n) (FIG. 17B). Therefore, double drug treatments might synergize with more complex pathways. CH-223191 indeed increases the cell number for each HSC/P subpopulation co-treated or not with Bleb, but the number of HSCs increases proportionately more upon dual drug treatment, coming close to cell numbers without Bleb treatment (FIG. 17D). As a result, the HSC/P ratio is almost doubled with dual drug treatment. EC50s of CH-223191 for HSC and MPP are close to the curve fit from previously reported data (Boitano et al., 2010, Science, 329(5997): 1345-1348) (FIG. 24). Therefore, inhibition of cell division by NMM-II inhibition can be at least partially isolated from concomitant apoptosis by antagonizing AHR.

Phospho-Regulation of NMM-IIA and HSC Differentiation

Regulation of NMM-II isoforms can be transcriptional but also post-translational. Phospho-regulation of myosin heavy chain has recently been reported in MK lineages, including isoform-specific phosphorylation of S1943 (pS1943) at NMM-HA, which inactivates myosin and impacts cell division (Shin et al., 2011, PNAS, 108(28): 11458-11463). Given that NMM-II is present in HSC/Ps, it seems predictable that pS1943 regulates HSC differentiation, membrane elasticity and matrix elasticity sensing (FIG. 18A). In a phospho-specific flow cytometry approach, pS1943 level proves highest in uncultured CD34$^+$ cells and decreases during differentiation with Tpo and G-CSF, but not SCF alone (FIG. 18B). Phosphorylation of S1943 is achieved by activation of EGFR, followed by the signaling through casein kinase-II (CK-II), which inactivates myosin in epithelial cells and impacts cell motility (Dulyaminova et al., 2007, Mol Biol Cell, 18(8): 3144-3155). EGF does not show a significant effect on pS1943, likely due to the background level expression of EGF receptor in fresh and CD34$^+$-derived cells (FIG. 22). However, CK-II isoforms are expressed in both fresh and cultured CD34$^+$-derived cells with A1 and B isoforms showing highest expression in untreated CD34$^+$ culture, while lowest in fresh cells. Given that TGF-beta is the only known candidate protein that leads to HSC hibernation (Yamazaki et al., 2009, Blood, 113(6): 1250-1256), the role of the TGF-beta pathway in pS1943 was investigated. TGF-beta has been recently shown to induce pS1943 in epithelial-mesenchymal transition (Beach et al., 2011, PNAs, 108(44): 17991-17996). TGF-beta receptor 1 is indeed expressed in both fresh and cultured cells, and TGF-beta 1 inhibits the reduction of pS1943 level under SCF and Tpo (FIG. 18B). The expression of other TGF-beta ligands, including Activin-1 and Nodal, is at the background level. TGFbeta 1-induced hibernation is likely to be effective in early HSCs since the downstream target Smad2 is upregulated while Smad3 is downregulated in HSC/P differentiation (FIG. 22): Increased Smad2-to-Smad3 ratio leads to desensitization of TGF-beta signaling-mediated cell cycle arrest (Kim et al., 2005, Mol Biol Cell, 16(10: 4672-4683). This explanation is also consistent with the data that both active and latent TGF-beta 1 genes become highly upregulated in differentiation (FIG. 22). Bleb indeed inhibits the reduction of pS1943 under cytokine stimulation, mimicking the effect of TGF-beta (FIG. 18B). The preservation of pS1943 level parallels with the inhibition of G1 to S cell cycle progression as indicated by 2-fold reduction of cyclin D1 and D3 (CCND1 and 3) expression by Bleb, while they are progressively upregulated in HSC/P differentiation (FIG. 22). THP-1 cells prove to be lowest in the pS1943 content, consistent with its rapid proliferation rate. Since CD34$^+$ and CD34$^-$ cell numbers depend on the level of pS1943, this trend parallels the dose-response to pharmacological NMM-II inhibitors (FIG. 15B).

Since pS1943 is localized near the cortical membrane (FIG. 18A), it may contribute to the membrane compliance of CD34$^+$ cells. To test this directly, NMM-IIA heavy chain phospho-mutants were expressed in native COS-1 and cells were subjected to micropipette aspiration. At ~1.5 kPa, cells transfected with the wild-type NMM-IIA show limited extension, whereas those transfected with phospho-mimetic mutant S1943D show decreased cytoskeletal integrity under the same pressure, leading to membrane fragmentation (FIG. 18C). Since integrin receptors are directly tethered to cortical cytoskeletons, it also seems predictable that phosphorylation of S1943 may limit matrix elasticity sensing. COS-1 cells, which consist of exclusively NMM-IIB and some NMM-IIC (Ma et al., 2010, Mol Biol Cell, 21(22): 3952-3962), are mechanosensitive for their spreading on FN gels (FIG. 18D). COS-1 cells express ~3 times higher levels of NMM-IIB protein per cell than $CD34^+$ cells (FIG. 25A). siRNA knockdown of the endogenous NMM-IIB decreases the protein level by 2 fold and eliminates mechanosensitivity. Transfection of the wildtype NMM-IIA also shows mechanosensitivity showing increased cell spreading on stiff compared to soft gels. However, phospho-mimetic mutant S1943D abolishes mechanosensitivity in a manner similar to NMM-II inhibition by Bleb in MSCs (Engler et al., 2006, Cell, 126(4): 677-689). These findings clearly indicate that NMM-IIA heavy chain phosphorylation integrates biophysical properties that regulate HSC differentiation.

Membrane Rigidity Against Shear Force Emerges in HSC Differentiation

Figure 19:
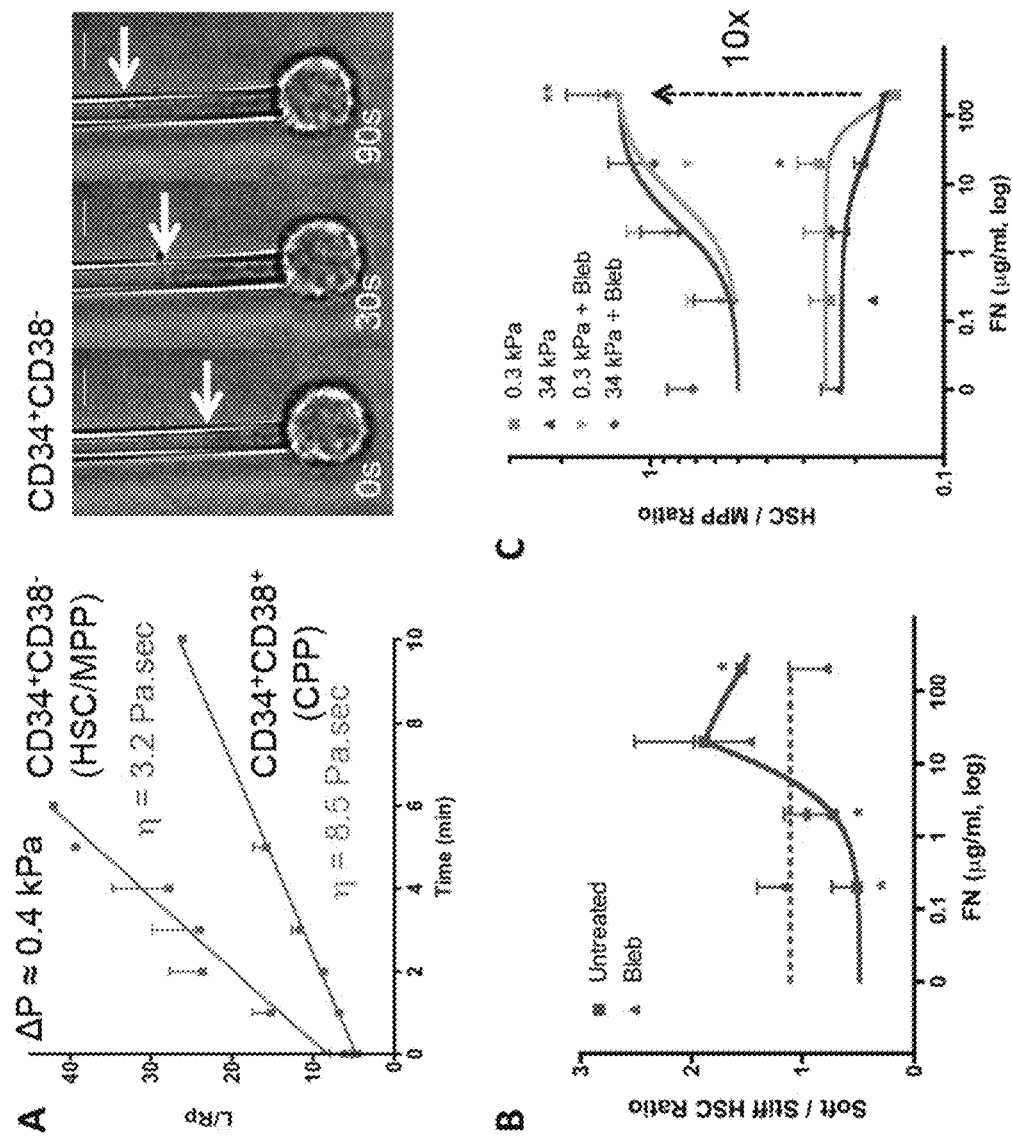
FIG. 19, comprising
Figure 25:
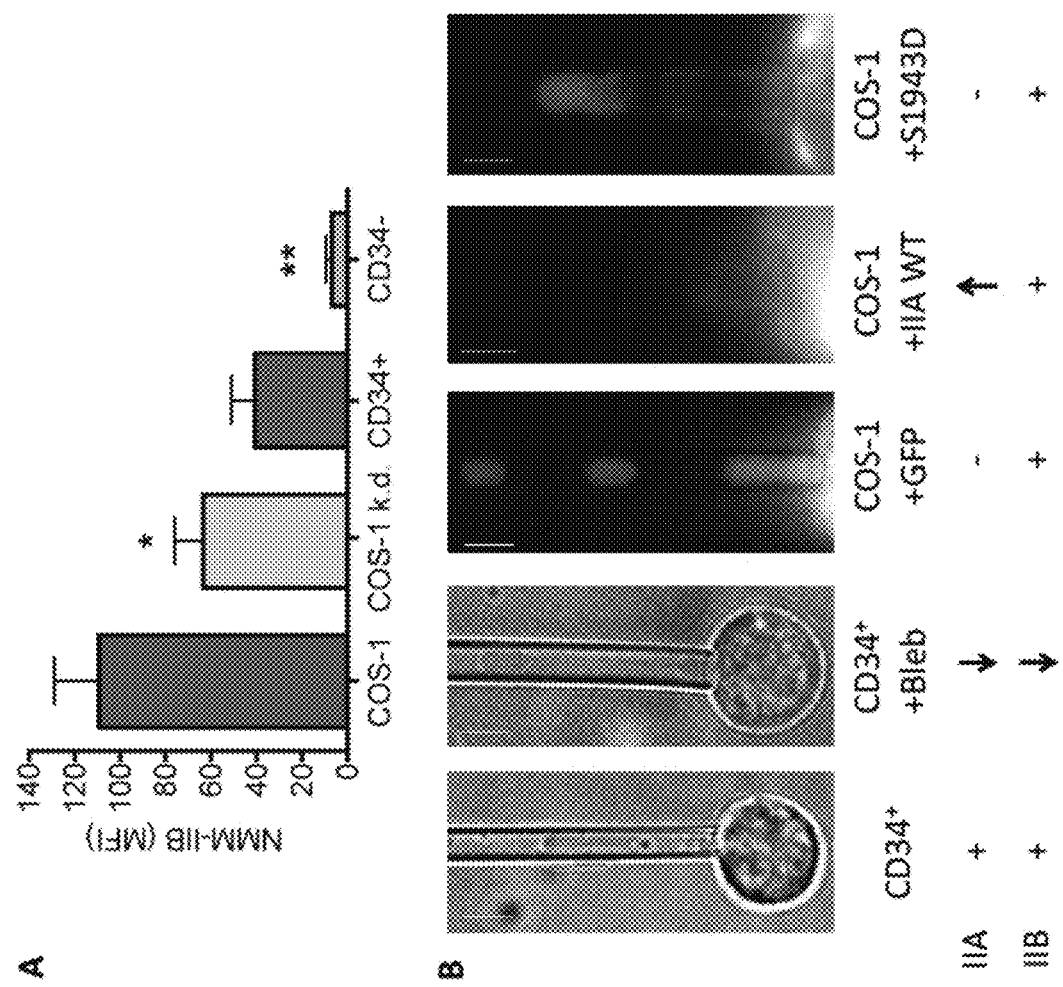
FIG. 25, comprising

Since primitive HSC/MPP cells show lower NMM-IIA and higher pS1943 level compared to mature progenitors, it was tested whether HSC membrane can be deformed easily to shear stress. Uncultured $CD34^+$ cells were labeled with the CD38 antibody and subjected to micropipette aspiration using pipettes similar to human bone marrow capillaries in diameter (3~5 μm). HSC/MPP membrane is two-fold more compliant than CPP (FIG. 19A). In general, uncultured $CD34^+$ cells are highly deformable than previously reported values from MKs (Shin et al., 2011, PNAS, 108(28): 11458-11463) with rapid extension even <1 kPa. While Bleb leads to increased membrane deformation in MKs with fragmentation in some cases, uncultured $CD34^+$ cells are still more compliant, further supporting the immature cytoskeletal structure in undifferentiated cells (FIG. 16A). In all cases, uncultured $CD34^+$ cells exhibit rapid membrane fragmentations without further increases in membrane elasticity after 30 min of Bleb (FIG. 25B). It is likely that membrane elasticity is regulated specifically by the NMM-IIA isoform, since COS-1 cells predominantly express the heavy-duty isoforms NMM-IIB and IIC, but not IIA (Ma et al., 2010, Mol Biol Cell, 21(22): 3952-3962), yet their membrane is easily fragmentable under low pressure (<3 kPa) micropipette aspirations, which can be rescued by the overexpression of IIA (FIG. 25B).

Figure 26:
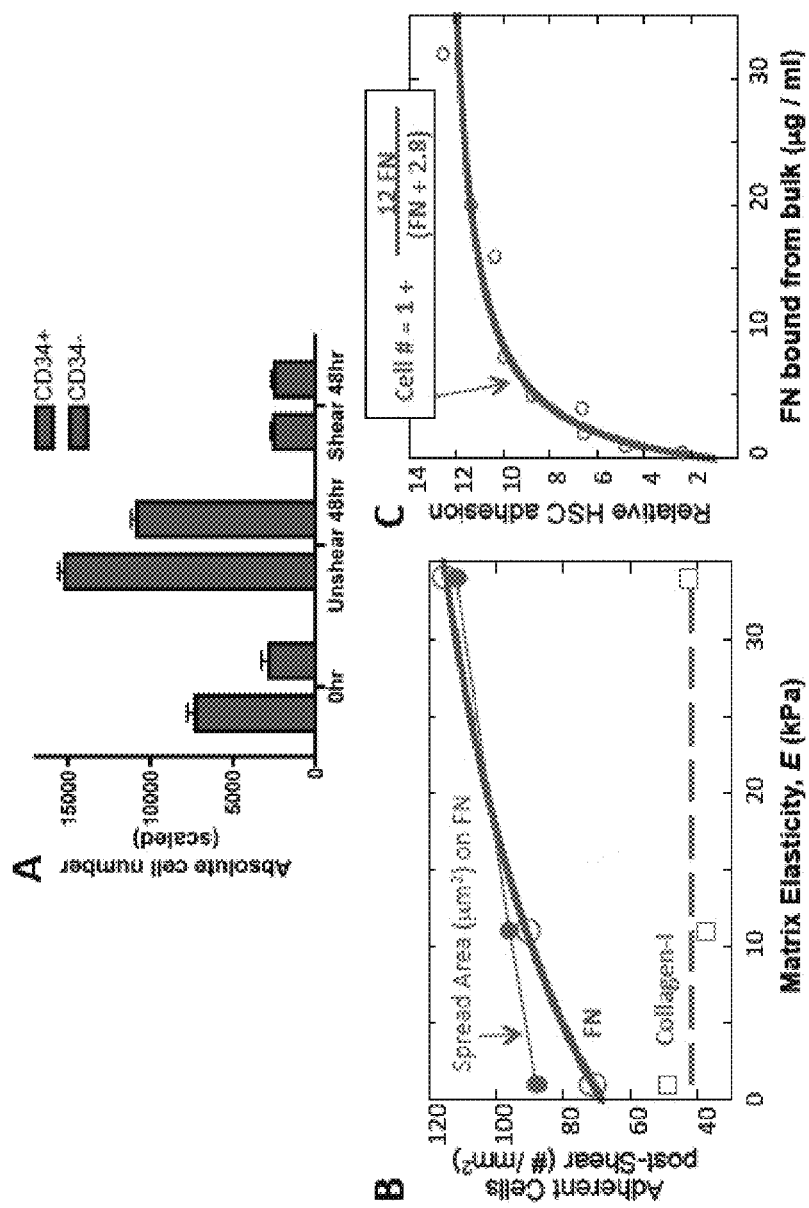
FIG. 26, comprising
Figure 26:
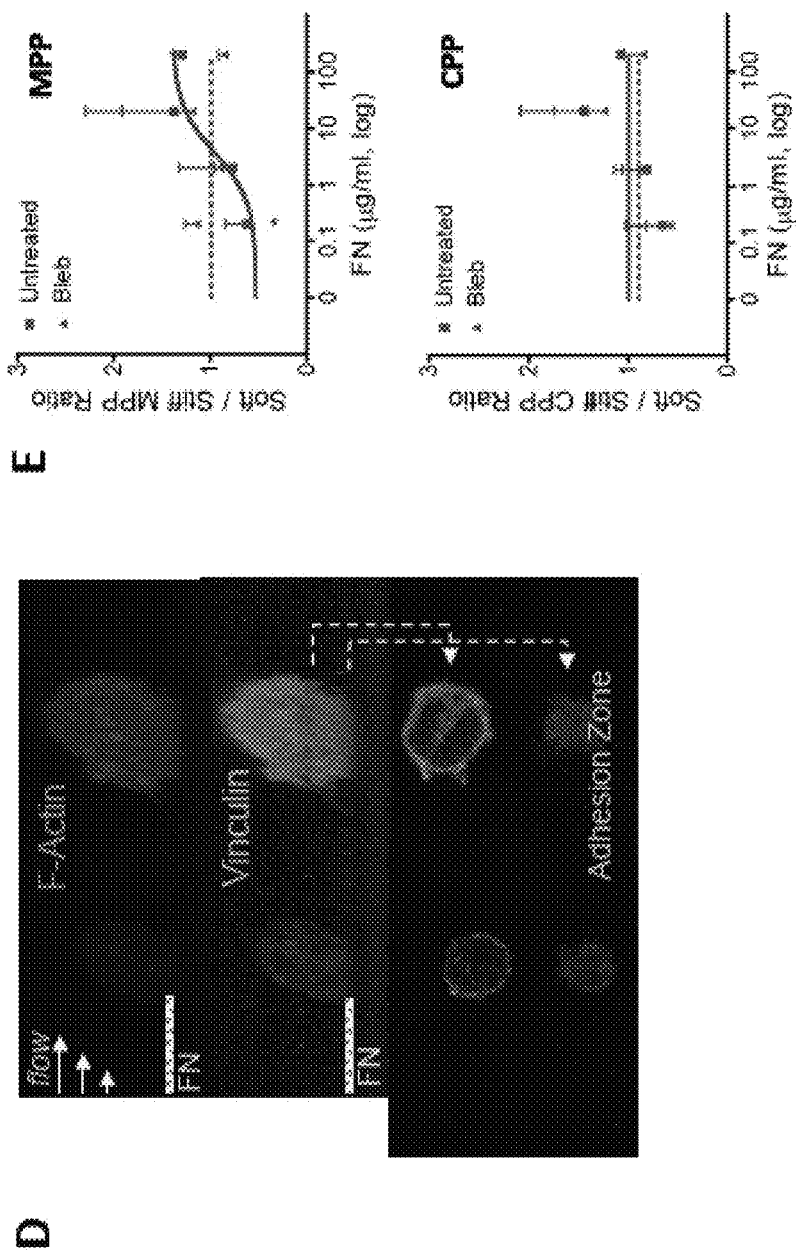

Given that undifferentiated HSCs are relatively flexible and fluid compared to differentiated cells, they may be vulnerable to shear-induced molecular changes that could in turn lead to differentiation. Indeed, shear force stimulates HSC differentiation in embryos (Adamo et al., 2009, Nature, 459(7250): 1131-1135), but it remains unclear whether this can also be observed in adult cells. Given that NMM-IIA and NMM-IIB are markers for early and late HSC differentiation, respectively (FIG. 16A), $CD34^+$ cells were cultured under shear using a simple incubator shaker and their relative differentiation levels as well as NMM-II expression were evaluated. Continuous shear over 48 hr leads to the specific suppression of the total $CD34^+$ number, while the total $CD34^-$ number remains unaltered (FIG. 26A). The total NMM-IIA, pS1943 and NMM-IIB contents per cell were not changed after shear. This suggests that $CD34^+$ cells may be more vulnerable to shear stress than $CD34^-$ cells, and that shear suppresses cell proliferation, which might be different from embryonic development and might fit with low shear in the bone marrow microenvironment.

Matrix Density and Elasticity Influence Early HSC Differentiation

Cells in BM interact with ECM in vivo. Both osteoblasts (OBs) at the stiff endosteum and endothelial cells at soft marrow space are known to regulate HSC number but in a distinct manner. While OBs maintain HSC quiescence (Calvi et al., 2003, Nature, 425:841-846), endothelial cells facilitate self-renewing HSC/P expansion (Butler et al., 2010, Cell Stem Cell, 6(3): 251-264). A number of soluble factors or surface receptors from each cell type have been implicated in HSC functions, but physical attributes of ECM, including density and elasticity remain to be investigated. Previously, extensional elasticity of tropoelastin expands both HSC/Ps by ~3 fold (Holst et al., 2010, Nat Biotechnol, 28(10): 1123-1128), but it remains to be investigated whether elastin exists physiologically in BM.

The predominant integrin for early HSCs and progenitors is alpha 4 (FIG. 16A), which interact with FN (Yoder and Williams, 1995, Exp Hematol, 23: 961-967). FN is a ubiquitous matrix distributed throughout bone marrow with higher concentration near the endosteum (Nilsson et al., 1998, J Histochem Cytochem, 46:371-377). The bone surface is stiff with an estimated elasticity $E_{ECM}$=~34 kPa (Engler et al., 2006, Cell, 126(4): 677-689), while the marrow space is soft with $E_{ECM}$=0.3 kPa (Winer et al., 2009, Tissue Eng Part A, 15:147-154). Therefore, it seems inevitable that migrating $CD34^+$ cells, progenitors and differentiated cells in BM encounter heterogeneous tissue elasticity and FN density. To directly test whether these physical factors affect early HSC proliferation and differentiation, $CD34^+$-derived cells were cultured with 2 cytokines, SCF and Tpo, on polyacrylamide gels with controlled stiffness functionalized by different FN concentrations per previous studies (Rajagopalan et al., 2004, Biophys J, 87(4): 2818-2827). Indeed, $CD34^+$ cells are capable of anchoring to FN selectively compared to collagen-I, where a background level of adhesion was observed (FIG. 26B). This is consistent with the observation that alpha 4 integrin expression is generally high, while alpha 2 integrin is low with upregulation during differentiation (FIG. 16A). The selectivity of $CD34^+$ adhesion against FN was also demonstrated by matrix density dependence (FIG. 26C) and the presence of adhesion zone at the cell-matrix interface under shear (FIG. 26D). In analyzing HSC/P subpopulations, HSC number appears to be the most sensitive to matrix elasticity with a 2-fold increase on either stiff (34 kPa) at low FN concentrations (0.2-2 μg/ml) or soft (0.3 kPa) at higher FN concentrations (20-200 μg/ml) in a NMM-II dependent manner (FIG. 19B). MPP number shows a similar trend as HSC number (FIG. 26E, top panel). Interestingly, CPP number is not significantly dependent on matrix elasticity (FIG. 26E, bottom panel). This observation is consistent with the microarray analysis that HSC and MPP defined in this study are significantly closer to each other than CPP in terms of cytoskeletal and integrin gene expression profiles (FIG. 16A).

While HSC/P numbers are generally suppressed on stiff and high density FN matrix, decreased HSC number on stiff and high-density matrix is due to increased MPP number relative to HSC (decreased HSC-to-MPP ratio), indicating increased differentiation (FIG. 19C). As expected from FIG. 3.1B, the HSC-to-MPP ratio for Bleb-treated cell become ~4 fold higher than untreated cells on plastic due to selective elimination of MPP. The ratio becomes significantly higher (>2 fold) with increasing FN density for the drug-treated cells. The matrix elasticity effect is indeed due to increased CD34$^+$ cell adhesion on FN matrix as more cells remained anchored to stiff matrices vs. soft matrices with increased cell spreading (FIG. 26B). Therefore, soft and high-density FN matrices facilitate the expansion of HSCs and MPPs, while stiff and high-density FN matrices may increase progenitors relative to HSCs under cytokine stimulating culture conditions.

Figure 3:
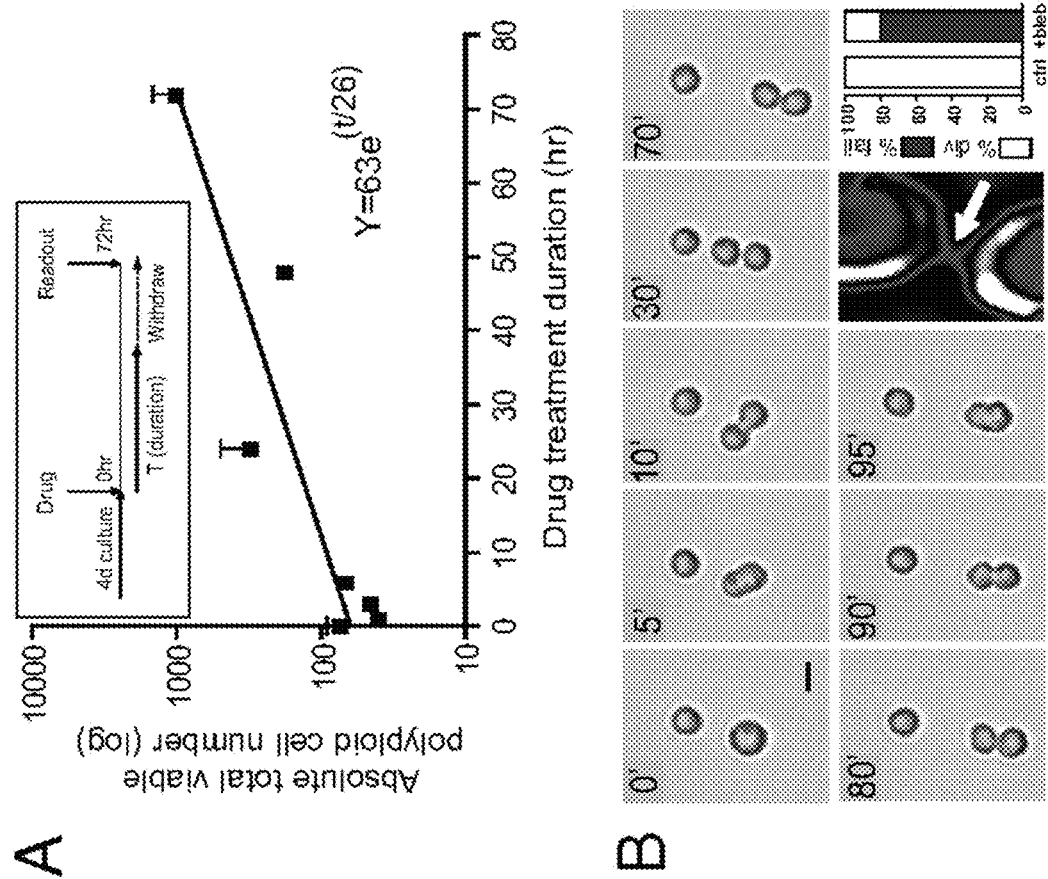
FIG. 3, comprising
Figure 20:
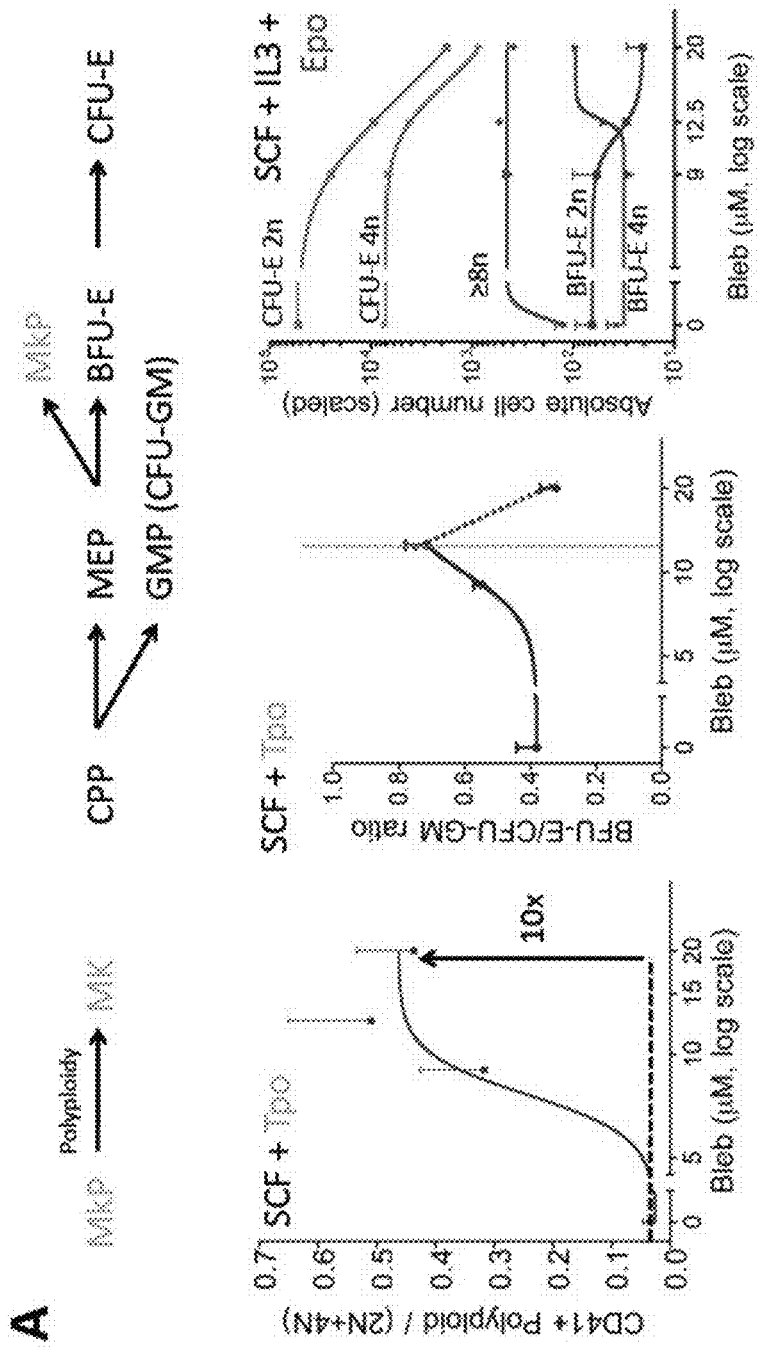
FIG. 20, comprising
Figure 20:
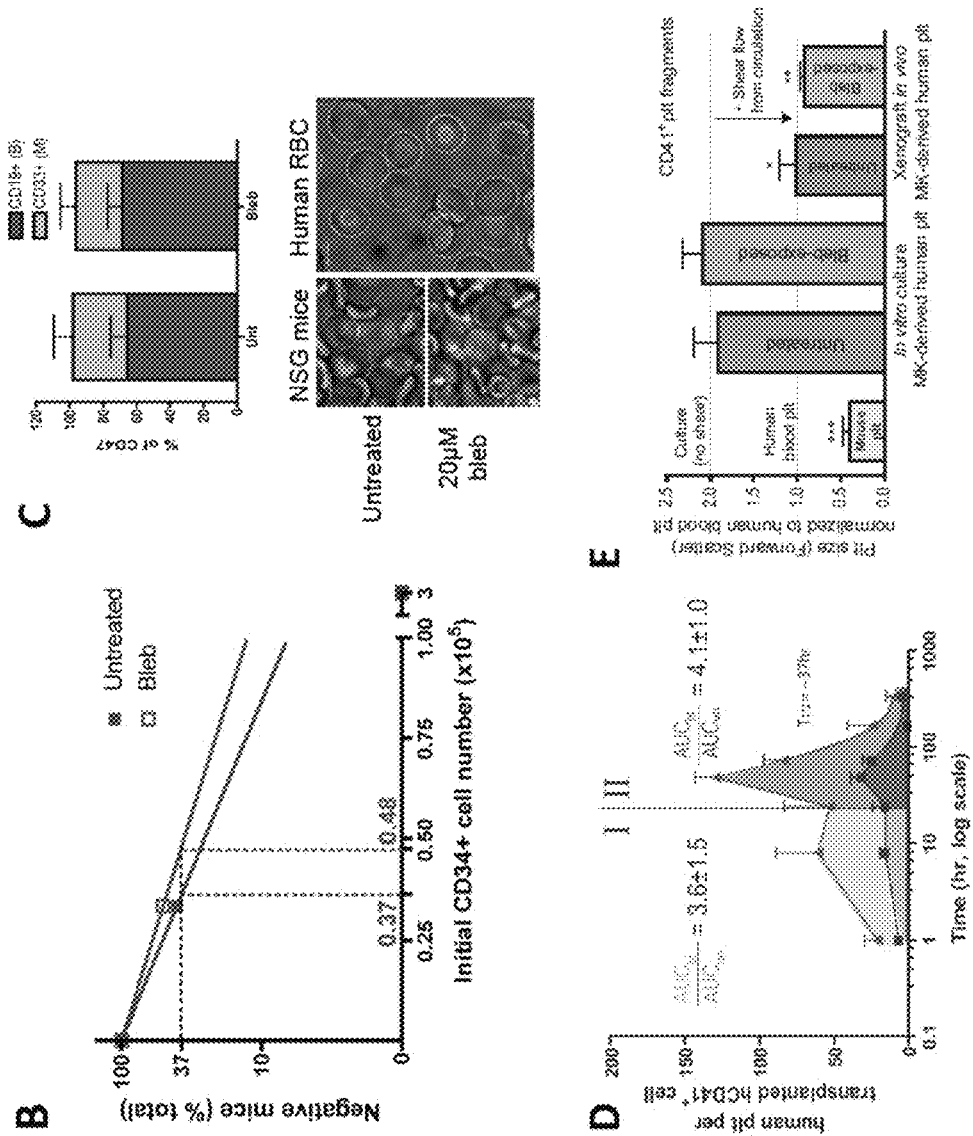

Reversible NMM-II Inhibition Enriches for HSCs with Functional Hematopoietic Reconstitution In Vivo Since sustained but reversible NMM-II inhibition both eliminates proliferating progenitors and suppresses HSC division, the functional impact of drug treatment on differentiation in vitro was first tested. Since MKs undergo maturation by polyploidization, it was examined whether NMM-II inhibition blocks cytokinesis, thereby increasing MK maturation and eventually plt fragmentation (Shin et al., 2011, PNAS, 108(28): 11458-11463). Indeed, Bleb enriches for mature polyploid MKs by ~10 folds (FIG. 20A, left panel). As in FIG. 3.1B, the number of colony-forming progenitors is generally reduced by Bleb (FIG. 27A). However, the sensitivity of individual progenitor lineages against the drug proves dependent on cytokines. When CD34$^+$-derived cells are cultured under SCF and Tpo and treated with Bleb, the IC50 value of colony forming unit-granulocyte and monocyte (CFU-GM) is lower (and closer to the reported IC50 value for the drug) than that of BFU-E, leading to the increased BFU-E to CFU-GM ratio by 2 fold at 12.5 µM (FIG. 20A, middle panel). Erythroid lineages are thus preserved under non-Epo and submaximal NMM-II inhibition. In contrast, when cells are cultured with SCF, IL3 and Epo, both CFU-E and BFU-E numbers are reduced at an IC50 closer to that of the drug (FIG. 3.6A, right panel). Therefore, NMM-II is required for lineage-specific differentiation under defined cytokines.

The observations above are consistent in many ways with the molecular profiles of the different cell cultures. Fresh CD34$^+$ cells express no more than 2-fold higher SCF receptor (KIT) than SCF+Tpo cultured CD34$^+$ cells, with Bleb-treated CD34$^+$ cells showing 1.8-fold higher expression than untreated CD34$^+$ cells (FIG. 22). SCF receptor is upregulated 2-fold in cultured CD34$^-$ vs. CD34$^+$ cells, suggesting the possible presence of mast cells and basophils. The possible presence of neutrophils and monocytes is suggested by strong upregulation (20-fold) of myeloperoxidase (MPO) in cultured CD34$^-$ vs. CD34$^+$ cells, with high expression also apparent in fresh CPP. This observation is also supported by 2-fold upregulation of CD33 (pan-myeloid marker) and CD14 (expressed in neutrophils and monocytes) in CD34$^-$ vs. CD34$^+$ cells, while other markers for differentiated myeloid cells (e.g., CD123, CD11b, and CD88) show background expression levels. The injected cells also appear to possess both erythroid and megakaryocytic potential. While they consist of few mature erythroid cells based on background levels of Glycophorin A (GYPA) and EPO-R expression, they do contain early erythroid progenitors as suggested by high gene intensities for CD71 (TFRC) in CD34$^+$ cells (FIG. 22). As expected, Bleb-treated CD34$^+$ cells (lower number of CPP) express lower CD71 than untreated CD34$^+$ or fresh CPP. Given that the culture medium contained Tpo, CD41 (ITGA2B) and CD61 (ITGB3) are >10-fold upregulated in cultured CD34$^+$ cells compared to background levels in fresh cells, although Bleb in culture suppresses these cytoskeleton-linked adhesion proteins. The cultured cells do not appear to contain early lymphoid progenitors since the level of CD10 (MME) remains very low (Ichii et al., 2010), compared to fresh CPP, which shows upregulation by 20-fold. The late lymphoid markers, including CD10, CD4, CD8A, CD19, CD3, perforin (PRF1) and granzyme B (GZMB), are expressed at low background levels in both cultured and fresh cells.

To test if HSCs enriched by NMM-II inhibition are functional, nucleated cellular fractions of CD34$^+$ cells with SCF and Tpo with or without Bleb were xenografted into NSG mice. The frequency of repopulating human cells (SCID-repopulating cells, SRCs) was determined by analyzing bone marrow at 16 weeks post-transplantation using limiting dilution analysis. The results show a similar number of repopulating cells after 1-week culture in Bleb (1 in 4.8×10$^4$ initial CD34$^+$ cells) compared to fresh HSCs (1 in 3.7×104; P=n.s.) (FIG. 20B). A slightly lower number with Bleb treatment is likely due to accelerated HSC apoptosis as in FIG. 3.3B. These frequency values are lower than previously reported values for transplantation with uncultured CD34$^+$ cells (Boitano et al., 2010, Science, 329(5997), likely due to the fact that CD34$^+$ cells were cultured at the minimal cytokines for 4 days and drug-treated for 3 additional days before transplantation. In terms of total cell number injected, Bleb enriches as expected for HSCs by 4-fold increase in frequency (FIG. 27B). This number is lower than the >10-fold enrichment of HSCs among CD34$^+$ cells in FIG. 3.1B because 'total cells' contains a significant number of CD34$^-$ cells which contribute to the background of non-repopulating cells. Both untreated and Bleb-treated human cells are capable of producing comparable percentage of myeloid and lymphoid lineages (FIG. 20C, top panel) and also a minor amount of enucleated RBCs in the NSG mice (FIG. 20C, bottom panel), which could be isolated from millions of cells by flowing them through the microfluidic channel coated with the human antibody against CD47, and identified by staining for hGPA (FIG. 27C). HSCs from drug-treated and untreated are capable of self-renewing as indicated by positive engraftment in secondary transplantation (FIG. 27B), indicating that they are bona-fide functional HSCs.

Studies suggested that the same drug-treated culture condition increases MK polyploidy and plt generation from human CD41$^+$ cell by 3-4 folds after a 3 day intrabone implantation (Shin et al., 2011, PNAS, 108(28): 11458-11463). A more complete quantitation here of circulating human-CD41$^+$ plts identified up to 2 wks after transplantation suggests two phases of circulation (FIG. 20D). In phase-I, human plts or proplatelets are released into the circulation almost immediately and reach an initial peak sometime between 1~20 hrs, which seems consistent with results for intravenously infused MKs (FIG. 27D) (Fuentes et al., 2010, J Clin Invest, 120:3917-3922). Phase-II peaks at 20~90 hrs and reflect MK that successfully lodge in the marrow. Importantly, in both phases, human cells treated with Bleb generate more human plts per transplanted CD41$^+$ cell by about 4-fold. As an important indicator of equivalent homeostatic plt function, Phase-II's exponential decay indicates a plt half-life regardless of drug treatment of ~37 hr, which is consistent with previous studies of human plts generated in mouse (Salles et al., 2009, Blood, 114:5044-5051). In addition to its role in regulating HSC differentiation, shear force proves to be important in regulating the size of human plts derived from MKs, since CD41$^+$ fragments derived from culture are 2 fold larger than those derived from circulation from human and the NSG mice transplanted with human MKs (FIG. 20E). Therefore, the functional studies indicate that NMM-II inhibition in combination with the specific cytokine combination (SCF and Tpo) offers a means to simultaneously enrich for LT-HSCs, erythroid progenitors and mature MKs.

Enrichment of Engraftable HSCs by NMM-II Inhibition

The cytoskeleton is traditionally implicated in modulating mechanosensivity of large adherent stem cells such as MSCs (Engler et al., 2006, Cell, 126(4): 677-689). HSCs are normally non-adherent in culture but their interactions with ECM in BM are unavoidable in vivo. Integrin receptors regulate HSC functions: (1) Alpha 4 and alpha 5 integrins regulate HSC adhesion to FN and BM mobilization (Papayannopoulou and Nakamoto, 1993, PNAS, 90(20): 9374-9378; van der Loo et al., 1998, J Clin Invest, 102(5): 1051-1061); (2) Alpha 2 distinguishes between long and intermediate-term HSCs (Benveniste et al., 2010, Cell Stem Cell, 6(1): 48-58); (3) Alpha 6 differentiates between LT-HSCs and MPPs (Notta et al., 2011, Science, 333(6039): 218-221). Their downstream Rho GTPases play roles in HSC migration and homing (Cancelas et al., 2005, Nat Med, 11(8): 886-891). However, general roles of the cytoskeleton in modulating biophysical aspects of adult hematopoiesis remain unclear. Myosin-II plays an integrative role in stem cell differentiation here, including cytokinesis, matrix sensing, and membrane elasticity Inhibition of NMM-IIA over several cell cycles leads to enrichment of HSCs by suppression of HSC division and elimination of progenitors by accelerated apoptosis. Increased apoptosis by Bleb is due to induction of p53 and is inhibited by AHR antagonism. HSCs in BM are surrounded by mitogenic signals released by their niche cells, and hence active suppression of cell division seems necessary to maintain HSC quiescence. Data presented herein suggests that inhibition of NMM-II is the downstream signal that acts to suppress cell division. A physiological pathway of myosin-II deactivation via S1943 phosphorylation may involve transient signaling from HSC-specific upstream factors, including TGF-beta, which is a candidate hibernation signal (Yamazaki et al., 2009, Blood, 113(6): 1250-1256) and prevents downregulation of pS1943 during differentiation (FIG. 18B). To prevent apoptosis when myosin-II is inhibited under differentiating conditions, it seems plausible that an unidentified parallel physiological mechanism may exist to inhibit AHR or p53 induction in HSCs. A recent study supports this possibility since p53 neutralization by Bcl2 over expression preserves in vivo repopulating HSC function against radiation-induced apoptosis (Milyaysky et al., 2010, Cell Stem Cell, 7(2): 186-197).

Figure 27:
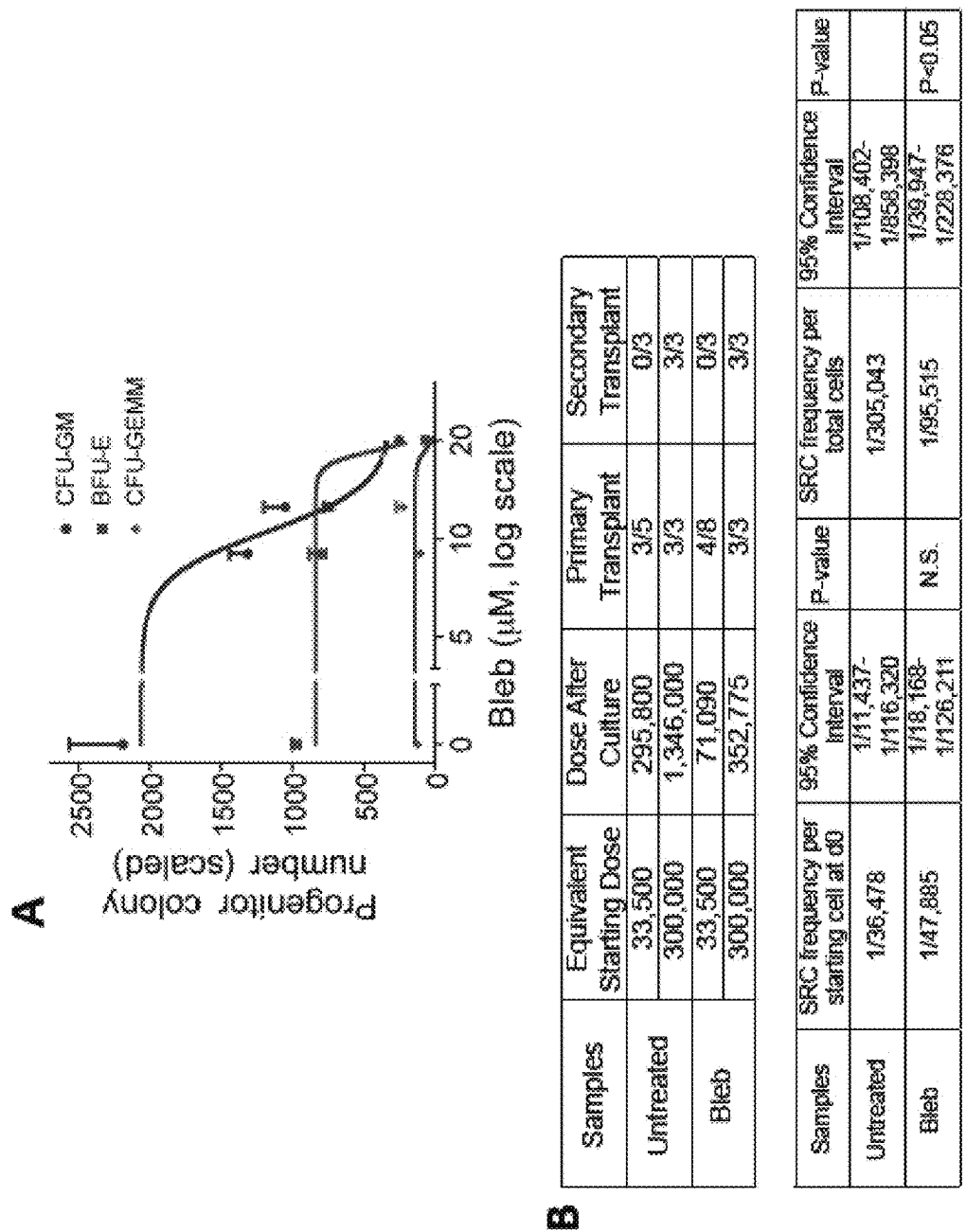
FIG. 27, comprising
Figure 27:
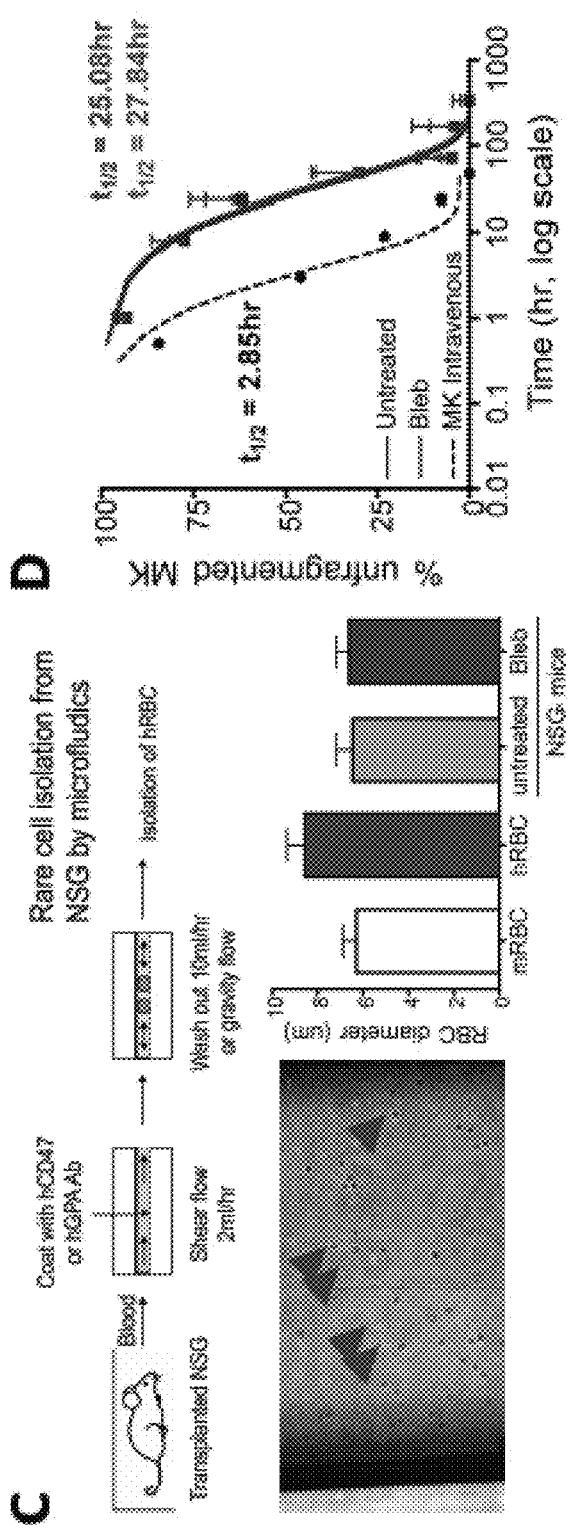

The endosteum consists of OBs and high-density stiff ECMs, and has been traditionally associated as a key contributor to the niches for LT-HSCs (Calvi et al., 2003, Nature, 425:841-846; Schofield, 1978). However, HSCs are also observed nearby sinusoidal blood vessels and perivascular cells (Kiel et al., 2005, Dev Biol, 283(1): 29-39), which facilitate HSC/P expansion (Butler et al., 2010, Cell Stem Cell, 6(3): 251-264). In addition, nestin-positive MSCs (Mendez-Ferrer et al., 2010, Nature, 466(7308): 829-834) and CXCL12-abundant reticular cells (Sugiyama et al., 2006, Immunity, 25(6): 977-988) are required to maintain HSCs in BM. HSC quiescence and differentiation induced by soluble stimuli or receptor engagement from these niche cells have been well described, but the results here report an influence of microenvironment stiffness on HSC/Ps. Under high FN concentrations (20-200 μg/ml), both HSCs and MPPs expand on soft matrices (0.3 kPa), while they are suppressed on stiff matrices (34 kPa) after 3 days in culture (FIG. 19B, FIG. 27). This indicates that moderate levels of adhesion are required to achieve an optimal HSC or MPP number. This is consistent with previous studies showing that mouse Lin$^-$Sca-1$^+$cKit$^+$ (LSK) cells do not expand on crosslinked stiff tropoelastin after the same period of time of cell culture, while they expand on soft tropoelastin (Holst et al., 2010, Nat Biotechnol, 28(10): 1123-1128). Since rapidly proliferating CPPs (FIG. 17C) are not sensitive to matrix elasticity (FIG. 26E, bottom panel), it is possible that at least in the hematopoietic system, actomyosin forces can be re-distributed from cell adhesion to cytokinesis during rapid cell proliferation, eliminating the cell's sensitivity to matrix elasticity.

The polyacrylamide-based hydrogel system used in the present study recapitulates matrix elasticity observed in different regions of BM directly measured in vivo by atomic force microscopy (0.3~3 kPa for BM and >100 kPa for inner bone surface) (Winer et al., 2009, Tissue Eng Part A, 15:147-154). However, HSC/Ps interact directly with niche cells in BM. Therefore, it will be useful to study them directly on a cellular system where cells' stiffness can be controlled. Interestingly, a previous report indicates that Akt-activated endothelial cells facilitate HSC/P expansion, while MAPK-activated endothelial cells maintain HSC/Ps and shift towards differentiation (Kobayashi et al., 2010, Nat Cel Biol, 12(11): 1046-1056). Interestingly, MAPK activation is required for endothelial stiffening response (Wang and Doerschuk, 2001, J Immunol, 166(11): 6877-6884). Given that soft matrices increase HSC and MPP numbers, and that stiff matrices increase MPP relative to HSC at high FN densities (FIGS. 19B and C), it remains to be investigated whether Akt activation can soften endothelial cells, while MAPK activation can stiffen the cells.

Paradoxically, a previous study with different adherent cell types shows that increased adhesion and stiffness on FN between 2-24 kPa are associated with increased cell proliferation (Klein et al., 2009, Curr Biol, 19(18): 1511-1518). While not wishing to be bound by any particular theory, this is probably because HSC/Ps have an inherent capability to divide without matrix in culture, while adherent cell types require matrix to survive. Non-adherent cell types are generally small with low cytoskeletal contents, and hence matrix engagement could provide enough force to immobilize cells, leading to inhibition of cell division (DiMilla et al., 1991, Biophys J, 60(1): 15-37). However, matrix provides enough traction forces for adherent cell types with relatively higher cytoskeletal contents, facilitating cell division. Contrary to previous observations where HSC is kept quiescent at the endosteal niche (Arai and Suda, 2007, Adv Exp Med Biol, 602: 61-67), CD34$^+$ cells on stiff matrix appear to undergo differentiation as indicated by increased MPP relative to HSC (FIG. 19C). This indicates that matrix engagement alone may not be sufficient to keep HSCs at quiescence under cytokine stimulating conditions. This is consistent with a priming role of matrix elasticity for soluble factors (Engler et al., 2006, Cell, 126(4): 677-689). This further corroborates the observation that NMM-II inhibition is a dominant factor that can actively put cells into quiescence against stimulatory signals.

Figure 16:
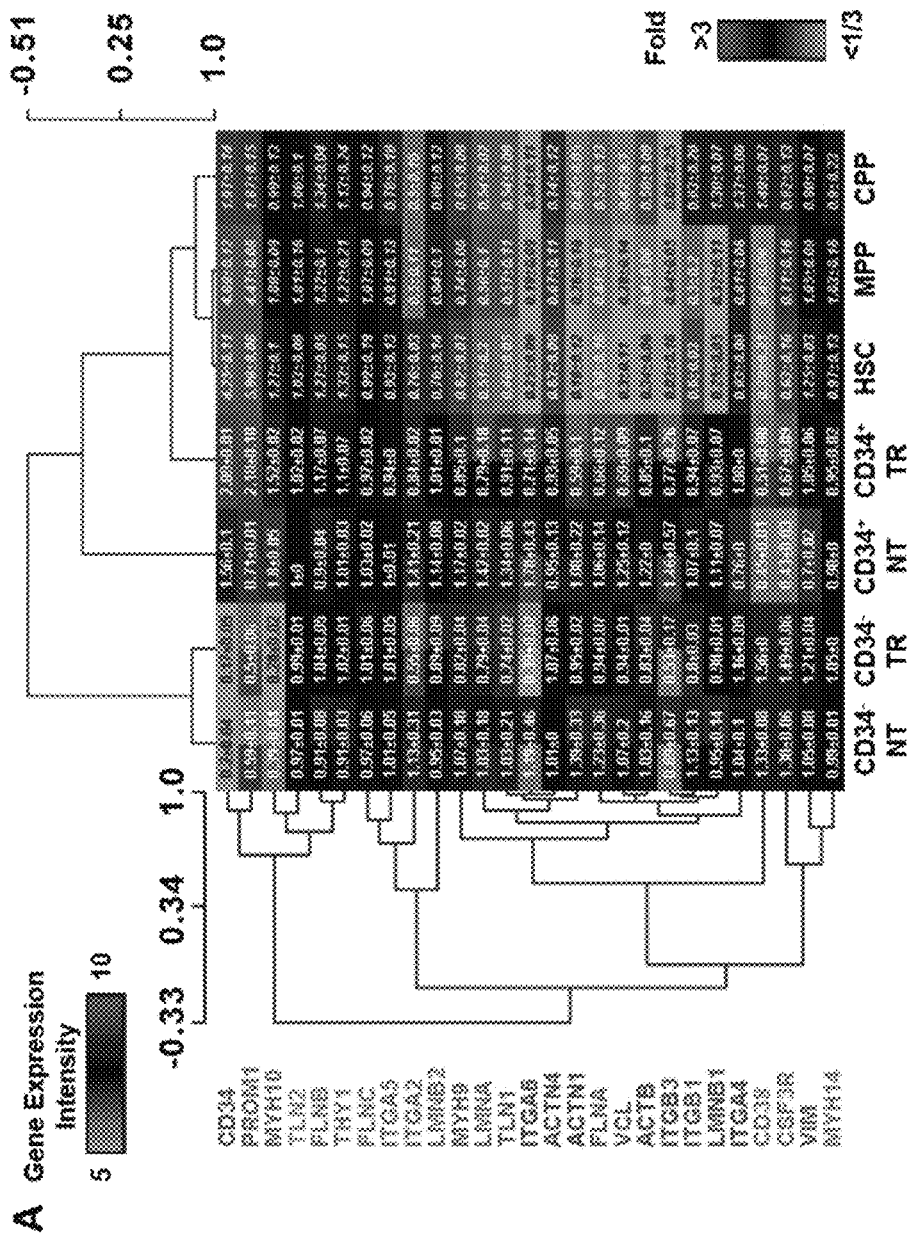
FIG. 16, comprising FIG. 16A and FIG. 16B, demonstrates that HSC differentiation accompanies global upregulation of cytoskeletal gene expression and myosin-II isoform switching.
Figure 16:
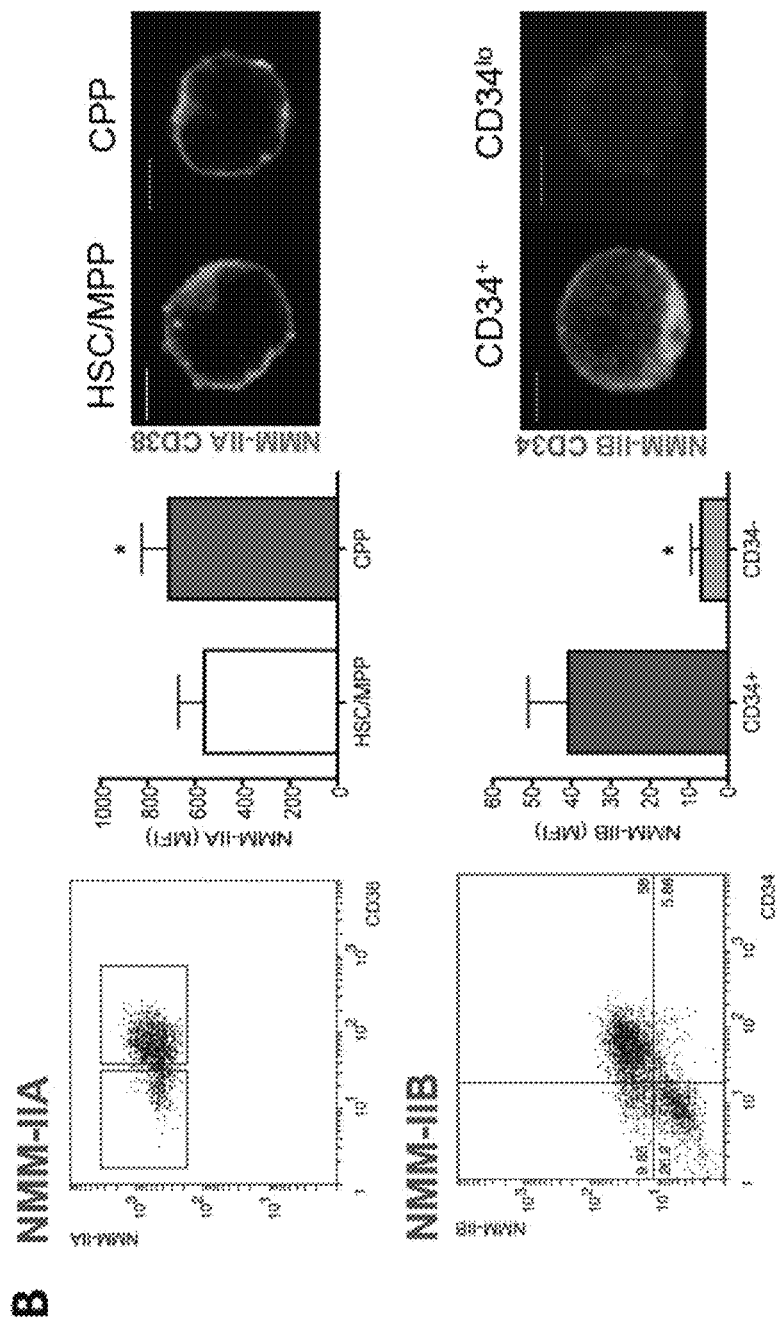
Figure 18:
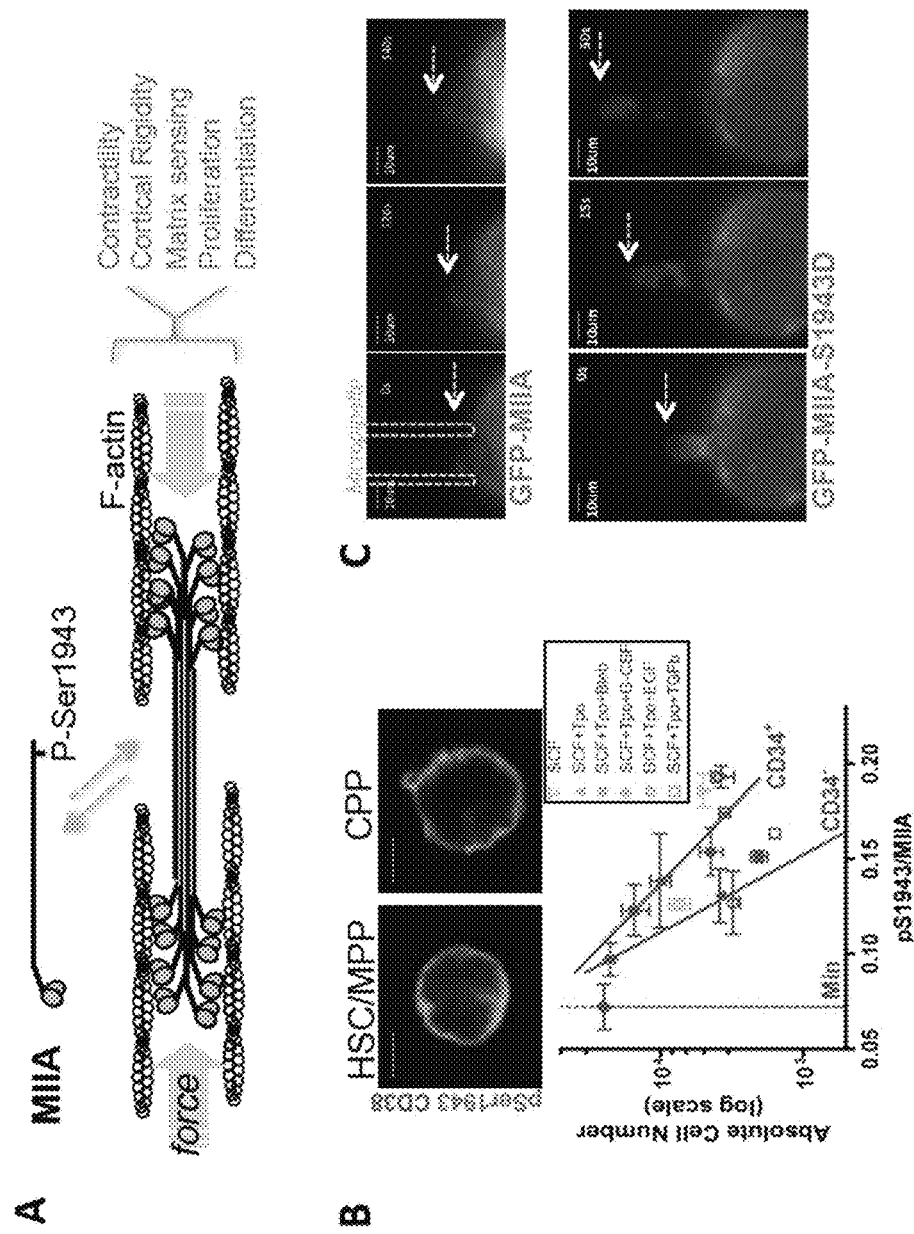
FIG. 18, comprising
Figure 18:
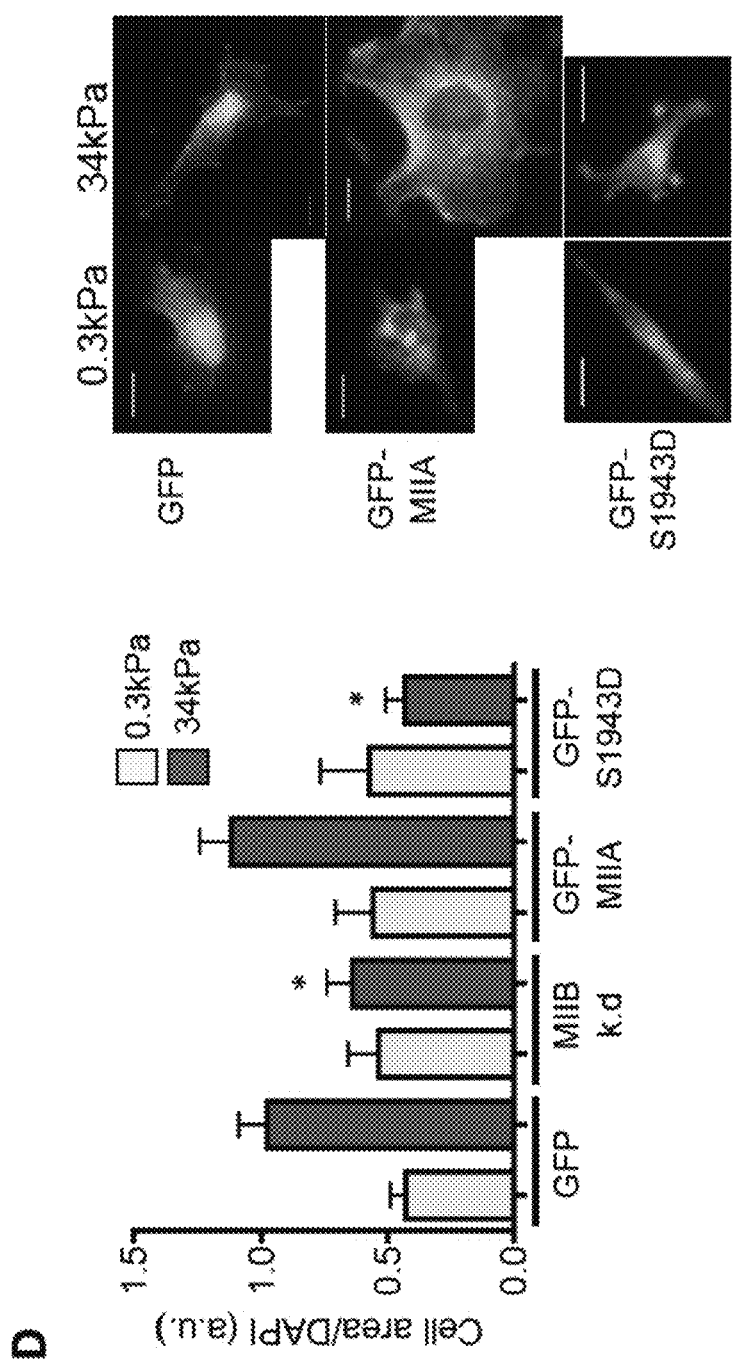

While NMM-IIA appears ubiquitous across different tissue types, NMM-IIB is more specific to cell types that tend to be anchored within tissues, ranging from brain to cardiomyocytes (Ma et al., 2010, Mol Biol Cell, 21(22): 3952-3962). As with the majority cytoskeletal components, NMMIIA is lower in primitive HSCs and increased during HSC differentiation, and is subjected to phospho-regulation (FIG. 16, FIG. 18). Despite low cytoskeletal contents (soft, highly compliant membrane), HSCs appear to be capable of anchoring to a number of surface receptors, thereby maintaining quiescence by linking to matrix as promoted by high expression of NMM-IIB in CD34+ cells compared to CD34−.

Studies of engraftment here show that long-term human HSCs from myosin-inhibited cultures are functional in the marrows of xenografted mice. In contrast, fresh progenitors including MPP defined here by low CD90 expression show significantly reduced engraftment capability by 3~9 folds (Majeti et al., 2007, Cell Stem Cell, 1(6): 635-645; Notta et al., 2011, Science, 333(6039): 218-221), which is revealing because fresh MPP have a hematopoietic profile that is very highly correlated with fresh HSCs vs. the Bleb-treated HSCs. By comparing expression profiles for these three particular cell samples, a small subset of genes emerges as critically 'up' for long-term engraftment (FIG. 21C). NMM-IIB is among these critical genes, as it is 3-fold downregulated in MPPs relative to fresh HSCs and relative to Bleb-treated HSCs that show even higher levels. Other proteins of interest include ANGPT1, which could be part of an autocrine loop of Angiopoietin-1/Tie2 signaling necessary to maintain HSC quiescence (Arai et al., 2004, Cell, 118(2): 149-161). Not only are many other genes upregulated or downregulated in fresh and treated HSCs, but also are similar in level in MPPs (FIGS. 21A and B), but not in CPPs, indicating that they might be important in conferring at least some short-term engraftment capability (10 weeks or less in NSG mice) on cells. These include upregulated CD34, CD200, PROM1, SELL (L-selectin), ITGA9, and also EMCN—which shows the highest overall upregulation. Endomucin (EMCN) is CD34-like, has anti-adhesive activity, and has been shown important to engraftment of mouse-HSCs (Matsubara et al., 2005). Genes that are mutually downregulated in fresh HSCs with Bleb-treated HSCs include CD38, CD226, ITGA2B, and ITGB3, the latter of which confirms some specificity in matrix recognition. Further studies of these various proteins are needed to clarify how essential and how specialized they are in engraftment and niche interactions.

NMM-II-mediated HSC/P differentiation appears to be sensitive to the nature of cytokines. The mechanism by which a HSC/P cell becomes sensitive to specific differentiation signals remains to be further investigated. However, a recent study in mouse appears to support this notion, demonstrating that even at the naïve HSC level, two distinct types of HSCs exist in terms of their myeloid and lymphoid differentiation bias (Challen et al., 2010, Cell Stem Cell, 6(3): 265-278). Interestingly, the same study also shows that TGF-beta stimulates myeloid-HSC proliferation, while it inhibits lymphoid-HSC turnover. It is likely that HSCs from human CD34+ cells are mostly represented by lymphoid-HSCs given that TGF-beta generally suppresses HSC differentiation via maintaining pS1943 in NMM-IIA (FIG. 18B) and that the majority of human lineages are lymphoid after BM reconstitution in the NSG model (FIG. 20E, Top). While erythroid progenitors can be obtained by culturing cells with Epo, they can also be isolated without Epo and with granulocyte-macrophage inducing cytokines and Bleb (FIG. 20B). Therefore, pharmacological NMM-II inhibition is a negative selection tool to determine which hematopoietic subpopulations remain resistant to a given stimulus of interest. NMM-II inhibition enriches for engraftable HSCs by selectively removing non-engrafting cells without the need for labeling membrane antigens that can compromise physiological receptor function. This has important clinical implications. For instance, patients with advanced-stage cancer can benefit from a life-saving autologous graft after irradiation enriched for tumor-free pure HSCs and freed of rapidly proliferating cancer cells (Weissman and Shizuru, 2008, Blood, 112(9): 3543-3553). In addition, unlike progenitors and mature cells, purified HSCs do not induce graft vs. host disease, which is the primary cause of morbidity and mortality after allogeneic BM transplantation. Under specific conditioning regimens, such as, antibody neutralization of NK cells (Shizuru et al., 1996, Biol Blood Marrow Transplant, 2(1): 3-14) and lymphoid irradiation with anti-thymocyte serum (Lowsky et al., 2005, N Engl J Med, 353(13): 1321-1331), pure allogeneic HSCs can be successfully engrafted into patients. Therefore, the enrichment of engraftable HSCs by NMM-II inhibition represents a novel strategy that should be clinically translatable to HSC transplants, particularly those envisioned with cord blood HSC cultures (Boitano et al., 2010, Science, 329(5997) that should obey the basic cell biology principles elaborated here for myosin-II.

Example 3: Label-Free Enrichment of Rare Blood Cells Via a Novel Engineered Bone Marrow Vascular Niche The present invention describes an apparatus that models vascular microenvironment in marrow. It is designed to confer soft properties on resident cells and inhibit their contractile properties. In this environment, non-dividing cells survive, while dividing cells are eliminated. Therefore, the apparatus offers a low-cost and easy-to-use platform to enrich both known and unknown rare blood cells and characterize them functionally without utilizing specific biological markers. Specifically, the present invention demonstrates simultaneous enrichment of two rare marrow cells, blood-forming stem cells, and platelet producing megakaryocytes. This has important implications for cost-effective scientific research and regenerative medicine.

Described herein is a low-cost easy-to-use apparatus that can be used to isolate rare blood cells. The method allows simultaneous isolation of rare blood cells (including HSCs and MKs) present in a heterogeneous marrow cell population without using specific biological markers such as antibodies. A drug-embedded tunable material functionalized with extracellular matrix is used to simulate soft tissue surface to confer soft properties on cells. The apparatus is designed as a cylindrical mini-bioreactor. The bioreactor is coated with the material and bone marrow-derived cells are incubated within the bioreactor, which is then directly converted to a syringe to elute viable product cells.

Figure 28:
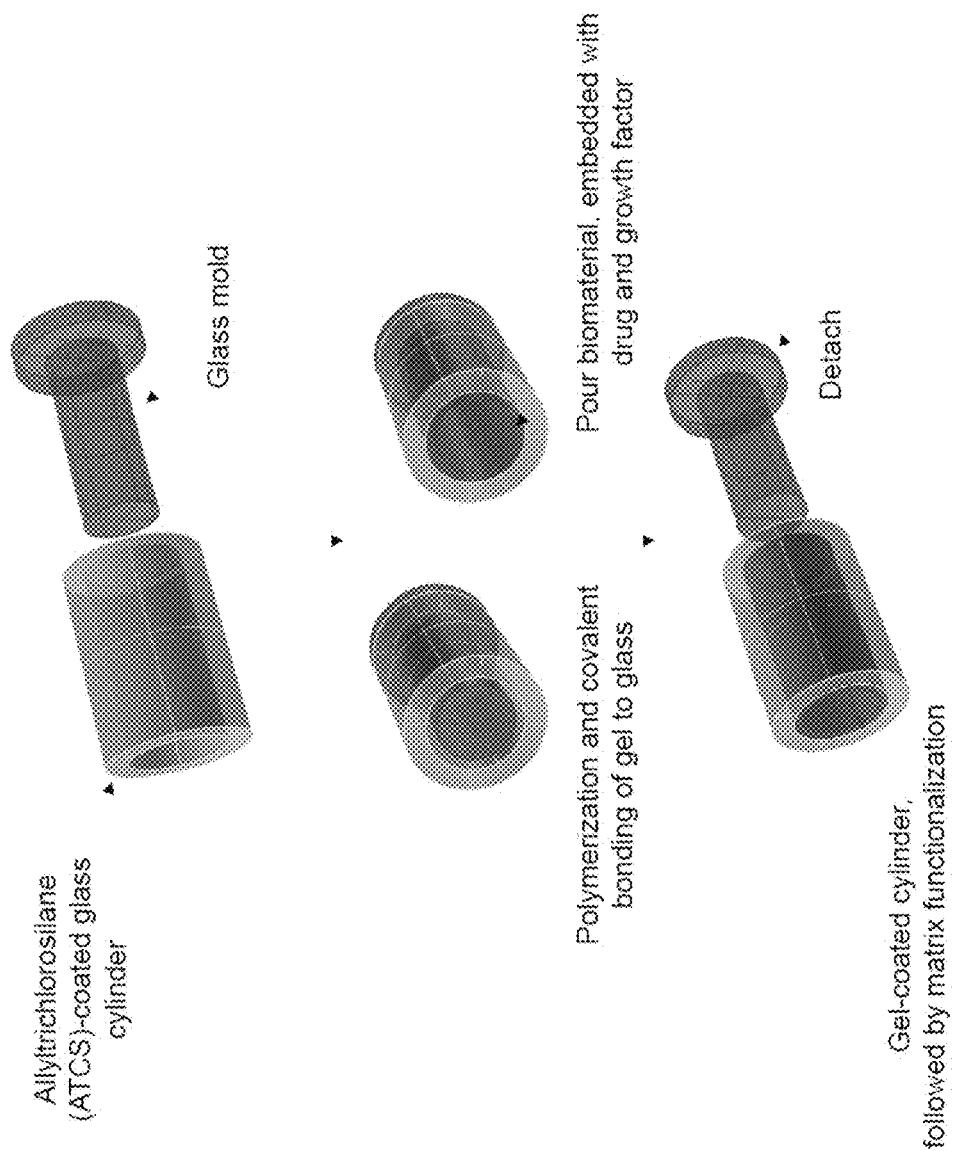
FIG. 28 depicts the process in which the inner surface of the housing of the bioreactor is coated with the biomaterial substrate of the invention.

The apparatus uses two ways to achieve softness of resident cells. First, cell culture surface is engineered to maintain soft property by polymerizing polyacrylamide gel with minimal cross-linking. Second, pharmacological strategy is used to make cells soft by inhibiting proteins responsible for maintaining cellular contractility, including myosin-II. The combination of these two methods leads to matrix-elasticity tunable solid biomaterial that is embedded with inhibitors of myosin-II (e.g. blebbistatin) and minimal growth factors necessary to maintain bone marrow cells (e.g. Stem Cell Factor, Thrombopoietin). This biomaterial is covalently coated on the glass cylindrical surface of a mini-bioreactor via silane chemistry with allyltrichlorosilane (ATCS) solution and molding using a construct (FIG. 28). After coating the biomaterial, it is functionalized with extracellular matrix proteins including collagen-I and fibronectin via an amine-reactive cross-linker, such as sulfo-SANPAH.

Figure 29:
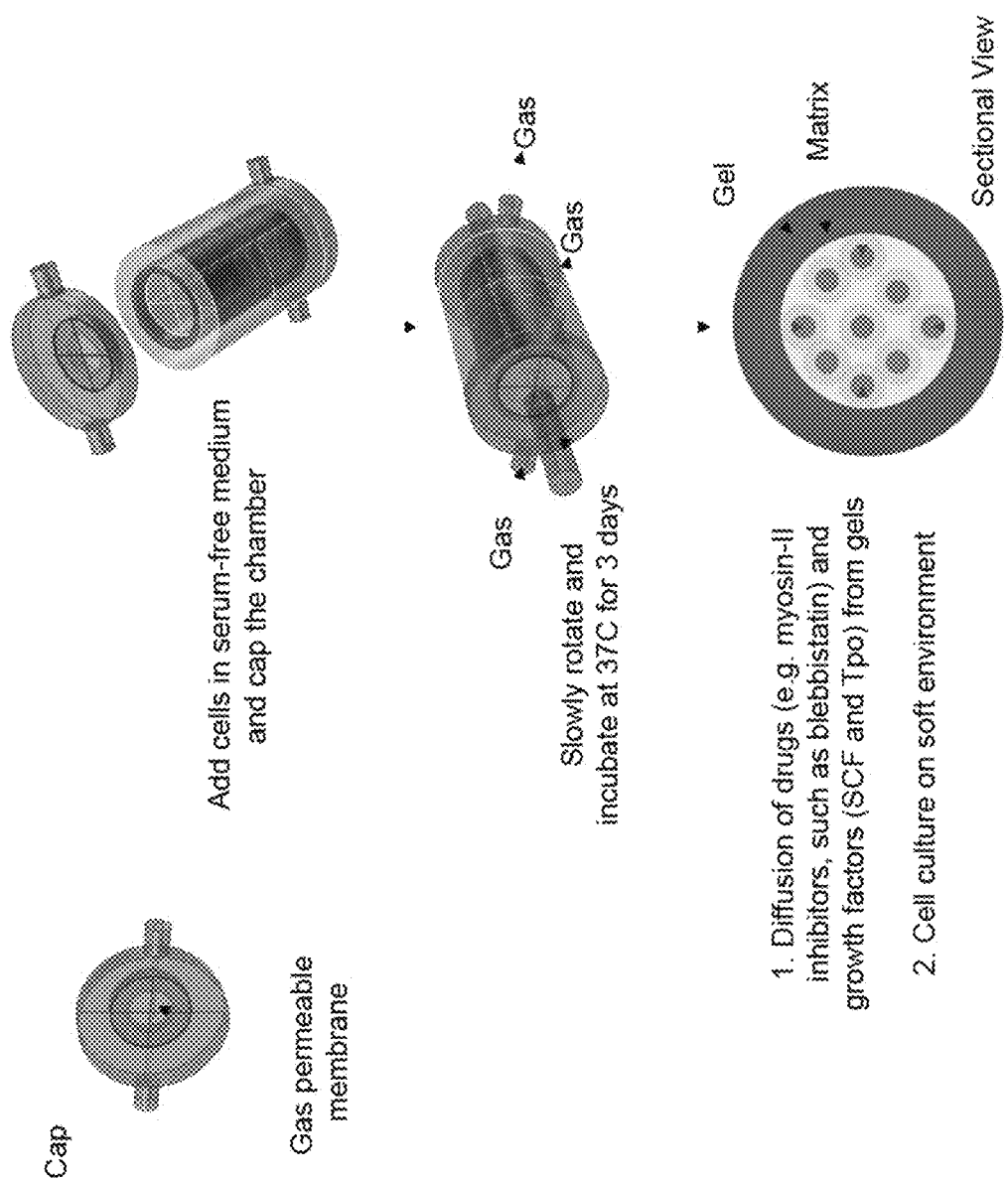
FIG. 29 depicts the addition of gas permeable caps to the bioreactor and the culturing of a cell population within the bioreactor.
Figure 30:
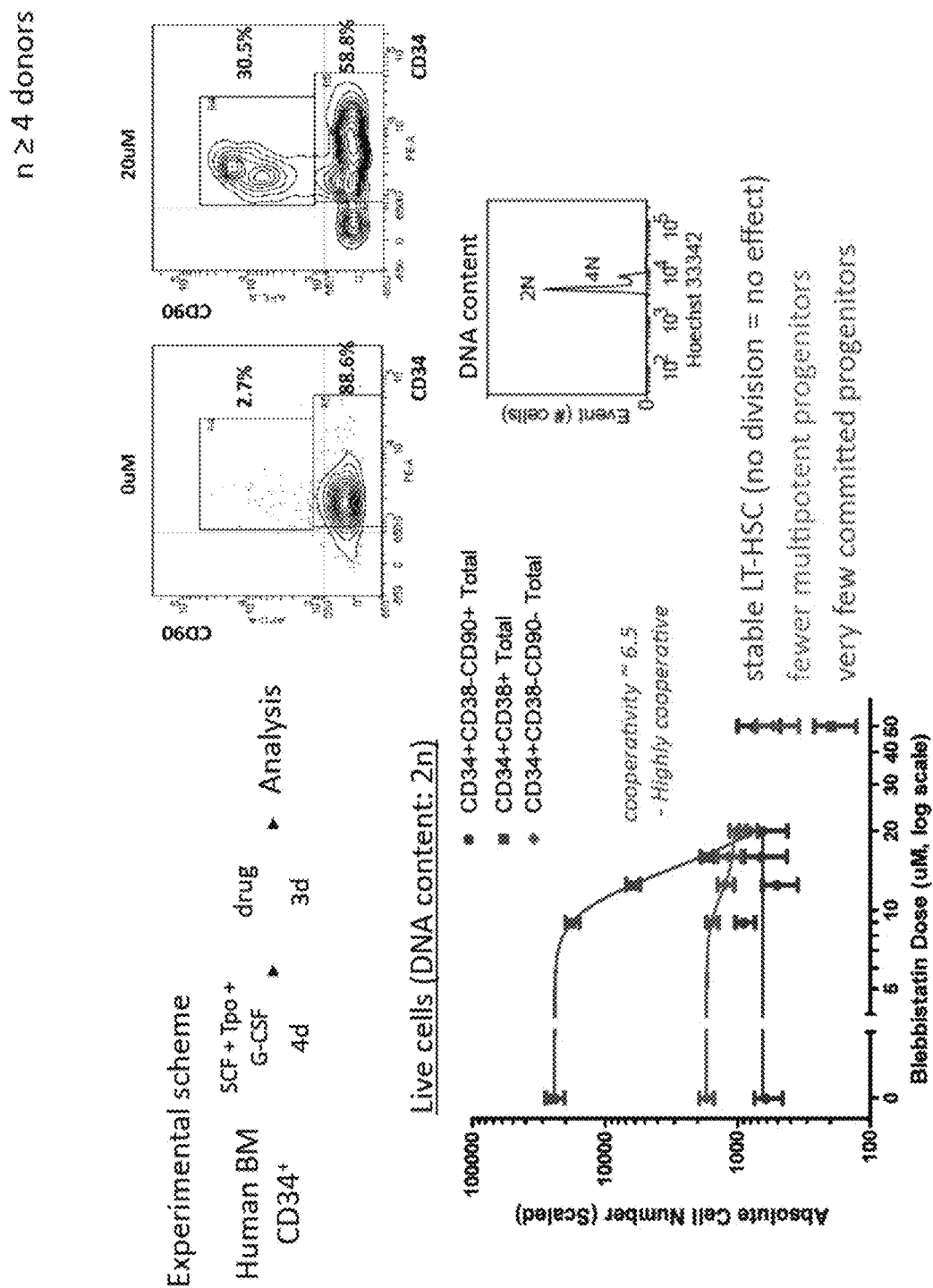
FIG. 30 depicts the results from example experiments which demonstrate that myosin-II inhibition, through application of blebbistatin, enriches long term hematopoietic stem cells through the selective suppression of progenitors.
Figure 31:
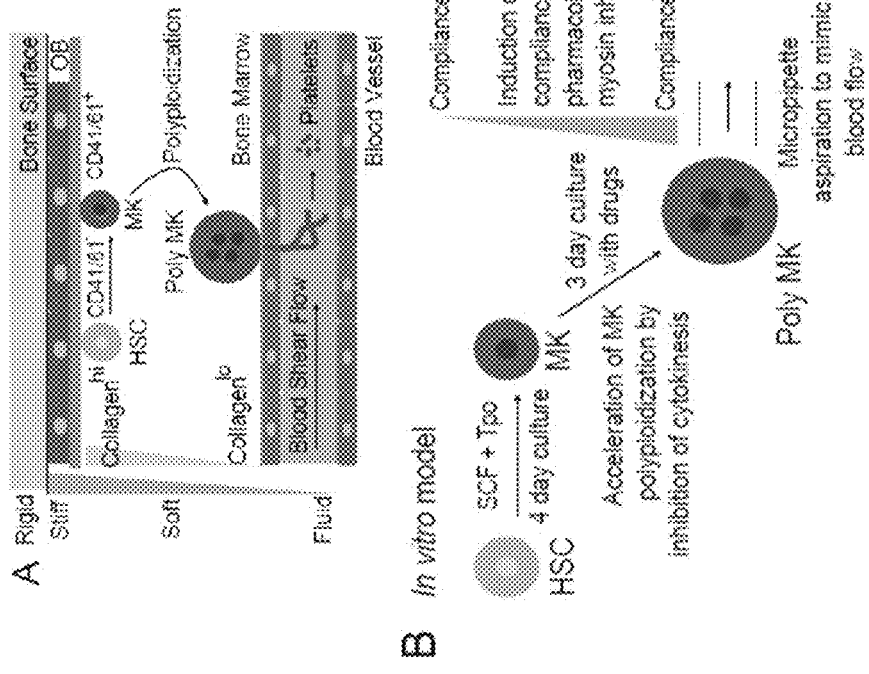
FIG. 31, comprising
Figure 32:
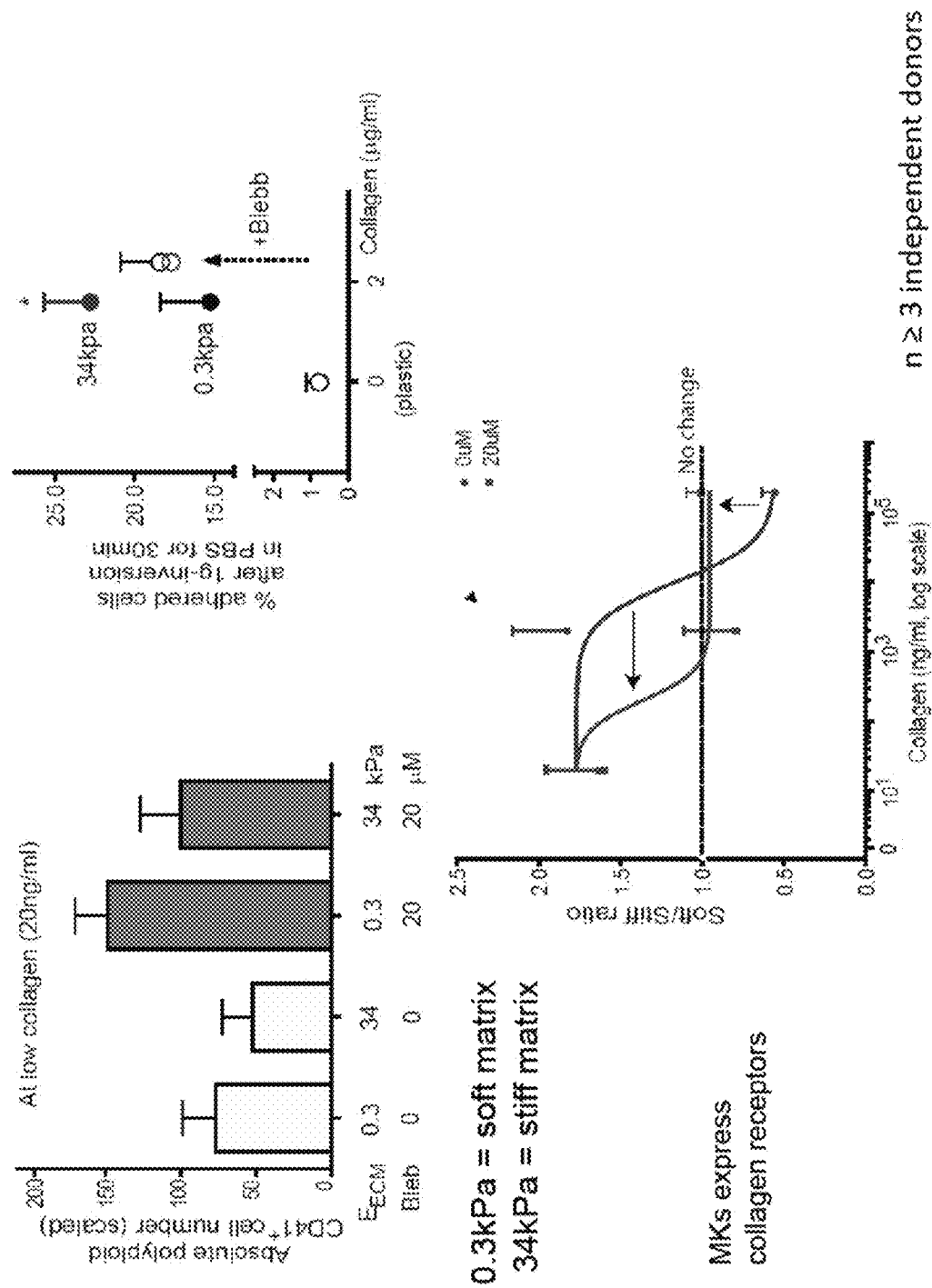
FIG. 32 depicts the results of experiments which demonstrate that soft substrates and low collagen coated substrates, with myosin-II inhibition, maximizes MK maturation.
Figure 33:
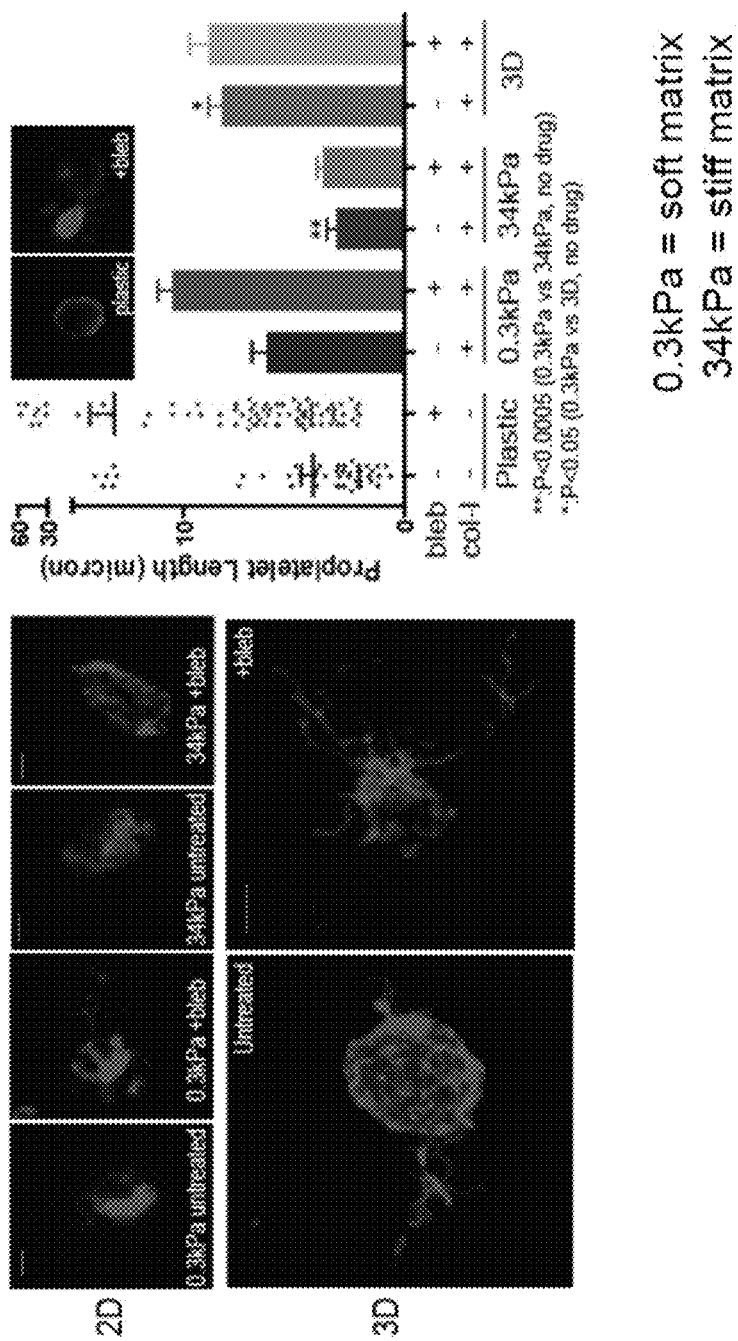
FIG. 33 depicts the results of experiments which demonstrate that soft 2D collagen coated matrices maximizes MK proplatelet formation, as measured by the proplatelet length.
Figure 34:
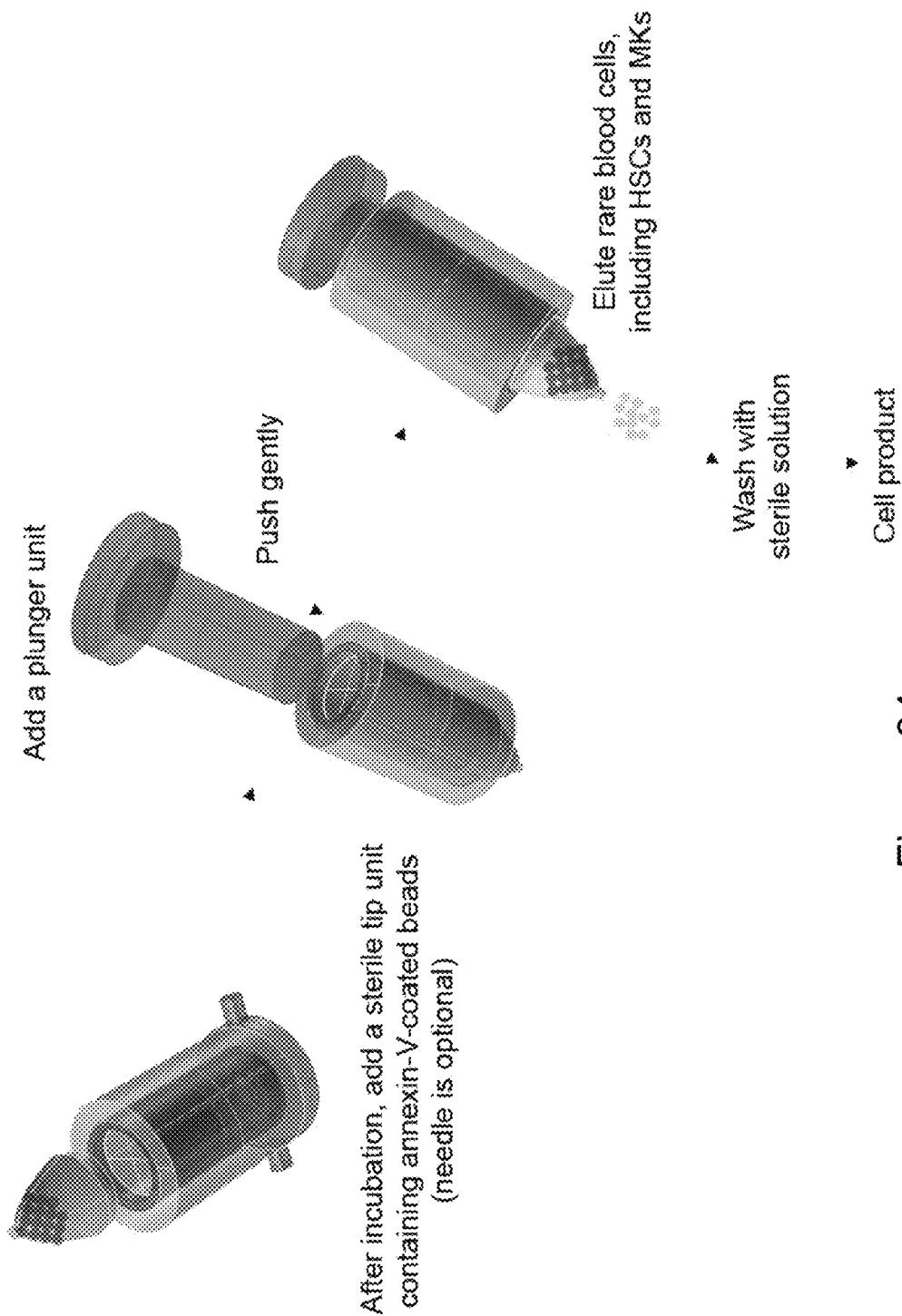
FIG. 34 depicts the conversion of the bioreactor into its syringe conformation, the capturing of non-viable cells through the addition of Annexin-V coated beads, and the elution of rare blood cells.
Figure 35:
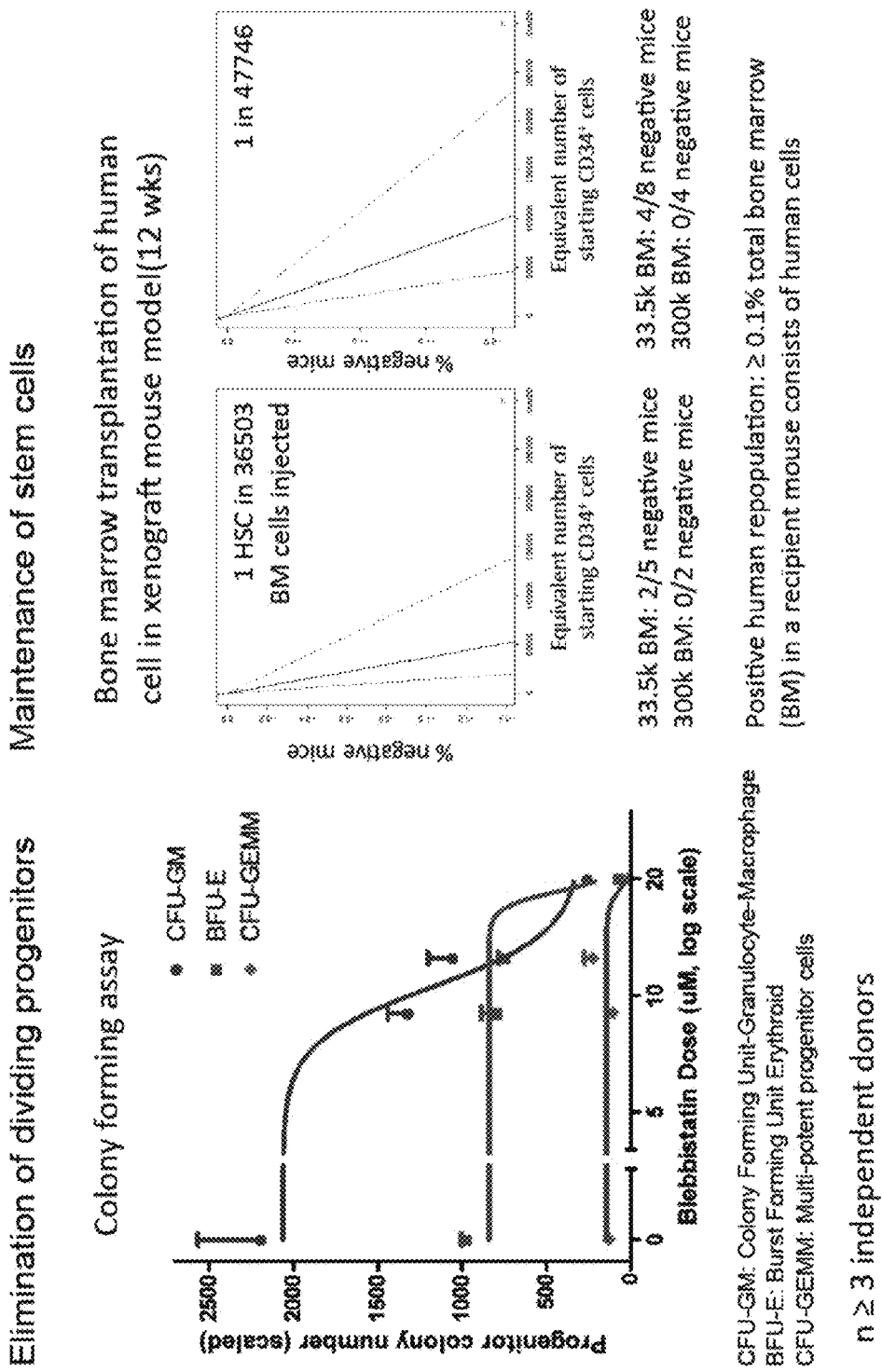
FIG. 35 depicts the results of experiments which demonstrate the functional verification of human HSCs enriched through myosin-II inhibition by the examination of the total blood reconstitution capabilities in a xenograft mouse model. Maintenance of stem cells was observed 12 weeks post bone marrow transplantation of human cells in the mouse xenograft model.
Figure 36:
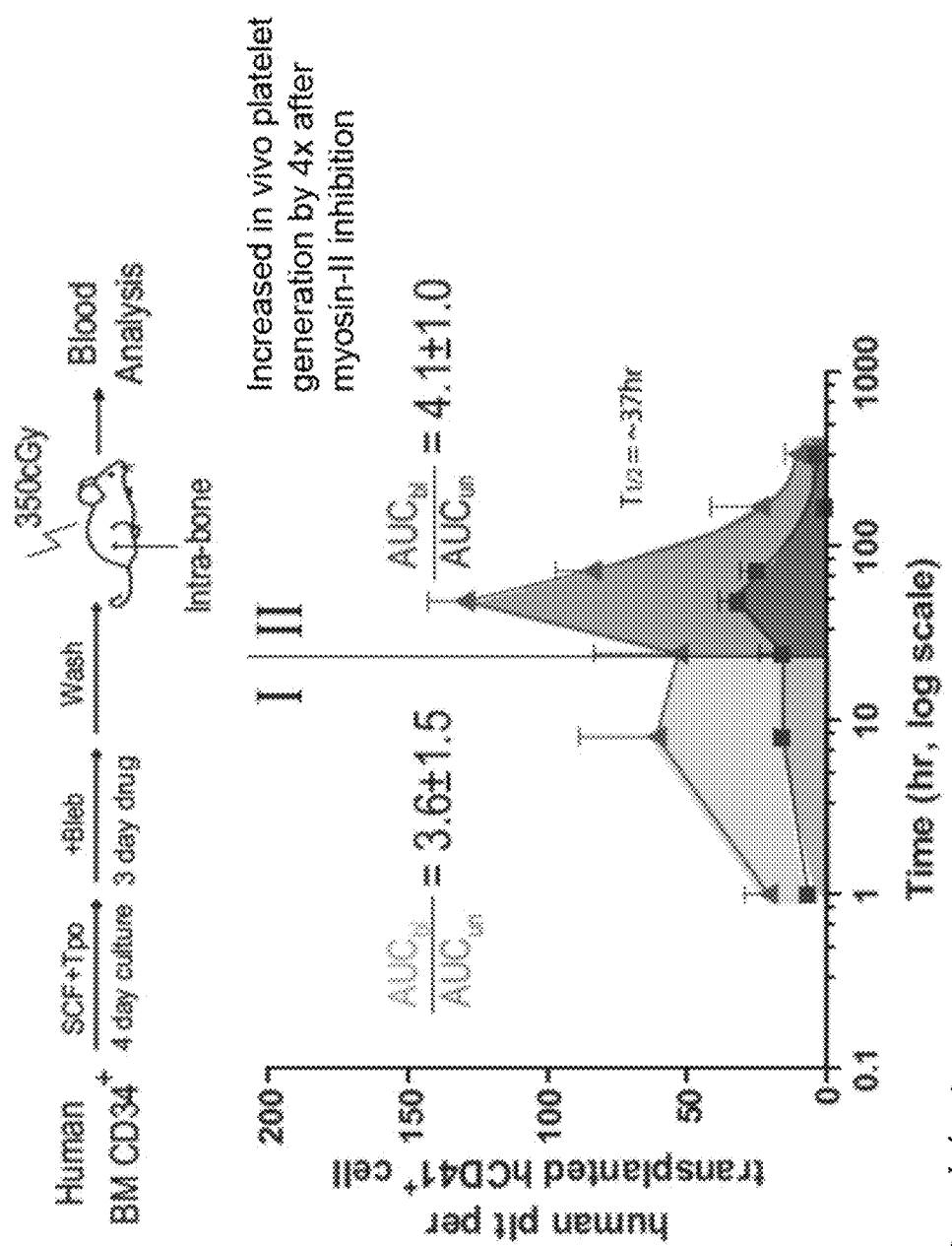
FIG. 36 depicts the results of experiments which demonstrate the functional verification of human MKs enriched through myosin-II inhibition. It was observed that myosin-II inhibition of human CD34+ cells increased in vivo platelet generation in a xenograft mouse model.

Cells derived from bone marrow biopsy of patients are then resuspended in serum-free medium and incubated in the bioreactor at 37° C. for 3 days. Over time, drugs and growth factors embedded into the biomaterial diffuse into the reaction medium, and cells sense the soft environment (FIG. 29). Importantly, data presented herein indicates that cells with lower proliferative capacity (i.e. rare blood cells) survive under the condition that cells become soft by a selective inhibitor against myosin-II, while those with higher proliferative capacity (e.g. progenitors) do not survive (FIG. 30). Under the same conditions, MKs become mature, as indicated by increased number of multi-nucleate cells (DNA content ≥8N, equivalent to 3 nuclei or more per cell), which are capable of generating more platelets per cell compared to uni (2N) or bi (4N)-nucleate cells (FIG. 31). In addition, the present data indicates that direct culturing of cells on soft collagen-coated polyacrylamide gels leads to increased maturation of MKs compared to cells on stiffer gels, as indicated by increased number of multi-nucleate cells (FIG. 32) and increased proplatelet (projection) formation (FIG. 33). Therefore, the overall effect of using the apparatus is the enrichment of HSCs and MKs. In some cases, it may be important to remove dead cells. To achieve this, cells after incubation are passed through magnetic beads coated with Annexin-V antibody that bind to dead cells (FIG. 34). Functionality of both human HSCs (FIG. 35) and MKs (FIG. 36) isolated from this method—complete blood cell reconstitution and platelet generation, respectively—was demonstrated by in vivo experiments using xenotransplantation mouse model.

wherein the substrate layer comprises a composition comprising at least one anti-contractility agent selected from the group consisting of blebbistatin, ML-7, and Y-27632;

wherein the substrate layer comprises cross-linked polyacrylamide gel having stiffness of about 0.3 kPa to 2 kPa; and wherein the rare blood cells comprise polyploid megakaryocytes, polyploid non-megakaryocytes, granulocyte-macrophage progenitors, and erythroid progenitors.

2. The apparatus of claim 1, wherein the composition is embedded within the substrate layer.

3. The apparatus of claim 1, wherein the substrate layer is coated with at least one protein selected from the group consisting of collagen, fibronectin, laminin, and vitronectin.

4. A method of isolating rare blood cells from a heterogeneous population of hematopoietic cells, the method comprising the steps of:

(a) culturing a heterogeneous population of hematopoietic cells obtained from a subject within an apparatus having a substrate layer, wherein the heterogeneous population of hematopoietic cells is in contact with a least a portion of the substrate layer, wherein the apparatus comprises a hollow tube housed within a syringe, wherein the hollow tube comprises: two opposing openings and an inner surface to form a passage therethrough, a sterile tip attached to one

What is claimed:

1. An apparatus for the isolation of rare blood cells from a heterogeneous population of hematopoietic cells, the apparatus comprising:
   a hollow tube housed within a syringe, wherein the hollow tube comprises: two opposing openings and an inner surface to form a passage therethrough, a sterile tip attached to one opening of the hollow tube, and a plunger unit inserted into and through the opposing opening of the hollow tube;
   rare blood cells; and
   a substrate layer on at least a portion of the inner surface of the hollow tube, wherein the rare blood cells are in contact with at least a portion of the substrate layer;

opening of the hollow tube, and a plunger unit inserted into and through the opposing opening of the hollow tube;

wherein the substrate layer is on at least a portion of the inner surface of the tube;

wherein the substrate layer comprises cross-linked polyacrylamide gel having a stiffness of about 0.3 kPa to 2 kPa;

wherein the substrate layer comprises a composition comprising at least one anti-contractility agent selected from the group consisting of blebbistatin, ML-7, and Y-27632; and wherein the rare blood cells comprise polyploid megakaryocytes, polyploid non-megakaryocytes, granulocyte-macrophage progenitors, and erythroid progenitors; and (b) removing non-viable cells from the population of cells, thereby isolating rare blood cells from a heterogeneous population of hematopoietic cells.

5. The method of claim 4, wherein the at least one composition is embedded within the substrate layer.

6. The method of claim 4, wherein the surface of the substrate layer is coated with at least one protein selected from the group consisting of collagen, fibronectin, laminin, and vitronectin.

7. The method of claim 4, wherein the rare blood cells are used to program the outcome of blood cell transplantation in a subject.

8. The method of claim 7, wherein the rare blood cells are used to perform at least one function selected from the group consisting of early recovery of platelet count, clearance of granulocyte-macrophage progenitors, maintenance of long term hematopoietic stem cell activity and red blood cell generation.

9. The apparatus of claim 1, wherein the composition further comprises an aryl-hydrocarbon receptor antagonist selected from the group consisting of StemRegenin-1, CH-223191 and resveratrol.

10. The apparatus of claim 9, wherein the composition further comprises a growth factor.

11. The apparatus of claim 10, wherein the growth factor is selected from the group consisting of stem cell factor (SCF), glial cell line-derived neurotrophic factor (GDNF), GDNF-family receptor (including GFR$\alpha$1), leukemia inhibitory factor (LIF), hepatocyte growth factor (HGF), acidic fibroblast growth factor (aFGF), epidermal growth factor (EGF), insulin-like growth factor, keratinocyte growth factor (KGF), nerve growth factor (NGF), transforming growth factor beta (TGF-$\beta$), vascular endothelial cell growth factor (VEGF), platelet-derived growth factor (PDGF), FMS-like tyrosine kinase 3 ligand (Flt3L or Flt3LG), transforming growth factor, interleukins, colony-stimulating factors, Sonic hedgehog, notch, leptin, hormones, and interferons.

* * * * *